(12) United States Patent
Yamasaki et al.

(10) Patent No.: US 8,586,327 B2
(45) Date of Patent: Nov. 19, 2013

(54) **DETECTION OF BACTERIA BELONGING TO THE GENUS *CAMPYLOBACTER* BY TARGETING CYTOLETHAL DISTENDING TOXIN**

(75) Inventors: Shinji Yamasaki, Sakai (JP); Worada Samosorunsuk, Sakai (JP); Masahiro Asakura, Osaka (JP)

(73) Assignees: Osaka Prefecture University, Osaka (JP); Fuso Pharmaceutical Industries, Ltd., Osaka (JP)

(*) Notice: Subject to any disclaimer, the term of this patent is extended or adjusted under 35 U.S.C. 154(b) by 528 days.

(21) Appl. No.: 12/675,726

(22) PCT Filed: Aug. 29, 2008

(86) PCT No.: PCT/JP2008/065532
§ 371 (c)(1),
(2), (4) Date: Jun. 28, 2010

(87) PCT Pub. No.: WO2009/028662
PCT Pub. Date: Mar. 5, 2009

(65) Prior Publication Data
US 2010/0273161 A1 Oct. 28, 2010

(30) Foreign Application Priority Data
Aug. 31, 2007 (JP) ................... 2007-226013

(51) Int. Cl.
*C12P 21/06* (2006.01)
*C12N 15/00* (2006.01)
*C07H 21/02* (2006.01)
*C07K 14/00* (2006.01)

(52) U.S. Cl.
USPC ...... 435/69.1; 435/320.1; 435/325; 536/23.1; 530/350

(58) Field of Classification Search
USPC .............. 530/350; 536/23.1; 435/320.1, 69.1, 435/325
See application file for complete search history.

(56) References Cited

U.S. PATENT DOCUMENTS

| | | | |
|---|---|---|---|
| 5,447,848 A | 9/1995 | Barns et al. | |
| 5,691,138 A | 11/1997 | Guesdon et al. | |
| 5,998,138 A | 12/1999 | Stonnet et al. | |
| 7,563,594 B2 * | 7/2009 | Yamasaki et al. | 435/69.1 |
| 7,595,386 B2 | 9/2009 | Borelli | |
| 2010/0047797 A1 | 2/2010 | Yamasaki et al. | |
| 2010/0069611 A1 | 3/2010 | Yamasaki et al. | |

FOREIGN PATENT DOCUMENTS

| | | |
|---|---|---|
| EP | 0350205 B1 | 2/1995 |
| EP | 0711841 | 5/1996 |
| EP | 1 698 698 | 9/2006 |
| JP | 62228096 | 10/1987 |
| JP | 284200 | 3/1990 |
| JP | 2154700 | 6/1990 |
| JP | 3112498 | 5/1991 |
| JP | 5276999 | 10/1993 |
| JP | 690795 | 4/1994 |
| JP | 690796 | 4/1994 |
| JP | 7505535 | 6/1995 |
| JP | 10-508449 | 8/1998 |
| JP | 2000316590 | 11/2000 |
| JP | 2001524825 | 12/2001 |
| WO | 96/15261 | 5/1996 |
| WO | WO9842842 | 10/1998 |
| WO | 01/77372 | 10/2001 |
| WO | 2005/054472 | 6/2005 |

OTHER PUBLICATIONS

Dassanayake et al. Apr. 2006; Characterization of a novel *Campylobacter* cytolethal distending toxin in *Campylobacter hyointestinalis* subsp. *Hyointestinalis* isolated from humans and pigs. DQ497437; Apr. 2006. Alignment with SEQ ID No. 1 and SEQ ID No. 3.*

Yamasaki et al. USP 7,563,594, Alignment with SEQ ID No. 1, 2, 3, 4, 5, 6, 7, and 8, 2013.*

Unpublished U.S. Appl. No. 13/458,532, filed Apr. 27, 2012 entitled "Cytolethal Distending Toxins and Detection of *Campylobacter* Bacteria Using the Same as a Target" and assigned to Fuso Pharmaceutical Industries, Ltd.

Abuoun, et al., "Cytolethal Distending Toxin (CDT)-Negative *Campylobacter jejuni* Strains and Anti-CDT Neutralizing Antibodies Are Induced during Human Infection but Not during Colonization in Chickens" Infection and Immunity, (May 2005) 73(5):3053-3062.

(Continued)

*Primary Examiner* — Karen Cochrane Carlson
(74) *Attorney, Agent, or Firm* — Karl Bozicevic; Bozicevic, Field & Francis LLP

(57) ABSTRACT

An objective of the present invention is to provide the cytolethal distending toxin (CDT) of *C. hyointestinalis* and polynucleotides encoding it, and novel methods for detection of *C. hyointestinalis* using the cdt genes. The present inventors focused on the cytolethal distending toxin (CDT) of *Campylobacter* bacteria, and detected the cdt genes of a *Campylobacter*-like bacterium isolated from an enteritis patient in Thailand. The present inventors discovered a bacterial strain whose cdtB gene was amplified by common primers in *C. jejuni*, *C. coli*, and *C. fetus*, but not by multiplex PCR that can specifically detect the cdtA, cdtB, and cdtC genes of the three bacterial species. The bacterial strain was identified as *C. hyointestinalis* by 16S rRNA gene analysis. Furthermore, the entire nucleotide sequence of the cdt genes was determined by genome walking upstream and downstream of the cdtB gene.

9 Claims, 17 Drawing Sheets

(56) References Cited

OTHER PUBLICATIONS

Lutful Kabir et al., "Evaluation of a Cytolethal Distending Toxin (cdt) Gene-Based Species-Specific Mutliplex PCT Assay for the Identification of *Campylobacter* Strains Isolated from Diarrheal Patients in Japan" Jpn. J. Infect. Dis. (2011) 64:19-27.
Asakura et al., "Comparative analysis of cytolethal distending toxin (cdt) genes among *Campylobacter jejuni*, *C. coli* and *C. fetus* strains", Microb Pathog. May-Jun. 2007:42(5-6):174-83. Epub Feb. 6, 2007.
Asakura et al., "Cloning of the CDT gene of *Campylobacter fetus* and analysis thereof" Japanese Journal of Bacteriology. 204:59(1):283(#3093).
Asakura et al., "Molecular epidemiological investigation on CDT-producing *Campylobacter* isolated from domestic animals" Japanese Journal of Bacteriology. 2005:60(1):165(#P2-162).
Bang et al., "Prevelence of cytolethal distending toxin (cdt) genes and CDT production in *Campylobacter* spp. isloated from Danish broilers." J Med Microbiol. Dec. 2001:50(12):1087-94.
Dassanayake et al., "*Campylobacter hyointestinalis* strain MN-P-80-4577-4 cytolethal distending partial cds" GenBank Accession No. DQ497437: May 17, 2006.
Lastovica et al., "Clinical Significance of *Campylobacter* and Related Species Other Than *Campylobacter jejuni* and *C. Coli*" *Campylobacter*. 2000:2nd ed: 89-120.
Pickett et al., "Prevelence of Cytolethal Distending Toxin Production in *Campylobacter jejuni* and Relatedness of *Campylobacter* sp. cdtB Genes" Infect Immun. Jun. 1996: 64(6):2070-8.
Samusurunsuku et al., "Molecular characterization of cytolethal distending toxin of *Campylobacter hyointestinalis*" Japanese Journal of Bacteriology. Feb. 25, 2007: 62(1):103(#P-129).
Yamasaki et al., "Cytolethal Distending Toxin (CDT): Genetic Diversity, Structure and Role in Diarrheal Disease" Toxin Reviews. 2006:25(1):61-68.
Asakura et al., "Development of a Multiplex PCR Assay for the Detection of the Cytolethal Ditending Toxin Genes in *Campylobacter jejuni*, *C. coli* and *C. fetus*" Abstracts of the General Meeting of the American Society for Microbiology. May 24, 2004; 104th:209 (#D-091).
Asakura, "Development of a rapid method for identifying *Campylobacter jejuni*, *C. coli*, and *C. fetus* bacterial species using Cytolethal distending toxin (cdt) gene and application thereof" Presentation of doctoral thesis of the Osaka Prefecture University, Graduate School of Agricultural and Life Sciences, Division of Veterinary Science, Feb. 27, 2007.
Asakura, "Development of a rapid method for identifying *Campylobacter jejuni*, *C. coli*, and *C. fetus* bacterial species using Cytolethal distending toxin (cdt) gene and application thereof" Osaka Prefectur University Graduate School (Veterinary Science) Doctoral Thesis, Jun. 20, 2007.
Bang et al., "PCR detection of seven virulence and toxin genes of *Campylobacter jejuni* and *Campylobacter coli* isolates from Danish pigs and cattle and cytolethal distending toxin production of the isolates" Journal of Applied Microbiology, 94:1003-1014 (2003).
Blaser et al., "*Campylobacter* Enteritis: Clinical and Epidemiologic Features" Ann. Intern. Med. (Aug. 1979) 91 (2):179-85.
Cortes-Bratti et al., "The *Haemophilus ducreyi* Cytolethal Distending Toxin Induces Cell Cycle Arrest and Apoptosis via the DNA Damage Checkpoint Pathways" J. Biol. Chem. (Feb. 16, 2001) 276(7):5296-302.
Eyigor et al., "Cytolethal Distending Toxin Genes in *Campylobacter jejuni* and *Campylobacer coli* Isolates: Detection and Analysis by PCR" Journal of Clinical Microbiology, 37(5):1646-1650 (May 1999).
Eyigor et al., "Detection of Cytolethal Distending Toxin Activity and cdt Genes in *Campylobacter* spp. Isolated from Chicken Carcasses" Applied and Environmental Microbiology, 65(4):1501-1505 (Apr. 1999).
Gene Bank accession No. U51121.
Kopecko et al., "*Campylobacter jejuni*-microtubule-dependent invasion" Trends Microbiol. (Aug. 2001) 9(8):389-96.
Kudoh et al., Syouni naika. (1997) 29(9):1219-22.
Lara-Tejero et al., "A Bacterial Toxin That Controls Cell Cycle Progression as a Deoxyribonuclease I-Like Protein" Science (Oct. 13, 2000) 290(5490):354-7.
Lara-Tejero et al., "Cytolethal distending toxin: limited damage as a strategy to modulate cellular functions" Trends Microbiol., (Mar. 2002) 10(3):147-52.
Martinez et al., "Detection of cdtA, cdtB, and cdtC genes in *Campylobacter jejuni* by multiplex PCR" International Journal of Medical Microbiology, 296(1):45-48 (2006).
Mizuno et al., "Characteristics of cytotoxin produced by *Campylobacter jejuni* strains" Microbios. (1994) 78 (317):215-28.
Okuda et al., "Examination of Diarrheagenicity of Cytolethal Distending Toxin: Suckling Mouse Response of the Products of the cdtABC Genes of *Shigella dysenteriae*" Infect Immun. (Feb. 1997) 65(2):428-33.
Oyofo et al., "Specific Detection of *Campylobacter jejuni* and *Campylobacter coli* by Using Polymerse Chain Reaction" J Clin Microbiol. (Oct. 1992) 30(10):2613-9.
Pickett et al., "The cytolethal distending toxin family" Trends Microbiol. (Jul. 1999) 7(7):292-7.
Romaniuk et al., "*Campylobacter pylori*, the Spiral Bacterium Associated with Human Gastritis, Is Not a True *Campylobacter* sp." J Bacteriol. (May 1987) 169(5):2137-41.
Shane et al., Diseases of Poultry, (2003) 615-30.
Shiramaru et al., "Shu Tokuiteki Cytolethal distending toxin Idenshi ni Motozuku nested-multiplex PCR o Mochita *Campylobacter*-zoku Saikin no Jinsoku Kenshutsu" Proceedings of the 143rd meeting of the Japanese Society of Veterinary Science, 143rd:201 (#FP2-195) (Mar. 15, 2007) (International Search Report attached for a concise explanation).
Suzuki et al., "Immunological properties and ganglioside recognitions by *Campylobacter jejuni*-enterotoxin and cholera toxin" FEMS Immunol Med Microbiol. (Mar. 1994) 8(3):207-11.
Takahashi et al., Infectious Diseases Weekly Report Japan (2001) 3(6):10-2.
Tauxe, Robert V., "Epidemiology of *Campylobacter jejuni* Infections in the United States and Other Industrialized Nations" *Campylobacter jejuni*: Current Status and Future Trends. 1991:9-19, American Society for Microbiology.
Totten et al., "Prevalence and Characterization of Hippurate-Negative *Campylobacter jejuni* in King County, Washington" J Clin Microbiol. (Sep. 1987) 25(9):1747-52.
Volokhov et al., "Microarray-Based Identification of Thermophilic *Campylobacter jejuni*, *C. coli*, *C. lari*, and *C. upsaliensis*" Journal of Clinical Microbiology, 41(9):4071-4080 (Sep. 2003).
Database Uniprot [Online] "Cytolethal distending toxin C (dctC) of *Campylobacter jejuni*" XP002646136, accession No. UNIPROT: Q5F1K4 *Amino Acid Sequence* (Mar. 2005).
Stratagene Catalog (1988); cover and p. 39.

* cited by examiner

```
C. jejuni   MKK-IICLFLSFNLAFANLENFNVGTWNLQGSSAATESKWSVSVRQLVSGANPLDILMIQ    59
C. coli     ...-.VF.I....VL..A...Y.T.................N..I...IT....M.V.AV.   59
C. fetus    .RN-V.MIIFIAT.G..KP.DYKIA.........I.....NI....II..E..A...AV.   59
C. hyo#     ...FL.V.L.C.STLL..I.DYSIA...M...........N.NI...I..NSAA...LV.   60

60    EAGTLPRTATPTGRHVQQG--GTPIDEYEWNLGTLSRPDRVFIYYSRVDVGANRVNLAIV   117
60    ...V..S..MM.P.Q..PVGV.I..H..I....SV...SS.Y..................   119
60    ...N..Q..L....SIN..--..IVT.HL.Q..SI...FQ.Y...AQI.T..........   117
61    ...SI.VS.VY..TV..PVGV.I....FA.....A...NQ....................   120

118   SRMQAEEVIVLPPPTTVSRPIIGIRNGNDAFFNIHALANGGTDVGAIITAVDAHFANMPQ    177
120   ..V..D..F......VA........I..........S..N.A...VA...MF.R.R.D     179
118   ..IK.D.I.I.....VA...L....I...V............V.AP...NSIFDR.R...N 177
121   ..RR.D.........A.......L...V..SV..........AP..VEN.HRF.Q.R.E   180

178   VNWMIAGDFNRDPSTITSTVDRELANRIRVVFPTSATQASGGTLDYAITGNSNRQQTYTP   237
180   I....L......ESGALVTLL.PD.RA.T...V.P.S...T..R.I.........TAAL.N. 239
178   IT...L......S.ESLRG.LGL.TRV.VTFLT.PAP..R......W..V...AGD--LVR 235
181   IS.F.G.....E.NSLLRALEPTVRS.VDI.S.SG...N.......GVA...ATT-SFVA  239

238   PLLAAILMLASLRSHIVSDHFPVNFRKF---   265 (SEQ ID NO: 9 )
240   .PIV...A.EG..TFLA........RP---   267 (SEQ ID NO: 10)
236   TT.V.V....N..T.L.........GDN    266 (SEQ ID NO: 11)
240   .AI..V....NM..Q.T...V....R----  268 (SEQ ID NO: 7 )
```

FIG. 2 cdtB commonU region

```
C. jejuni   5'-ACTTGGAATTTGCAAGGC-3'
C. coli        .................
C. fetus       .................
C. f C90       ........C..A.....T
C. lari        ...........A.....T
C. up          .................
C. hyo22       ........A.........
C. hyATCC      ........A.......A
``` cdtB commonR region

```
C. jejuni   5'-CATTTTCCAGTAAATTTTAG-3'
C. coli        .......T............
C. fetus       .......G............
C. f C90       .......C............
C. lari        .......T..G.........
C. up          .......T..T.........
C. hyo22       ...G.G..T..T........
C. hyATCC      ..C.....TA...CA...G.
```

FIG. 8

```
  1 ATGAAGAAATTTCTTTAT---AGTTTTATTGCTTTGTTTTAGTACTCTACTAGCAAATATTGAAGATTACAGCATCGCT AC  Ch022
  1 .....A.G...AG....CCT...AGCGC.A...A..GC....TTA...T.TAGTGC......T....TT.AA.CA... ..  ChATCC
              ATspBU2  →                                              Ch022spBU1
```

78  TTGGAATATGCAAGGC ICATCTGCTGCAACCGAAAGCAAATGGAATGTCAATATCAGACAACTAATATCAGGCAATAGCG Ch022
 81  ............A...AGC..AAGT.GT...GCT..G....G...T.GC..A.....GA.GT.C......G...AT. ChATCC
ComBU, ChATcomBU, cdtB commonU 153 CAGCTGATATTTTGCTAGTTCAAGAAGCAGGAAGCATACCAGTAAGTGCAGTTTATACAGGTACTGTGGTTCAGCCAGTT Ch022
161 GTCTA..C..AC.AGC.................T.G...AG..C....AGAGC........GG..AT..G.CTTTAA. ChATCC
                     ChspBU7

238 GGAGTAGGAATTCCTATCGATGAGTTTGCGTGGAATCTAGGCACGGCGTCTAGGCCTAATCAAGTTTTTATATACTATTC Ch022
241 ..CAC..ATG.AAA.G.AAC....CA.ATA......T....A..AAACCT.C.C..A.GCTTT..A............G. ChATCC
        Ch022spBR1                                 ← ATspBR2

318 AAGAGTTGATGTAGGTGCAAACCGTGTAAATCTTGCTATAGTTTCAAGAAGAAGGGCTGATGAGGTTATCGTCTTGCCAC Ch022
321 T...ACC..CC.T..A..C..TA.G......T.A...T.....AGT....ATCCA........A..AT..T.A...... ChATCC
    ←

398 CGCCAACTACTGCATCAAGACCTATTATTGGTATTCGCCTTGGCAATGACGTGTTTTTTAGTGTCCATGCACTAGCTAAT Ch022
401 .T..T..G....TT........A...C.A......A.AT.AA.A......CT..C....CA.A....T..T..A.... ChATCC
                        ChspBR7

478 GGCGGTACTGATGCGCCTGCGATAGTAGAAAATGTGCATAGATTTTTCCAAAATAGACC--------TGAGATCAG-CTG Ch022
481 ..T..A.T......AT.G..T.....TC.T.G...AG...AC..C..TAG...CTC..AAACACTAA...AC..AA... ChATCC

549 GTTTATCGGCGGAGATTTTAATAGAGAACCAAATTCACTTTTGCGGCTTTGGAGCCTACGGTAAGATCAAGAGTAGATA Ch022
561 .A.AG.AATG..T.....C............GGAGAG..AC.TA.CT.A..T....TAGA.C.....CTTC.T.CTAGA. ChATCC

629 TTGTCTCACCTAGTGGAGCTACGCAAAATAGTGGTGGCA---CACTAGACTACGGTGTAGCTGGAAACTCGGCTACAACT Ch022
641 .AA.TA..AA.....CCAT...T...GT.....C.A.A.GGA.GT....T....CG....TA........TAA..G.T.. ChATCC

706 AGCTTTGTAGCTCC--TGCCAT-TGCTGCAGTTCTCATGCT----GGCAAATATGCGCTCACAGATCACATCAGAT CATG Ch022
721 GTAG..CC......AC.....CC.AT.A...C.AG..CAT.CTTTA..GG..T.A-.A.....CT.AG..AGT... ..CT ChATCC

779 TGCCTGTTAATTTTAG AAGATTTTAG Ch022
800 .T...A..CA...G.  G........A ChATCC
ComBR, ChATcomBR, cdtBcommonR

FIG. 17

SEQUENCE LISTING

```
<160> NUMBER OF SEQ ID NOS: 35

<210> SEQ ID NO 1
<211> LENGTH: 3399
<212> TYPE: DNA
<213> ORGANISM: Campylobacter hyointestinalis
<220> FEATURE:
<221> NAME/KEY: CDS
<222> LOCATION: (962)..(1600)
<220> FEATURE:
<221> NAME/KEY: CDS
<222> LOCATION: (1601)..(2422)
<220> FEATURE:
<221> NAME/KEY: CDS
<222> LOCATION: (2425)..(3177)

<400> SEQUENCE: 1
gcgtggctct cataggtcac gttctacact tttcatatag tgagattatg agtatggatg      60
tgggcgagta taatgagtat ttaaaggaag ctatggaaat tatcaaatct ttaaatgcgt     120
gtgataaatg ataaaaagcg ataaaacgca ttatttgtgc gagcaggcaa taaatcaaca     180
atgtataaaa aaagatagat aagcgtagca taaataatag atgaagcaat tatatactca     240
tcattgtttg taaatagcaa aacaataaac gaaatgatgc aaagtgcaat aaaaattgta     300
aatcttttca taggtaaatt atacaaaaaa aggataaaaa aatgcaagat atcggagtcg     360
gtcttagtat tgggttagca tttcaaggca tcgcatcaat aaaaacgtgc gaaacatcat     420
ttaataggct aaaaaaagct ataaataatg ttggaggaag tgttaaaaat ttaaaagag      480 acttggctgc aataaaaagg tatagaaaaa aaggaatata ttaaattcat atgataagct     540
gcgccacaga tagcatgaaa catcatatta tggaaagtga tttgtatgct atcaatacac     600
ccctgatggc gtgatgatca aatagtacta tatacaagga aatgagctga tatttgtatc     660
gtacaatcct atctatacat atataagatt ttttattgat gagtgtaaaa ttattggaaa     720
atttgcaggt atacttagag gggtttagag atttatttgc gtttataatc aaactatttt     780
tagtatgttt ttgaagctgt ttgattttaa aaagcgcttt acagcaatct caaaaaatta     840
ttttatctaa atttataaat atacaaaaaa ttagaatata aaaatatttt tatataaatt     900
taagtaagtt taaaatataa ttttatgac aaactttgat ttaatattta ggagtaatat      960 t atg tta agg ctt tct att ttg att atg cta tct ata ttt tta ata tct    1009
  Met Leu Arg Leu Ser Ile Leu Ile Met Leu Ser Ile Phe Leu Ile Ser
  1               5                  10                  15 tgc agt acc act aaa tca aat aac tat aaa gct cct agg gtg caa tct    1057
Cys Ser Thr Thr Lys Ser Asn Asn Tyr Lys Ala Pro Arg Val Gln Ser
```

-continued

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| act | aat | agc | aat | agc | tca | gct | cta | agc | aat | act | tta | cca | tct | aaa | cag | 1105 |
| Thr | Asn | Ser | Asn | Ser | Ser | Ala | Leu | Ser | Asn | Thr | Leu | Pro | Ser | Lys | Gln |  |
|  |  | 35 |  |  |  | 40 |  |  |  |  | 45 |  |  |  |  |  |
| ata | tta | tta | aca | act | agg | gat | aac | cta | ggg | gat | agc | tca | atg | cca | tta | 1153 |
| Ile | Leu | Leu | Thr | Thr | Arg | Asp | Asn | Leu | Gly | Asp | Ser | Ser | Met | Pro | Leu |  |
| 50 |  |  |  |  | 55 |  |  |  |  | 60 |  |  |  |  |  |  |
| gct | att | ata | aat | cca | aga | ggc | tca | tct | tta | act | gtt | tgg | gca | tta | gct | 1201 |
| Ala | Ile | Ile | Asn | Pro | Arg | Gly | Ser | Ser | Leu | Thr | Val | Trp | Ala | Leu | Ala |  |
| 65 |  |  |  |  | 70 |  |  |  |  | 75 |  |  |  |  | 80 |  |
| gag | ggt | aac | tgg | gta | tgg | gga | tat | act | cta | gat | aga | tca | ata | gat | ttt | 1249 |
| Glu | Gly | Asn | Trp | Val | Trp | Gly | Tyr | Thr | Leu | Asp | Arg | Ser | Ile | Asp | Phe |  |
|  |  |  |  | 85 |  |  |  |  | 90 |  |  |  |  | 95 |  |  |
| ggt | gga | gct | agg | cta | tgg | cag | gta | ata | aat | tta | ggc | gga | gat | ata | gct | 1297 |
| Gly | Gly | Ala | Arg | Leu | Trp | Gln | Val | Ile | Asn | Leu | Gly | Gly | Asp | Ile | Ala |  |
|  |  |  | 100 |  |  |  |  | 105 |  |  |  |  | 110 |  |  |  |
| ctt | att | aaa | aat | gtc | cgc | aca | ggt | aac | tgc | ttg | cat | gat | gaa | ggg | cgt | 1345 |
| Leu | Ile | Lys | Asn | Val | Arg | Thr | Gly | Asn | Cys | Leu | His | Asp | Glu | Gly | Arg |  |
|  |  | 115 |  |  |  |  | 120 |  |  |  |  | 125 |  |  |  |  |
| ggt | gta | act | cat | aga | act | tgc | aat | aaa | aat | agt | aaa | aac | caa | caa | tgg | 1393 |
| Gly | Val | Thr | His | Arg | Thr | Cys | Asn | Lys | Asn | Ser | Lys | Asn | Gln | Gln | Trp |  |
| 130 |  |  |  |  | 135 |  |  |  |  | 140 |  |  |  |  |  |  |
| gaa | ctt | ttt | gct | atg | gat | aat | ggt | gca | gtt | atg | att | aga | tct | act | gca | 1441 |
| Glu | Leu | Phe | Ala | Met | Asp | Asn | Gly | Ala | Val | Met | Ile | Arg | Ser | Thr | Ala |  |
| 145 |  |  |  |  | 150 |  |  |  |  | 155 |  |  |  |  | 160 |  |
| tca | aat | aat | tgc | tta | aga | aca | gag | tat | gga | gat | ata | gtc | cag | att | gat | 1489 |
| Ser | Asn | Asn | Cys | Leu | Arg | Thr | Glu | Tyr | Gly | Asp | Ile | Val | Gln | Ile | Asp |  |
|  |  |  |  | 165 |  |  |  |  | 170 |  |  |  |  | 175 |  |  |
| agt | gta | ttt | agc | att | acg | atg | gag | cga | tgc | acg | cta | gag | cca | aat | tta | 1537 |
| Ser | Val | Phe | Ser | Ile | Thr | Met | Glu | Arg | Cys | Thr | Leu | Glu | Pro | Asn | Leu |  |
|  |  |  | 180 |  |  |  |  | 185 |  |  |  |  | 190 |  |  |  |
| gat | cag | cag | tgg | ata | ttt | ata | cca | gca | cca | att | gaa | gcc | tca | ccg | ctt | 1585 |
| Asp | Gln | Gln | Trp | Ile | Phe | Ile | Pro | Ala | Pro | Ile | Glu | Ala | Ser | Pro | Leu |  |
|  |  | 195 |  |  |  |  | 200 |  |  |  |  | 205 |  |  |  |  |
| tta | gga | gat | aaa | tag | atg | aaa | aga | tta | gtt | atc | cta | gta | gcg | cta | ctt | 1633 |
| Leu | Gly | Asp | Lys |  | Met | Lys | Arg | Leu | Val | Ile | Leu | Val | Ala | Leu | Leu |  |
|  |  | 210 |  |  |  |  | 215 |  |  |  |  | 220 |  |  |  |  |
| agt | gct | agt | tta | cta | ttt | agt | gct | att | gat | gat | ttt | aaa | aca | gct | act | 1681 |
| Ser | Ala | Ser | Leu | Leu | Phe | Ser | Ala | Ile | Asp | Asp | Phe | Lys | Thr | Ala | Thr |  |
|  | 225 |  |  |  |  | 230 |  |  |  |  | 235 |  |  |  |  |  |
| tgg | aat | atg | caa | gga | tca | agc | gca | agt | agt | gaa | gct | aag | tgg | agt | gtt | 1729 |
| Trp | Asn | Met | Gln | Gly | Ser | Ser | Ala | Ser | Ser | Glu | Ala | Lys | Trp | Ser | Val |  |
| 240 |  |  |  |  | 245 |  |  |  |  | 250 |  |  |  |  | 255 |  |
| agc | ata | aga | cag | atg | ttc | tca | ggc | gat | aat | ggt | cta | gac | ata | cta | gca | 1777 |
| Ser | Ile | Arg | Gln | Met | Phe | Ser | Gly | Asp | Asn | Gly | Leu | Asp | Ile | Leu | Ala |  |
|  |  |  | 260 |  |  |  |  | 265 |  |  |  |  | 270 |  |  |  |
| gtt | caa | gaa | gca | gga | agc | ttg | cca | aga | act | gca | aga | gct | aca | ggt | agg | 1825 |
| Val | Gln | Glu | Ala | Gly | Ser | Leu | Pro | Arg | Thr | Ala | Arg | Ala | Thr | Gly | Arg |  |
|  |  | 275 |  |  |  |  | 280 |  |  |  |  | 285 |  |  |  |  |
| gta | ttt | gac | ttt | aat | ggc | aca | gat | gta | aat | gta | act | gag | cat | ata | tgg | 1873 |
| Val | Phe | Asp | Phe | Asn | Gly | Thr | Asp | Val | Asn | Val | Thr | Glu | His | Ile | Trp |  |
|  |  |  | 290 |  |  |  |  | 295 |  |  |  |  | 300 |  |  |  |
| aat | tta | gga | aca | aac | ctt | cgc | cca | agc | ttt | gta | ttt | ata | tac | tat | gct | 1921 |
| Asn | Leu | Gly | Thr | Asn | Leu | Arg | Pro | Ser | Phe | Val | Phe | Ile | Tyr | Tyr | Ala |  |
|  | 305 |  |  |  |  | 310 |  |  |  |  | 315 |  |  |  |  |  |
| aga | acc | gac | ctt | gga | gcc | aat | agg | gta | aat | tta | gct | tta | gtt | agt | aga | 1969 |
| Arg | Thr | Asp | Leu | Gly | Ala | Asn | Arg | Val | Asn | Leu | Ala | Leu | Val | Ser | Arg |  |
| 320 |  |  |  |  | 325 |  |  |  |  | 330 |  |  |  |  | 335 |  |
| aat | cca | gct | gat | gaa | gta | ttc | tta | ttg | cca | cct | cct | acg | act | gtt | tca | 2017 |
| Asn | Pro | Ala | Asp | Glu | Val | Phe | Leu | Leu | Pro | Pro | Pro | Thr | Thr | Val | Ser |  |

```
              340                 345                 350
aga cca att cta ggt att aga tta aga aat gac gct ttc ttt agc ata     2065
Arg Pro Ile Leu Gly Ile Arg Leu Arg Asn Asp Ala Phe Phe Ser Ile
        355                 360                 365 cat gct ctt gca aat ggt gga att gat gca tcg gct ata gtt cat agt     2113
His Ala Leu Ala Asn Gly Gly Ile Asp Ala Ser Ala Ile Val His Ser
370                 375                 380 gta gat aac ttc ttt aga aac tca caa aca cta atg aac tca aac tgg     2161
Val Asp Asn Phe Phe Arg Asn Ser Gln Thr Leu Met Asn Ser Asn Trp
            385                 390                 395 ata gta atg ggt gat ttc aat aga gaa cca gga gag cta ctt agc tca     2209
Ile Val Met Gly Asp Phe Asn Arg Glu Pro Gly Glu Leu Leu Ser Ser
400                 405                 410                 415 ttt gag cta gag cta aga ctt cgt gct aga ata att aca aat agt gcc     2257
Phe Glu Leu Glu Leu Arg Leu Arg Ala Arg Ile Ile Thr Asn Ser Ala
                420                 425                 430 att act caa gtt agt gct aga agg acg tta gat tac gcg gta gta gga     2305
Ile Thr Gln Val Ser Ala Arg Arg Thr Leu Asp Tyr Ala Val Val Gly
        435                 440                 445 aac tct aat aga tct gta gtt cca gct cca ctg cca cct att aca gct     2353
Asn Ser Asn Arg Ser Val Val Pro Ala Pro Leu Pro Pro Ile Thr Ala
450                 455                 460 agc aca ttc ttt agc gga ttt aga tca cac tta gca agt gat cac ttt     2401
Ser Thr Phe Phe Ser Gly Phe Arg Ser His Leu Ala Ser Asp His Phe
            465                 470                 475 cct ata aca ttt ggg aga ttt ta  atg aga act ata cta ata ttt ata     2448
Pro Ile Thr Phe Gly Arg Phe     Met Arg Thr Ile Leu Ile Phe Ile
480                 485                 490 tca tct gct ttg ttt ata atg cta agc cta agc ggt tgc gtg gat aaa     2496
Ser Ser Ala Leu Phe Ile Met Leu Ser Leu Ser Gly Cys Val Asp Lys
495                 500                 505                 510 gaa aaa gta gta tca aca act aaa agt aac ttt tta gtt act aat gag     2544
Glu Lys Val Val Ser Thr Thr Lys Ser Asn Phe Leu Val Thr Asn Glu
                515                 520                 525 agt ttg gga ttt gct ggc cca cta gca cct aat gag aat aga gct cca     2592
Ser Leu Gly Phe Ala Gly Pro Leu Ala Pro Asn Glu Asn Arg Ala Pro
        530                 535                 540 gat agg cta gat gct act cca aag gtt cct agc ata gaa aaa cta ctt     2640
Asp Arg Leu Asp Ala Thr Pro Lys Val Pro Ser Ile Glu Lys Leu Leu
545                 550                 555 aaa caa tca aat acc cca agc gat cct ttt act cct cta ctt agt cta     2688
Lys Gln Ser Asn Thr Pro Ser Asp Pro Phe Thr Pro Leu Leu Ser Leu
            560                 565                 570 aga tcg ctt gag agc ggt atg act tta ata gta aat ttc gct caa aga     2736
Arg Ser Leu Glu Ser Gly Met Thr Leu Ile Val Asn Phe Ala Gln Arg
575                 580                 585                 590 gat gag aca ttt aac tgg aat att cgt gaa gta aag tca ttt gag cca     2784
Asp Glu Thr Phe Asn Trp Asn Ile Arg Glu Val Lys Ser Phe Glu Pro
                595                 600                 605 aat ctt ata aaa aat att caa aga gta gat gat ttt aag tat ctt gag     2832
Asn Leu Ile Lys Asn Ile Gln Arg Val Asp Asp Phe Lys Tyr Leu Glu
        610                 615                 620 ttt gag tat att cag ttt gta agt tct aat gac att gat atg tgc tta     2880
Phe Glu Tyr Ile Gln Phe Val Ser Ser Asn Asp Ile Asp Met Cys Leu
625                 630                 635 gcc ata caa gaa agt gga ttt ttt ggg cta aaa aat tgt gct gat gat     2928
Ala Ile Gln Glu Ser Gly Phe Phe Gly Leu Lys Asn Cys Ala Asp Asp
640                 645                 650 ctt gaa aaa gct aag ttt gag agt gta ttt caa cta atc cct atg agt     2976
Leu Glu Lys Ala Lys Phe Glu Ser Val Phe Gln Leu Ile Pro Met Ser
```

-continued

```
                655                 660                 665                 670
aca gac tca gtc cag att aga tca ttg gtg ctt ggt gga ggc gaa tgt       3024
Thr Asp Ser Val Gln Ile Arg Ser Leu Val Leu Gly Gly Gly Glu Cys
                675                 680                 685 ata agc aca ttt gaa aat ccc aat ctt ttc cca tgg caa cga ata ggt       3072
Ile Ser Thr Phe Glu Asn Pro Asn Leu Phe Pro Trp Gln Arg Ile Gly
                690                 695                 700 ata gat aag tgt caa cta atg caa ggt ttt aat aca aac cta gca aga       3120
Ile Asp Lys Cys Gln Leu Met Gln Gly Phe Asn Thr Asn Leu Ala Arg
                705                 710                 715 ctt tgg gct ata atg cca gaa aat aga cct gct aag gtg ctg gtg tct       3168
Leu Trp Ala Ile Met Pro Glu Asn Arg Pro Ala Lys Val Leu Val Ser
                720                 725                 730 gtg aag tga tgaagatgag caaaactaag ttttaaatga tgaagtattt              3217
Val Lys
735 gtagcaccaa atgtgtcaaa aataatatat tttgttttaa agactaaatt tgctaccaaa     3277 aataacactg atctaaagtt ttttataaaa tagtaattta tagattacta ttaaacaatg     3337 tttatatgtt aagctcaata caaatcatat aaatttagac aagtaaagtg cggctaacac     3397 aa                                                                    3399

<210> SEQ ID NO 2
<211> LENGTH: 212
<212> TYPE: PRT
<213> ORGANISM: Campylobacter hyointestinalis

<400> SEQUENCE: 2

Met Leu Arg Leu Ser Ile Leu Ile Met Leu Ser Ile Phe Leu Ile Ser
1               5                   10                  15

Cys Ser Thr Thr Lys Ser Asn Asn Tyr Lys Ala Pro Arg Val Gln Ser
                20                  25                  30

Thr Asn Ser Asn Ser Ser Ala Leu Ser Asn Thr Leu Pro Ser Lys Gln
            35                  40                  45

Ile Leu Leu Thr Thr Arg Asp Asn Leu Gly Asp Ser Ser Met Pro Leu
        50                  55                  60

Ala Ile Ile Asn Pro Arg Gly Ser Ser Leu Thr Val Trp Ala Leu Ala
65                  70                  75                  80

Glu Gly Asn Trp Val Trp Gly Tyr Thr Leu Asp Arg Ser Ile Asp Phe
                85                  90                  95

Gly Gly Ala Arg Leu Trp Gln Val Ile Asn Leu Gly Gly Asp Ile Ala
            100                 105                 110

Leu Ile Lys Asn Val Arg Thr Gly Asn Cys Leu His Asp Glu Gly Arg
        115                 120                 125

Gly Val Thr His Arg Thr Cys Asn Lys Asn Ser Lys Asn Gln Gln Trp
    130                 135                 140

Glu Leu Phe Ala Met Asp Asn Gly Ala Val Met Ile Arg Ser Thr Ala
145                 150                 155                 160

Ser Asn Asn Cys Leu Arg Thr Glu Tyr Gly Asp Ile Val Gln Ile Asp
                165                 170                 175

Ser Val Phe Ser Ile Thr Met Glu Arg Cys Thr Leu Glu Pro Asn Leu
            180                 185                 190

Asp Gln Gln Trp Ile Phe Ile Pro Ala Pro Ile Glu Ala Ser Pro Leu
        195                 200                 205

Leu Gly Asp Lys
    210
```

-continued

```
<210> SEQ ID NO 3
<211> LENGTH: 274
<212> TYPE: PRT
<213> ORGANISM: Campylobacter hyointestinalis

<400> SEQUENCE: 3

Met Lys Arg Leu Val Ile Leu Val Ala Leu Leu Ser Ala Ser Leu Leu
1               5                   10                  15

Phe Ser Ala Ile Asp Asp Phe Lys Thr Ala Thr Trp Asn Met Gln Gly
            20                  25                  30

Ser Ser Ala Ser Ser Glu Ala Lys Trp Ser Val Ser Ile Arg Gln Met
        35                  40                  45

Phe Ser Gly Asp Asn Gly Leu Asp Ile Leu Ala Val Gln Glu Ala Gly
    50                  55                  60

Ser Leu Pro Arg Thr Ala Arg Ala Thr Gly Arg Val Phe Asp Phe Asn
65                  70                  75                  80

Gly Thr Asp Val Asn Val Thr Glu His Ile Trp Asn Leu Gly Thr Asn
                85                  90                  95

Leu Arg Pro Ser Phe Val Phe Ile Tyr Tyr Ala Arg Thr Asp Leu Gly
            100                 105                 110

Ala Asn Arg Val Asn Leu Ala Leu Val Ser Arg Asn Pro Ala Asp Glu
        115                 120                 125

Val Phe Leu Leu Pro Pro Thr Thr Val Ser Arg Pro Ile Leu Gly
    130                 135                 140

Ile Arg Leu Arg Asn Asp Ala Phe Phe Ser Ile His Ala Leu Ala Asn
145                 150                 155                 160

Gly Gly Ile Asp Ala Ser Ala Ile Val His Ser Val Asp Asn Phe Phe
                165                 170                 175

Arg Asn Ser Gln Thr Leu Met Asn Ser Asn Trp Ile Val Met Gly Asp
            180                 185                 190

Phe Asn Arg Glu Pro Gly Glu Leu Leu Ser Ser Phe Glu Leu Glu Leu
        195                 200                 205

Arg Leu Arg Ala Arg Ile Ile Thr Asn Ser Ala Ile Thr Gln Val Ser
    210                 215                 220

Ala Arg Arg Thr Leu Asp Tyr Ala Val Val Gly Asn Ser Asn Arg Ser
225                 230                 235                 240

Val Val Pro Ala Pro Leu Pro Pro Ile Thr Ala Ser Thr Phe Phe Ser
                245                 250                 255

Gly Phe Arg Ser His Leu Ala Ser Asp His Phe Pro Thr Phe Gly
            260                 265                 270

Arg Phe

<210> SEQ ID NO 4
<211> LENGTH: 250
<212> TYPE: PRT
<213> ORGANISM: Campylobacter hyointestinalis

<400> SEQUENCE: 4

Met Arg Thr Ile Leu Ile Phe Ile Ser Ser Ala Leu Phe Ile Met Leu
1               5                   10                  15

Ser Leu Ser Gly Cys Val Asp Lys Glu Lys Val Val Ser Thr Thr Lys
            20                  25                  30

Ser Asn Phe Leu Val Thr Asn Glu Ser Leu Gly Phe Ala Gly Pro Leu
        35                  40                  45

Ala Pro Asn Glu Asn Arg Ala Pro Asp Arg Leu Asp Ala Thr Pro Lys
    50                  55                  60
```

```
Val Pro Ser Ile Glu Lys Leu Leu Lys Gln Ser Asn Thr Pro Ser Asp
 65                  70                  75                  80

Pro Phe Thr Pro Leu Leu Ser Leu Arg Ser Leu Glu Ser Gly Met Thr
                 85                  90                  95

Leu Ile Val Asn Phe Ala Gln Arg Asp Glu Thr Phe Asn Trp Asn Ile
            100                 105                 110

Arg Glu Val Lys Ser Phe Glu Pro Asn Leu Ile Lys Asn Ile Gln Arg
        115                 120                 125

Val Asp Asp Phe Lys Tyr Leu Glu Phe Glu Tyr Ile Gln Phe Val Ser
    130                 135                 140

Ser Asn Asp Ile Asp Met Cys Leu Ala Ile Gln Glu Ser Gly Phe Phe
145                 150                 155                 160

Gly Leu Lys Asn Cys Ala Asp Asp Leu Glu Lys Ala Lys Phe Glu Ser
                165                 170                 175

Val Phe Gln Leu Ile Pro Met Ser Thr Asp Ser Val Gln Ile Arg Ser
            180                 185                 190

Leu Val Leu Gly Gly Gly Glu Cys Ile Ser Thr Phe Glu Asn Pro Asn
        195                 200                 205

Leu Phe Pro Trp Gln Arg Ile Gly Ile Asp Lys Cys Gln Leu Met Gln
    210                 215                 220

Gly Phe Asn Thr Asn Leu Ala Arg Leu Trp Ala Ile Met Pro Glu Asn
225                 230                 235                 240

Arg Pro Ala Lys Val Leu Val Ser Val Lys
                245                 250

<210> SEQ ID NO 5
<211> LENGTH: 4069
<212> TYPE: DNA
<213> ORGANISM: Campylobacter hyointestinalis
<220> FEATURE:
<221> NAME/KEY: CDS
<222> LOCATION: (1059)..(1835)
<220> FEATURE:
<221> NAME/KEY: CDS
<222> LOCATION: (1853)..(2656)
<220> FEATURE:
<221> NAME/KEY: CDS
<222> LOCATION: (2666)..(3202)

<400> SEQUENCE: 5
aggtacaaag caaaacttgg tcttttgaaa gtacggcgat atttggcctt tgagtttgat      60
acaaataggt ggttttttca agtataatc ctttttataat gcttctatcg tgcgtagaaa     120
aatttgctat caaaaaatca gatatagtgg tttccaattt aaaaaattat tcaaagcata    180
ttaaagattt gggtattcaa aaacaagcat attggatctc gaatggtata aatttgagag    240
atatggatat gcaagaagaa ttgccacaac atataaaagg tcttgtgcca aaggataaat    300
ttataatagg ctataccgga aaattgggtg tatcaaattc gatcatatat ctattaaaag    360
cggcacgcat attgcaaaat aacactaata taaaatttat tatagttggt gatggacaag    420
agaaacaagc tttggtagac tatgcaagtg atctaaataa tgttattttt atagatccga    480
taccaaaatc aaatatccaa tcaatgctta gcttatttga tgtgtgttac ataggatggc    540
tagacaaaga actatataaa tttggcatag cggcaaataa gttatttgat tatatgtata    600
gttgtaaacc aatcttacac tctataaata catcagatag tatagtaaat atggtcgggt    660
ttggatgtgg tataaaaata aattcagaag atccagaagc catagcggaa gctaaaacgg    720
aactgtacgc gacaccaaaa aatctaatga aaaaaatggg ggaaaatggt aaaaaggcta    780
```

-continued

```
tcctagatca atttacatac catgaattgg ctaaaaaata tttgaaaatc atataaattt    840
ttatatttat aagataaatg atgatcttat cgagctaatc atagaatata taagataca     900 ttgtttgttg aattttttcat cttaatatcc tgagtttatc catattttac aagttctatc   960 agattttta  ggaattttga taataaaaat tattctgtta attaatcata aataaattct   1020
cattagaatg atataaataa actttaaaag aatcaata atg aaa tac ata gca tac   1076
                                          Met Lys Tyr Ile Ala Tyr
                                           1               5 cta gct ttt ata agc tta ctc ctt gtt ggt tgc tct agc aaa gcc aca    1124
Leu Ala Phe Ile Ser Leu Leu Leu Val Gly Cys Ser Ser Lys Ala Thr
         10                  15                  20 tat att aac tat tta gca aaa tat gga ggc gat cca acc gac acc gat    1172
Tyr Ile Asn Tyr Leu Ala Lys Tyr Gly Gly Asp Pro Thr Asp Thr Asp
     25                  30                  35 cca cta agg ctc ggt tca aac cca aaa gag ccg gcg att caa aaa ata    1220
Pro Leu Arg Leu Gly Ser Asn Pro Lys Glu Pro Ala Ile Gln Lys Ile
 40                  45                  50 cca gca cta ctt atc ggt gaa aat aaa ttt ttt aag caa aat tta cct    1268
Pro Ala Leu Leu Ile Gly Glu Asn Lys Phe Phe Lys Gln Asn Leu Pro
55                  60                  65                  70 aca ttt agc gga acg cta caa agt gat cca gtc cac ggt cca aac gaa    1316
Thr Phe Ser Gly Thr Leu Gln Ser Asp Pro Val His Gly Pro Asn Glu
                 75                  80                  85 cgt gat cca gac aat cca ttt gat gat aca aag gtt ttt tac aac act    1364
Arg Asp Pro Asp Asn Pro Phe Asp Asp Thr Lys Val Phe Tyr Asn Thr
             90                  95                 100 cca cag ata tct gag ttc gtt tct att gta gct cac aac gat gcc ctt    1412
Pro Gln Ile Ser Glu Phe Val Ser Ile Val Ala His Asn Asp Ala Leu
             105                 110                 115 atg acc att tgg gct ttg gct tat ggt aac tgg gta tgg gcc tac tcg    1460
Met Thr Ile Trp Ala Leu Ala Tyr Gly Asn Trp Val Trp Ala Tyr Ser
         120                 125                 130 gca act gat agt atg agt ttt ggt gat gcg aga ata tgg aag ctt gtc    1508
Ala Thr Asp Ser Met Ser Phe Gly Asp Ala Arg Ile Trp Lys Leu Val
135                 140                 145                 150 ata tat cca aaa aat ttc gtc caa atc caa aac aaa atg acc ggc act    1556
Ile Tyr Pro Lys Asn Phe Val Gln Ile Gln Asn Lys Met Thr Gly Thr
                 155                 160                 165 tgt ctt agt gcc tat caa aat ggc gtt gta cac tat cct tgt gat gat    1604
Cys Leu Ser Ala Tyr Gln Asn Gly Val Val His Tyr Pro Cys Asp Asp
             170                 175                 180 aca aac caa gct cag ttc tgg caa tta aat cag ttt gca aac gga gcc    1652
Thr Asn Gln Ala Gln Phe Trp Gln Leu Asn Gln Phe Ala Asn Gly Ala
             185                 190                 195 gta cag ctc caa aat ttc gct tcc aaa gag tgt ttg tct act gac cct    1700
Val Gln Leu Gln Asn Phe Ala Ser Lys Glu Cys Leu Ser Thr Asp Pro
         200                 205                 210 aca aag gga agt agc tat tat ggt ata tat gct gta agg tgt ata aat    1748
Thr Lys Gly Ser Ser Tyr Tyr Gly Ile Tyr Ala Val Arg Cys Ile Asn
215                 220                 225                 230 gca ggc gag aag gcg ctt tct cag cag tgg ata atc tca gca ccg ttt    1796
Ala Gly Glu Lys Ala Leu Ser Gln Gln Trp Ile Ile Ser Ala Pro Phe
                 235                 240                 245 gta gaa act ccg cct ata aaa atg cca gat ccg att ctt ggtcaaggag     1845
Val Glu Thr Pro Pro Ile Lys Met Pro Asp Pro Ile Leu
                 250                 255 gtgagat atg aag aaa ttt ctt ata gtt tta ttg ctt tgt ttt agt act    1894
        Met Lys Lys Phe Leu Ile Val Leu Leu Leu Cys Phe Ser Thr
         260                 265                 270
```

```
cta cta gca aat att gaa gat tac agc atc gct act tgg aat atg caa    1942
Leu Leu Ala Asn Ile Glu Asp Tyr Ser Ile Ala Thr Trp Asn Met Gln
    275                 280                 285 ggc tca tct gct gca acc gaa agc aaa tgg aat gtc aat atc aga caa    1990
Gly Ser Ser Ala Ala Thr Glu Ser Lys Trp Asn Val Asn Ile Arg Gln
290                 295                 300                 305 cta ata tca ggc aat agc gca gct gat att ttg cta gtt caa gaa gca    2038
Leu Ile Ser Gly Asn Ser Ala Ala Asp Ile Leu Leu Val Gln Glu Ala
            310                 315                 320 gga agc ata cca gta agt gca gtt tat aca ggt act gtg gtt cag cca    2086
Gly Ser Ile Pro Val Ser Ala Val Tyr Thr Gly Thr Val Val Gln Pro
                325                 330                 335 gtt gga gta gga att cct atc gat gag ttt gcg tgg aat cta ggc acg    2134
Val Gly Val Gly Ile Pro Ile Asp Glu Phe Ala Trp Asn Leu Gly Thr
            340                 345                 350 gcg tct agg cct aat caa gtt ttt ata tac tat tca aga gtt gat gta    2182
Ala Ser Arg Pro Asn Gln Val Phe Ile Tyr Tyr Ser Arg Val Asp Val
    355                 360                 365 ggt gca aac cgt gta aat ctt gct ata gtt tca aga aga agg gct gat    2230
Gly Ala Asn Arg Val Asn Leu Ala Ile Val Ser Arg Arg Arg Ala Asp
370                 375                 380                 385 gag gtt atc gtc ttg cca ccg cca act act gca tca aga cct att att    2278
Glu Val Ile Val Leu Pro Pro Pro Thr Thr Ala Ser Arg Pro Ile Ile
            390                 395                 400 ggt att cgc ctt ggc aat gac gtg ttt ttt agt gtg cat gca cta gct    2326
Gly Ile Arg Leu Gly Asn Asp Val Phe Phe Ser Val His Ala Leu Ala
                405                 410                 415 aat ggc ggt act gat gcg cct gcg ata gta gaa aat gtg cat aga ttt    2374
Asn Gly Gly Thr Asp Ala Pro Ala Ile Val Glu Asn Val His Arg Phe
            420                 425                 430 ttc caa aat aga cct gag atc agc tgg ttt atc ggc gga gat ttt aat    2422
Phe Gln Asn Arg Pro Glu Ile Ser Trp Phe Ile Gly Gly Asp Phe Asn
    435                 440                 445 aga gaa cca aat tca ctt ttg cgg gct ttg gag cct acg gta aga tca    2470
Arg Glu Pro Asn Ser Leu Leu Arg Ala Leu Glu Pro Thr Val Arg Ser
450                 455                 460                 465 aga gta gat att gtc tca cct agt gga gct acg caa aat agt ggt ggc    2518
Arg Val Asp Ile Val Ser Pro Ser Gly Ala Thr Gln Asn Ser Gly Gly
            470                 475                 480 aca cta gac tac ggt gta gct gga aac tcg gct aca act agc ttt gta    2566
Thr Leu Asp Tyr Gly Val Ala Gly Asn Ser Ala Thr Thr Ser Phe Val
                485                 490                 495 gct cct gcc att gct gca gtt ctc atg ctg gca aat atg cgc tca cag    2614
Ala Pro Ala Ile Ala Ala Val Leu Met Leu Ala Asn Met Arg Ser Gln
            500                 505                 510 atc aca tca gat cat gtg cct gtt aat ttt aga aga ttt tag gagacacat 2665
Ile Thr Ser Asp His Val Pro Val Asn Phe Arg Arg Phe
    515                 520                 525 atg aaa aca ttt att aaa ata tta cta ctt att tca tta gct att cca    2713
Met Lys Thr Phe Ile Lys Ile Leu Leu Leu Ile Ser Leu Ala Ile Pro
530                 535                 540 agt ttt gga ttt gaa gat gac aat gtt atg ccg tta gtt tca tta aga    2761
Ser Phe Gly Phe Glu Asp Asp Asn Val Met Pro Leu Val Ser Leu Arg
            545                 550                 555 agt cta aaa act ggt att ttg ata gcg tat gaa gac aat gcg cca aat    2809
Ser Leu Lys Thr Gly Ile Leu Ile Ala Tyr Glu Asp Asn Ala Pro Asn
                560                 565                 570 ttg ttt gat aga aac tgg cgt atc aaa gag gta att ttg cct ttc gag    2857
Leu Phe Asp Arg Asn Trp Arg Ile Lys Glu Val Ile Leu Pro Phe Glu
    575                 580                 585                 590
```

```
ata aga aag cat tat ccg ttt ggt aat gtg caa ttt atg cat cca acc    2905
Ile Arg Lys His Tyr Pro Phe Gly Asn Val Gln Phe Met His Pro Thr
    595                 600                 605 aaa acc gat att tgc tta ggc tta gat ggt gct aag cta acg acc atg    2953
Lys Thr Asp Ile Cys Leu Gly Leu Asp Gly Ala Lys Leu Thr Thr Met
610                 615                 620 gag tgt aat ctt ata aat atc ggt gat ttt agg act gct ttt tcg ctt    3001
Glu Cys Asn Leu Ile Asn Ile Gly Asp Phe Arg Thr Ala Phe Ser Leu
                625                 630                 635 ctt ccg acc gca act tca gca gtg cag atc aag gcg gta aat gac cta    3049
Leu Pro Thr Ala Thr Ser Ala Val Gln Ile Lys Ala Val Asn Asp Leu
            640                 645                 650 aac gaa tgc ctt agc ata gga cca agt act agc gga acg tct ttt tca    3097
Asn Glu Cys Leu Ser Ile Gly Pro Ser Thr Ser Gly Thr Ser Phe Ser
        655                 660                 665          670 agg atg gga ctt aga agc tgt gag atg gac gag aag tca aac atc atc    3145
Arg Met Gly Leu Arg Ser Cys Glu Met Asp Glu Lys Ser Asn Ile Ile
    675                 680                 685 tta gaa aat tta ttt gtc cta tct gtg cct att ttg gat tca aaa tta    3193
Leu Glu Asn Leu Phe Val Leu Ser Val Pro Ile Leu Asp Ser Lys Leu
690                 695                 700 gta aag taa gattaaaagt cgttttttaga cggctcaaat tccctttttt           3242
Val Lys cctagtacga ctacaatagt cttgtagatg actttaagct ctagccaaag cgaccagtgt  3302
ttgatgtagt agagatcata cattagcttt tgttttgcat catcagtatt gcgccgtat  3362 gggtacatga cttgcgccca gcctgtgatg cctggtttta tgatatgtcg ttcgcagtag  3422
tatgggatct cttgttcgta gcctttgacg agtatatccc actctgctct tggtccgatg  3482
agatgcatct ctcctcttaa cacgtttaaa atttgcggaa gctcatcgat ccttgttttt  3542
ctcatgaatt tgccaaaagg ataaattcta tcgtcttctt ttttggtgta tggatcatga  3602
taactatttt cgtgcatggt acgaaatttt atacatttaa atatatcacc gttttacca   3662 actctatctt gtttaaaata tagacttcct ggagattggg cttttatctt gcttttact   3722 ataaaaacca gcggccacat agttagcagc aagattccag caccaattat atcgactatc  3782
tttttttgca atagttgcca tggactaaac ggcttgattt tgcttaaaaa cgcaagatca  3842
ctattatcac caggaatata acatttgttt agatatttct ccataaaatc ttcgatagtt  3902
atgatcttta aaggcttttt tctttttga  aattgtaaag tcgttagata ttttattata   3962
ttgctaccaa cagttgcagt cgtatttaaa accaaagtgt caaaatactc ttctcctgct  4022
atgctttgta gctctcctag aacctcatct tctgatctgt tgcgaat              4069
```

<210> SEQ ID NO 6
<211> LENGTH: 259
<212> TYPE: PRT
<213> ORGANISM: Campylobacter hyointestinalis

<400> SEQUENCE: 6

Met Lys Tyr Ile Ala Tyr Leu Ala Phe Ile Ser Leu Leu Val Gly
1               5                   10                  15

Cys Ser Ser Lys Ala Thr Tyr Ile Asn Tyr Leu Ala Lys Tyr Gly Gly
                20                  25                  30

Asp Pro Thr Asp Thr Asp Pro Leu Arg Leu Gly Ser Asn Pro Lys Glu
            35                  40                  45

Pro Ala Ile Gln Lys Ile Pro Ala Leu Leu Ile Gly Glu Asn Lys Phe
        50                  55                  60

Phe Lys Gln Asn Leu Pro Thr Phe Ser Gly Thr Leu Gln Ser Asp Pro

```
               65                  70                  75                  80
Val His Gly Pro Asn Glu Arg Asp Pro Asp Asn Pro Phe Asp Asp Thr
                    85                  90                  95

Lys Val Phe Tyr Asn Thr Pro Gln Ile Ser Glu Phe Val Ser Ile Val
                100                 105                 110

Ala His Asn Asp Ala Leu Met Thr Ile Trp Ala Leu Ala Tyr Gly Asn
                115                 120                 125

Trp Val Trp Ala Tyr Ser Ala Thr Asp Ser Met Ser Phe Gly Asp Ala
            130                 135                 140

Arg Ile Trp Lys Leu Val Ile Tyr Pro Lys Asn Phe Val Gln Ile Gln
145                 150                 155                 160

Asn Lys Met Thr Gly Thr Cys Leu Ser Ala Tyr Gln Asn Gly Val Val
                165                 170                 175

His Tyr Pro Cys Asp Asp Thr Asn Gln Ala Gln Phe Trp Gln Leu Asn
                180                 185                 190

Gln Phe Ala Asn Gly Ala Val Gln Leu Gln Asn Phe Ala Ser Lys Glu
            195                 200                 205

Cys Leu Ser Thr Asp Pro Thr Lys Gly Ser Ser Tyr Tyr Gly Ile Tyr
            210                 215                 220

Ala Val Arg Cys Ile Asn Ala Gly Glu Lys Ala Leu Ser Gln Gln Trp
225                 230                 235                 240

Ile Ile Ser Ala Pro Phe Val Glu Thr Pro Pro Ile Lys Met Pro Asp
                245                 250                 255

Pro Ile Leu

<210> SEQ ID NO 7
<211> LENGTH: 267
<212> TYPE: PRT
<213> ORGANISM: Campylobacter hyointestinalis

<400> SEQUENCE: 7

Met Lys Lys Phe Leu Ile Val Leu Leu Leu Cys Phe Ser Thr Leu Leu
1               5                   10                  15

Ala Asn Ile Glu Asp Tyr Ser Ile Ala Thr Trp Asn Met Gln Gly Ser
                20                  25                  30

Ser Ala Ala Thr Glu Ser Lys Trp Asn Val Asn Ile Arg Gln Leu Ile
            35                  40                  45

Ser Gly Asn Ser Ala Ala Asp Ile Leu Leu Val Gln Glu Ala Gly Ser
        50                  55                  60

Ile Pro Val Ser Ala Val Tyr Thr Gly Thr Val Gln Pro Val Gly
65                  70                  75                  80

Val Gly Ile Pro Ile Asp Glu Phe Ala Trp Asn Leu Gly Thr Ala Ser
                85                  90                  95

Arg Pro Asn Gln Val Phe Ile Tyr Tyr Ser Arg Val Asp Val Gly Ala
                100                 105                 110

Asn Arg Val Asn Leu Ala Ile Val Ser Arg Arg Ala Asp Glu Val
            115                 120                 125

Ile Val Leu Pro Pro Thr Thr Ala Ser Arg Pro Ile Ile Gly Ile
            130                 135                 140

Arg Leu Gly Asn Asp Val Phe Phe Ser Val His Ala Leu Ala Asn Gly
145                 150                 155                 160

Gly Thr Asp Ala Pro Ala Ile Val Glu Asn Val His Arg Phe Phe Gln
                165                 170                 175

Asn Arg Pro Glu Ile Ser Trp Phe Ile Gly Gly Asp Phe Asn Arg Glu
                180                 185                 190
```

```
Pro Asn Ser Leu Leu Arg Ala Leu Glu Pro Thr Val Arg Ser Arg Val
        195                 200                 205

Asp Ile Val Ser Pro Ser Gly Ala Thr Gln Asn Ser Gly Gly Thr Leu
        210                 215                 220

Asp Tyr Gly Val Ala Gly Asn Ser Ala Thr Thr Ser Phe Val Ala Pro
225                 230                 235                 240

Ala Ile Ala Ala Val Leu Met Leu Ala Asn Met Arg Ser Gln Ile Thr
                245                 250                 255

Ser Asp His Val Pro Val Asn Phe Arg Arg Phe
        260                 265

<210> SEQ ID NO 8
<211> LENGTH: 178
<212> TYPE: PRT
<213> ORGANISM: Campylobacter hyointestinalis

<400> SEQUENCE: 8

Met Lys Thr Phe Ile Lys Ile Leu Leu Ile Ser Leu Ala Ile Pro
1               5                   10                  15

Ser Phe Gly Phe Glu Asp Asp Asn Val Met Pro Leu Val Ser Leu Arg
                20                  25                  30

Ser Leu Lys Thr Gly Ile Leu Ile Ala Tyr Glu Asp Asn Ala Pro Asn
            35                  40                  45

Leu Phe Asp Arg Asn Trp Arg Ile Lys Glu Val Ile Leu Pro Phe Glu
        50                  55                  60

Ile Arg Lys His Tyr Pro Phe Gly Asn Val Gln Phe Met His Pro Thr
65                  70                  75                  80

Lys Thr Asp Ile Cys Leu Gly Leu Asp Gly Ala Lys Leu Thr Thr Met
                85                  90                  95

Glu Cys Asn Leu Ile Asn Ile Gly Asp Phe Arg Thr Ala Phe Ser Leu
                100                 105                 110

Leu Pro Thr Ala Thr Ser Ala Val Gln Ile Lys Ala Val Asn Asp Leu
            115                 120                 125

Asn Glu Cys Leu Ser Ile Gly Pro Ser Thr Ser Gly Thr Ser Phe Ser
        130                 135                 140

Arg Met Gly Leu Arg Ser Cys Glu Met Asp Glu Lys Ser Asn Ile Ile
145                 150                 155                 160

Leu Glu Asn Leu Phe Val Leu Ser Val Pro Ile Leu Asp Ser Lys Leu
                165                 170                 175

Val Lys

<210> SEQ ID NO 9
<211> LENGTH: 265
<212> TYPE: PRT
<213> ORGANISM: Campylobacter jejuni

<400> SEQUENCE: 9

Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
                20                  25                  30

Ala Ala Thr Glu Ser Lys Trp Ser Val Ser Val Arg Gln Leu Val Ser
            35                  40                  45

Gly Ala Asn Pro Leu Asp Ile Leu Met Ile Gln Glu Ala Gly Thr Leu
        50                  55                  60

Pro Arg Thr Ala Thr Pro Thr Gly Arg His Val Gln Gln Gly Gly Thr
```

```
              65                  70                  75                  80
Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Val Ile Val Leu
        115                 120                 125

Pro Pro Pro Thr Thr Val Ser Arg Pro Ile Ile Gly Ile Arg Asn Gly
        130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
            260                 265

<210> SEQ ID NO 10
<211> LENGTH: 267
<212> TYPE: PRT
<213> ORGANISM: Campylobacter coli

<400> SEQUENCE: 10

Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30

Ala Ala Thr Glu Ser Lys Trp Asn Val Ser Ile Arg Gln Leu Ile Thr
        35                  40                  45

Gly Ala Asn Pro Met Asp Val Leu Ala Val Gln Glu Ala Gly Val Leu
    50                  55                  60

Pro Ser Thr Ala Met Met Thr Pro Arg Gln Val Gln Pro Val Gly Val
65                  70                  75                  80

Gly Ile Pro Ile His Glu Tyr Ile Trp Asn Leu Gly Ser Val Ser Arg
                85                  90                  95

Pro Ser Ser Val Tyr Ile Tyr Tyr Ser Arg Val Asp Val Gly Ala Asn
            100                 105                 110

Arg Val Asn Leu Ala Ile Val Ser Arg Val Gln Ala Asp Glu Val Phe
        115                 120                 125

Val Leu Pro Pro Pro Thr Val Ala Ser Arg Pro Ile Ile Gly Ile Arg
    130                 135                 140

Ile Gly Asn Asp Ala Phe Phe Asn Ile His Ala Leu Ala Ser Gly Gly
145                 150                 155                 160

Asn Asp Ala Gly Ala Ile Val Ala Ala Val Asp Met Phe Phe Arg Asn
                165                 170                 175

Arg Pro Asp Ile Asn Trp Met Ile Leu Gly Asp Phe Asn Arg Glu Ser
```

```
                 180                 185                 190
Gly Ala Leu Val Thr Leu Leu Asp Pro Asp Leu Arg Ala Arg Thr Arg
        195                 200                 205

Val Val Val Pro Pro Ser Ser Thr Gln Thr Ser Gly Arg Thr Ile Asp
210                 215                 220

Tyr Ala Ile Thr Gly Asn Ser Asn Thr Ala Ala Leu Tyr Asn Pro Pro
225                 230                 235                 240

Pro Ile Val Ala Ile Leu Ala Leu Glu Gly Leu Arg Thr Phe Leu Ala
            245                 250                 255

Ser Asp His Phe Pro Val Asn Phe Arg Arg Pro
            260                 265

<210> SEQ ID NO 11
<211> LENGTH: 266
<212> TYPE: PRT
<213> ORGANISM: Campylobacter fetus

<400> SEQUENCE: 11

Met Arg Asn Val Ile Met Ile Ile Phe Ile Ala Thr Leu Gly Phe Ala
1               5                   10                  15

Lys Pro Glu Asp Tyr Lys Ile Ala Thr Trp Asn Leu Gln Gly Ser Ser
            20                  25                  30

Ala Ile Thr Glu Ser Lys Trp Asn Ile Ser Val Arg Gln Ile Ile Ser
        35                  40                  45

Gly Glu Asn Pro Ala Asp Ile Leu Ala Val Gln Glu Ala Gly Asn Leu
    50                  55                  60

Pro Gln Thr Ala Leu Pro Thr Gly Arg Ser Ile Asn Gln Gly Gly Thr
65                  70                  75                  80

Ile Val Thr Glu His Leu Trp Gln Leu Gly Ser Ile Ser Arg Pro Phe
                85                  90                  95

Gln Val Tyr Ile Tyr Tyr Ala Gln Ile Asp Thr Gly Ala Asn Arg Val
            100                 105                 110

Asn Leu Ala Ile Val Ser Arg Ile Lys Ala Asp Glu Ile Ile Ile Leu
        115                 120                 125

Pro Pro Pro Thr Val Ala Ser Arg Pro Leu Ile Gly Ile Arg Ile Gly
    130                 135                 140

Asn Asp Val Phe Phe Asn Ile His Ala Leu Ala Asn Gly Gly Val Asp
145                 150                 155                 160

Ala Pro Ala Ile Ile Asn Ser Ile Phe Asp Arg Phe Arg Asn Met Pro
                165                 170                 175

Asn Ile Thr Trp Met Ile Leu Gly Asp Phe Asn Arg Ser Pro Glu Ser
            180                 185                 190

Leu Arg Gly Thr Leu Gly Leu Glu Thr Arg Val Arg Val Thr Phe Leu
        195                 200                 205

Thr Pro Pro Ala Pro Thr Gln Arg Ser Gly Gly Thr Leu Asp Trp Ala
    210                 215                 220

Ile Val Gly Asn Ser Ala Gly Asp Leu Val Arg Thr Thr Leu Val Ala
225                 230                 235                 240

Val Leu Met Leu Ala Asn Leu Arg Thr His Leu Val Ser Asp His Phe
                245                 250                 255

Pro Val Asn Phe Arg Lys Phe Gly Asp Asn
            260                 265

<210> SEQ ID NO 12
<211> LENGTH: 18
<212> TYPE: DNA
```

-continued

<213> ORGANISM: Campylobacter jejuni

<400> SEQUENCE: 12
acttggaatt tgcaaggc                                                 18

<210> SEQ ID NO 13
<211> LENGTH: 20
<212> TYPE: DNA
<213> ORGANISM: Campylobacter jejuni

<400> SEQUENCE: 13
cattttccag taaattttag                                               20

<210> SEQ ID NO 14
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 14
acttggaatt tgcaaggc                                                 18

<210> SEQ ID NO 15
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 15
tctaaaattt achggaaaat g                                             21

<210> SEQ ID NO 16
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 16
acttggaata tgcaagga                                                 18

<210> SEQ ID NO 17
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 17
ccaaatgtta taggaaagtg                                               20

<210> SEQ ID NO 18
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 18
acttggaatw tgcaaggm                                                 18

<210> SEQ ID NO 19
<211> LENGTH: 20
<212> TYPE: DNA

<213> ORGANISM: Artificial
<220> FEATURE:
<223> OTHER INFORMATION: An artificially synthesized primer sequence

<400> SEQUENCE: 19
cyaaawktta yhggaaartg                                                20

<210> SEQ ID NO 20
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 20
tatcaggcaa tagcgcag                                                  18

<210> SEQ ID NO 21
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 21
ggtttgcacc tacatcaac                                                 19

<210> SEQ ID NO 22
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 22
cctagtagcg ctacttag                                                  18

<210> SEQ ID NO 23
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 23
tacaaagctt gggcgaag                                                  18

<210> SEQ ID NO 24
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 24
gttcaagaag caggaagc                                                  18

<210> SEQ ID NO 25
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 25
aataccwaka atwggtcttg                                                20

```
<210> SEQ ID NO 26
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 26
atcttttaac cttgcttttg c                                              21

<210> SEQ ID NO 27
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 27
gcaagcatta aaatcgcagc                                                20

<210> SEQ ID NO 28
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 28
tttaatgtat tatttgccgc                                                20

<210> SEQ ID NO 29
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 29
tcattgccta tgcgtatg                                                  18

<210> SEQ ID NO 30
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 30
ggctttgcaa aaccagaag                                                 19

<210> SEQ ID NO 31
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 31
caagagttcc tcttaaactc                                                20

<210> SEQ ID NO 32
<211> LENGTH: 18
<212> TYPE: DNA
<213> ORGANISM: Artificial
<220> FEATURE:
<223> OTHER INFORMATION: An artificially synthesized primer sequence
```

```
<400> SEQUENCE: 32
catagttagt cgcgtcca                                                    18

<210> SEQ ID NO 33
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 33
ccagttaatc tcaggacg                                                    18

<210> SEQ ID NO 34
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 34
gtatccatgc tttatcaaga                                                  20

<210> SEQ ID NO 35
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 35
gtaggcctat aagagaacc                                                   19
```

DETECTION OF BACTERIA BELONGING TO THE GENUS *CAMPYLOBACTER* BY TARGETING CYTOLETHAL DISTENDING TOXIN

TECHNICAL FIELD

The present invention relates to methods for detecting the presence or absence of *Campylobacter* bacteria in test samples by targeting the cytolethal distending toxin of *Campylobacter* bacteria.

The present invention also relates to the cytolethal distending toxin of *Campylobacter hyointestinalis* and polynucleotides encoding it, as well as methods for detecting the presence or absence of *Campylobacter hyointestinalis* in test samples by targeting the cytolethal distending toxin of *Campylobacter hyointestinalis*.

BACKGROUND ART

Seventeen bacterial species of *Campylobacter* have been identified to date. Cultivation test is commonly used to identify *Campylobacter* bacterial species. However, the test requires complex and substantial effort because some bacterial species are difficult to identify based on their biochemical properties alone. Also, the bacteria are microaerophilic and depending on the bacterial species, some need to be cultured at different temperatures. Furthermore, the cultivation test for *Campylobacter* bacteria including isolation and identification usually takes a long time (seven to ten days).

More simple and rapid methods for identifying various species of *Campylobacter* bacteria are expected to be developed, because there is an increasing trend in both the *Campylobacter* infection rate and number of patients ("Food poisoning outbreak for each causative agent", the Ministry of Health, Labor and Welfare of the Japan).

It is difficult to rapidly identify *Campylobacter* bacterial species based on their biochemical properties, and some of *Campylobacter* species often cannot be distinguished based on their biochemical properties because of their close resemblance. For example, *Campylobacter jejuni* (hereinafter referred to as "*C. jejuni*") and *Campylobacter coli* (hereinafter referred to as "*C. coli*") are problematic because they are distinguished based on the presence of hippuricase activity, and when the enzyme activity is low, *C. jejuni* is falsely identified as *C. coli*. For this reason, PCR methods for detecting the presence of the hippuricase gene have been used in actual tests. In recent years, 16S rRNA gene analysis is frequently used as a method for identifying bacterial species at the gene level. However, *C. jejuni* and *C. coli* are highly homologous to each other, and thus often cannot be distinguished from each other by the 16S rRNA gene analysis.

To date, *C. jejuni* and *C. coli* account for about 94% and 4% of *Campylobacter* bacteria isolated from diarrhea patients, respectively. That is, the two bacterial species comprise the majority of *Campylobacter* bacteria. Thus, in most cases, test for *Campylobacter* bacteria in clinical practice only covers *C. jejuni* and *C. coli* which are specified as food poisoning bacteria. Furthermore, selection media commonly used in the test have been developed for mainly *C. jejuni* and *C. coli*, and the culture is generally carried out at 42° C. On the other hand, this bacterial isolation method is not suitable for bacterial species other than *C. jejuni* and *C. coli* because isolation of other bacterial species is less frequent. Specifically, depending on the selection medium or culture conditions used, sometimes bacterial species other than *C. jejuni* and *C. coli* cannot be isolated due to differences in the antibiotic sensitivity or optimal culture temperature among bacterial species belonging to the genus *Campylobacter*. That is, it is hard to say that the test covers *Campylobacter fetus* (hereinafter abbreviated as "*C. fetus*") which has different temperature-sensitive property, or other *Campylobacter* bacteria.

Meanwhile, bacterial species other than *C. jejuni* and *C. coli* are also distributed in the gastrointestinal tract of pets, domestic and wild animals or such, and thus the chance of human infection is thought to be high as with *C. jejuni* and *C. coli*. A mass outbreak of food poisoning caused by *C. fetus* occurred in Osaka in 2005. Infection with *C. fetus* causes not only gastroenteritis such as diarrhea but also other severe symptoms such as sepsis and meningitis in human. Furthermore, infection with *C. fetus* can result in infertility, miscarriage, or the like in animals such as cattle. In addition to *C. jejuni*, *C. coli*, and *C. fetus*, the three bacterial species, *Campylobacter lari* (hereinafter abbreviated as "*C. lari*"), *Campylobacter upsaliensis* (hereinafter abbreviated as "*C. upsaliensis*"), and *Campylobacter hyointestinalis* (hereinafter abbreviated as *C. hyointestinalis*"), are zoonotic bacteria that cause enteritis, sepsis, or such in human. Thus, it is important to improve the system for testing *Campylobacter* bacteria other than *C. jejuni*, *C. coli*, and *C. fetus*.

The present inventors cultured, isolated, and identified *Campylobacter* bacteria according to the Cape Town protocol without using antibiotics. The result showed that about 1.3% of patients with diarrhea caused by *Campylobacter* bacteria were infected with *C. hyointestinalis* (Non-patent Document 1).

*C. hyointestinalis* was isolated as a causative bacterium of porcine proliferative enteritis. Furthermore, *C. hyointestinalis* has been occasionally isolated from human enteritis patients, suggesting its involvement in human pathology. Nevertheless, there is no established rapid diagnosis method for *C. hyointestinalis*.

Thus, although the chance of potentially infecting human is highly suspected, there is no appropriate isolation/culture test method for *Campylobacter* bacteria other than *C. jejuni* and *C. coli*.

To solve the above-described problems, the present inventors focused and conducted their academic research on the cytolethal distending toxin (CDT) of *Campylobacter* bacteria (Non-patent Documents 2 and 3), and developed a method for detecting *Campylobacter* bacteria using the cytolethal distending toxin genes (cdtA, cdtB, and cdtC) (Patent Document 1). However, this detection method only targets *C. jejuni*, *C. coli*, and/or *C. fetus*, and no appropriate method has been developed for detecting other *Campylobacter* bacteria including *C. hyointestinalis*.

Prior art documents related to the present invention described herein are shown below.

[Patent Document 1] WO 2005/054472
[Non-patent Document 1] Lastovica A J. et al., *Campylobacter*, 2nd ed, 89-120 (2000)
[Non-patent Document 2] Asakura M. et al., Microbial Pathogenesis 42 (2007) 174-183
[Non-patent Document 3] Yamasaki S. et al., Toxin Reviews, 25: 61-88, 2006

DISCLOSURE OF THE INVENTION

Problems to be Solved by the Invention

The present invention was achieved in view of the circumstances described above. An objective of the present invention is to provide the cytolethal distending toxin (CDT) of *Campylobacter hyointestinalis* and polynucleotides encoding it.

Another objective of the present invention is to provide novel methods for detecting *Campylobacter hyointestinalis* using the cdt genes.

As described above, there is a need for rapid diagnosis of infection by *Campylobacter* bacteria species other than *C. jejuni* and *C. coli*, despite the fact that the pathogenic factors of *Campylobacter* bacteria have not been fully elucidated. Conventionally, PCR primers for identifying bacterial species based on the serotype thereof, common primers for testing CDT production, and such have been used (J. Applied Microbiol., 94: 1003-1014 (2003)). However, such methods require the step of an enrichment culture, making the rapid detection of *Campylobacter* bacteria impossible.

*C. hyointestinalis* was isolated as a causative bacterium of porcine proliferative enteritis. Furthermore, *C. hyointestinalis* has been occasionally isolated from human enteritis patients, suggesting its involvement in human pathology. Although the cytotoxin-like activity of a possible *C. hyointestinalis* pathogenic factor has been reported, the details remain to be clarified. Meanwhile, Johnson and Lior discovered a novel toxin called CDT in *E. coli* (Johnson W M, Lior H. 1988. Microbial Pathogen 4, 115-126.), and reported that *C. jejuni* also produces CDT. Subsequently, Pickett et al. determined the entire nucleotide sequence of the *C. jejuni* cdt genes (Pickett C L, et al., 1996. Infect Immun, 64, 2070-2078.), thereby revealing the exact identity of CDT. Furthermore, Pickett et al. reported that *C. hyointestinalis* also produces a toxin with CDT activity, and a PCR product corresponding to the cdtB gene can be amplified from *C. hyointestinalis* using degenerative primers. However, the bacterial DNA from *C. hyointestinalis* did not react with probes for the *C. jejuni* cdtB gene, and thus the exact identity of CDT produced by *C. hyointestinalis* remains unrevealed.

Therefore, an objective of the present invention is to provide the CDT (whose nucleotide sequence has not been elucidated) of *Campylobacter hyointestinalis* belonging to the genus *Campylobacter* and polynucleotides encoding the CDT, in order to enable rapid detection of *Campylobacter* bacteria by gene amplification. Another objective of the present invention is to provide novel methods for detecting *Campylobacter hyointestinalis* using the cdt genes.

Furthermore, the present invention provides primers for simultaneous detection of *Campylobacter* bacteria including *C. hyointestinalis*.

Means for Solving the Problems

The present inventors focused on the cytolethal distending toxin (CDT), which is recently thought to be a pathogenic factor produced by *Campylobacter* bacteria, and developed simple and rapid methods for detecting *Campylobacter hyointestinalis* in a species specific manner by targeting the cdt genes. CDT is a holotoxin consisting of the three subunits, CdtA, CdtB, and CdtC. The CdtA and CdtC subunits are involved in cell binding, while the CdtB subunit has DNase activity and is the main unit of toxin that exerts toxicity. The present inventors aimed to identify the species of *Campylobacter*-like bacteria isolated from an enteritis patient in Thailand by detection of the cdt genes, and developed and utilized a multiplex PCR method that can specifically detect *C. jejuni*, *C. coli*, and *C. fetus* by targeting the cdtA, cdtB, and cdtC genes, and a PCR method that uses common primers to simultaneously detect the cdtB gene of the three bacterial species. As a result, the present inventors found a bacterial strain whose cdt genes were not amplified by the multiplex PCR method specific to the three bacterial species, but whose cdtB gene was amplified by the common primers. This bacterial strain was identified as *C. hyointestinalis* by 16S rRNA gene analysis.

Then, the entire nucleotide sequence of the *C. hyointestinalis* cdt genes was determined by genome walking upstream and downstream of the cdtB gene. The sequence of an unidentified gene adjacent to a known gene is generally determined by inverse PCR. However, in the present invention, the entire nucleotide sequence of the cdt genes was determined for the first time by a method in which random primer extension and genome amplification are carried out and the amplified templates are sequenced.

Furthermore, the determined nucleotide sequence and deduced amino acid sequence were compared to the sequences previously reported for CdtA, CdtB, and CdtC of *C. jejuni*, *C. coli*, and *C. fetus*. The result showed that the cdtA and cdtC genes of *C. hyointestinalis* are most homologous to those of *C. jejuni* and the homologies are 51.7% and 52.5%, respectively. The cdtB gene of *C. hyointestinalis* is most homologous to that of *C. coli* and the homology is 64.1%. Thus, the homology is not very high.

Meanwhile, the homology of the deduced amino acid sequences of CdtA, CdtB, and CdtC was determined. The result showed that the three Cdt subunits of *C. hyointestinalis* exhibited the highest homology to those of *C. coli*. However, high homology was not obtained, and the respective amino acid sequence homologies were 35.7%, 60.5%, and 28.9%.

The present invention relates to methods for detecting *Campylobacter* bacteria by amplifying the *Campylobacter hyointestinalis* cdt genes. Specifically, the present invention provides the following:

[1] a polynucleotide encoding a cytolethal distending toxin, which is any one of (a) to (h) below:

(a) a polynucleotide encoding a polypeptide comprising the amino acid sequence of any one of SEQ ID NOs: 2 to 4;

(b) a polynucleotide comprising any one of the nucleotide sequences of positions 962 to 1600, 1601 to 2425, and 2425 to 3177 in the nucleotide sequence of SEQ ID NO: 1;

(c) a polynucleotide encoding a polypeptide comprising an amino acid sequence with one or more amino acid substitutions, deletions, additions, and/or insertions in any one of the amino acid sequences of SEQ ID NOs: 2 to 4;

(d) a polynucleotide that hybridizes under stringent conditions to a DNA comprising any one of the nucleotide sequences of positions 962 to 1600, 1601 to 2425, and 2425 to 3177 in the nucleotide sequence of SEQ ID NO: 1;

(e) a polynucleotide encoding a polypeptide comprising the amino acid sequence of any one of SEQ ID NOs: 6 to 8;

(f) a polynucleotide comprising any one of the nucleotide sequences of positions 1059 to 1835, 1853 to 2656, and 2666 to 3202 in the nucleotide sequence of SEQ ID NO: 5;

(g) a polynucleotide encoding a polypeptide comprising an amino acid sequence with one or more amino acid substitutions, deletions, additions, and/or insertions in the amino acid sequence of any one of SEQ ID NOs: 6 to 8; and (h) a polynucleotide that hybridizes under stringent conditions to a DNA comprising any one of the nucleotide sequences of positions 1059 to 1835, 1853 to 2656, and 2666 to 3202 in the nucleotide sequence of SEQ ID NO: 5;

[2] a vector comprising the polynucleotide of [1];

[3] a host cell comprising the polynucleotide of [1] or the vector of [2];

[4] a polypeptide encoded by the polynucleotide of [1];

[5] a method for producing the polypeptide of [4], which comprises the step of culturing the host cell of [3], and collecting the produced polypeptide from the host cell or the culture supernatant;

[6] an antibody that binds to the polypeptide of [4];

[7] the antibody of [6], wherein the antibody has an activity of neutralizing a cytolethal distending toxin;

[8] a method for simultaneously detecting the presence of one or more *Campylobacter* bacteria in a test sample, which comprises the steps of:

(a) conducting a nucleic acid amplification reaction on the test sample using a mixture of primer pair(s) specific to a genomic DNA encoding a cytolethal distending toxin of a *Campylobacter* bacterium; and (b) determining the presence of *Campylobacter* bacteria based on the presence or molecular weight of an fragment amplified from the genomic DNA encoding the cytolethal distending toxin of the *Campylobacter* bacterium;

[9] the method of [8], in which any one or more of the primer pairs of (i) to (iv) below are used as primer pair(s):

(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25;

(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19;

(iii) the primer pair of SEQ ID NOs: 32 and 33 for amplifying the genomic DNA encoding a cytolethal distending toxin of *Campylobacter upsaliensis*, or a primer pair capable of amplifying the same genomic DNA region amplified by the primer pair of SEQ ID NOs: 32 and 33; and (iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35.

[10] the method of [9], in which the primer pairs of (v) to (vii) below are additionally used as primer pair(s):

(v) the primer pair of SEQ ID NOs: 26 and 27 for amplifying the genomic DNA encoding a cytolethal distending toxin of *Campylobacter jejuni*, or a primer pair capable of amplifying the same genomic DNA region amplified by the primer pair of SEQ ID NOs: 26 and 27;

(vi) the primer pair of SEQ ID NOs: 28 and 29 for amplifying the genomic DNA encoding a cytolethal distending toxin of *Campylobacter coli*, or a primer pair capable of amplifying the same genomic DNA region amplified by the primer pair of SEQ ID NOs: 28 and 29;

(vii) the primer pair of SEQ ID NOs: 30 and 31 for amplifying the genomic DNA encoding a cytolethal distending toxin of *Campylobacter fetus*, or a primer pair capable of amplifying the same genomic DNA region amplified by the primer pair of SEQ ID NOs: 30 and 31;

[11] a kit for use in the method of [8], which comprises a manual and a mixture of one or more primer pairs specific to the genomic DNA encoding a cytolethal distending toxin of a *Campylobacter* bacterium;

[12] the kit of [11], which comprises any one or more of the primer pairs of (i) to (iv) below as primer pairs:

(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25;

(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19;

(iii) the primer pair of SEQ ID NOs: 32 and 33 for amplifying the genomic DNA encoding a cytolethal distending toxin of *Campylobacter upsaliensis*, or a primer pair capable of amplifying the same genomic DNA region amplified by the primer pair of SEQ ID NOs: 32 and 33; and (iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35;

[13] the kit of [12], which further comprises the primer pairs of (v) to (vii) below as primer pairs:

(v) the primer pair of SEQ ID NOs: 26 and 27 for amplifying the genomic DNA encoding a cytolethal distending toxin of *Campylobacter jejuni*, or a primer pair capable of amplifying the same genomic DNA region amplified by the primer pair of SEQ ID NOs: 26 and 27;

(vi) the primer pair of SEQ ID NOs: 28 and 29 for amplifying the genomic DNA encoding a cytolethal distending toxin of *Campylobacter coli*, or a primer pair capable of amplifying the same genomic DNA region amplified by the primer pair of SEQ ID NOs: 28 and 29;

(vii) the primer pair of SEQ ID NOs: 30 and 31 for amplifying the genomic DNA encoding a cytolethal distending toxin of *Campylobacter fetus*, or a primer pair capable of amplifying the same genomic DNA region amplified by the primer pair of SEQ ID NOs: 30 and 31;

[14] a method for detecting the presence of *Campylobacter hyointestinalis* in a test sample, which comprises the steps of:

(a) contacting a test sample with the antibody of [6];

(b) measuring the binding between the test sample and the antibody of [6]; and (c) determining that *Campylobacter hyointestinalis* is present if the binding is detected in (b);

[15] a kit for use in the method of [14], which comprises a manual and the antibody of [6].

BRIEF DESCRIPTION OF THE DRAWINGS

FIG. 2 presents a diagram showing a comparison of deduced CdtB amino acid sequences of *Campylobacter* bacteria. The boxed amino acid residues are thought to be essential for the DNase activity. "C. hyo$^{\#}$" means *C. hyointestinalis*.

FIG. 4A presents a photograph showing detection of Ch-CdtB by SDS-PAGE. FIG. 4B presents a photograph showing detection of Ch-CdtB by Western blotting. Lane 1, molecular weight marker; lane 2, 25 ng of Ch-rCdtB; lane 3, 10 µl of a crude toxin solution from *C. hyointestinalis* (Ch022). FIG. 4C presents a photograph showing the specificity of the Ch-rCdtB antiserum in gel double diffusion. rCjB, 1 µg of *C. jejuni* rCdtB; α-Cj, 10 µl of rCjB antiserum; rChB, 1 µg of *C. hyointestinalis* rCdtB; α-Ch, 10 µl of rChB antiserum.

FIG. 5A presents a diagram showing positions of the cdt genes and degeneration primers. FIG. 5B presents a photograph showing PCR results.

FIG. 7A to C present photographs showing Giemsa staining and microscopic observation (×100) of HeLa cells 48 hours after addition of a crude toxin solution and the anti-Ch-rCdtB serum. FIGS. 7D to F show measurement of the DNA content in HeLa cells after 48 hours by a flow cytometer. A and D, PBS; B and E, crude toxin solution (four times greater than CD50); F and G, crude toxin solution (four times greater than CD50) and anti-Ch-rCdtB serum.

FIG. 8 presents a diagram showing sites of common primers for the cdtB gene of *Campylobacter* bacteria.

FIG. 17 presents a diagram showing an alignment of the cdtB gene of the *C. hyointestinalis* Thai-derived Ch022 (SEQ ID NO: 5) and ATCC (SEQ ID NO: 1) strains, and positions of the primers.

MODE FOR CARRYING OUT THE INVENTION

Figure 1:
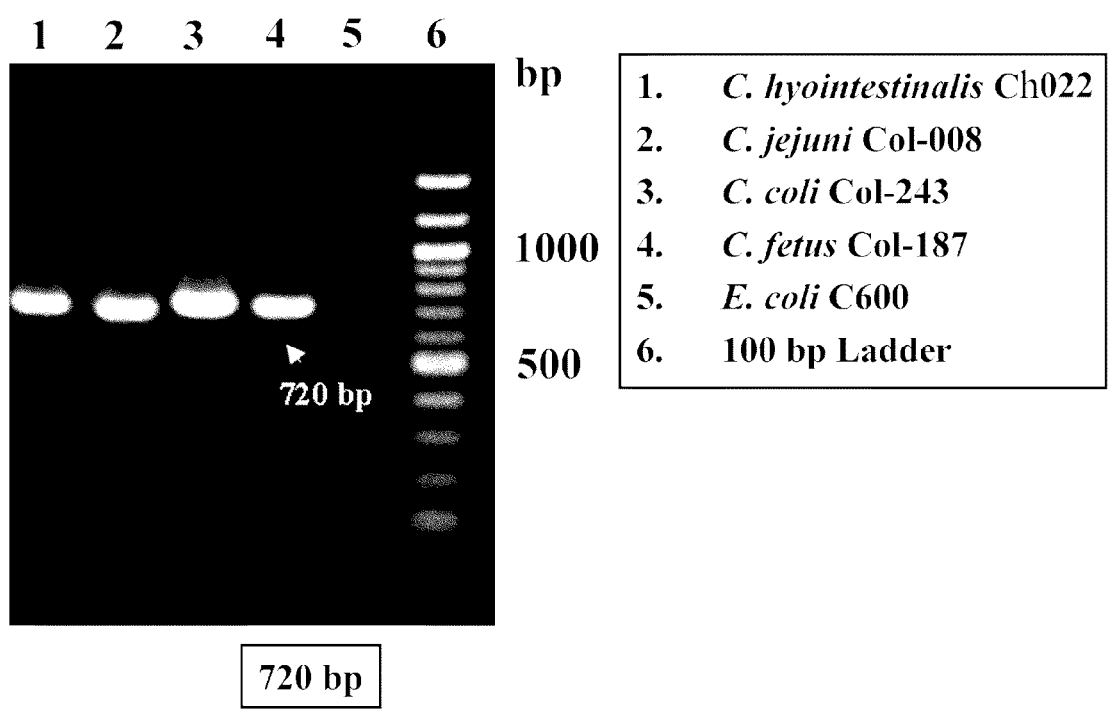
FIG. 1 presents a photograph showing PCR results for the Thai-derived *C. hyointestinalis* Ch022 strain and other *Campylobacter* bacteria using common primers that can amplify the cdtB gene of *C. jejuni, C. coli*, and *C. fetus*.

Herein, the phrase "cytolethal distending toxins" (CDTs or CLDTs) refers to toxic factors belonging to the group of proteinaceous type A-B holotoxins. The cytolethal distending toxin has a subunit structure consisting of three subunits A, B, and C. It is believed that subunit B is the active site unit of the toxin and subunits A and B are involved in cell adhesion. When the toxin acts on cells, it causes cell deformation such as cell swelling, and finally leads to cell death. Cell deformation such as cell swelling is also observed when heat-labile enterotoxin (LT), which is produced by toxigenic *E. coli*, or the like is experimentally allowed to act on cells. When the toxin is removed, however, the cells recover and survive. In contrast, cells do not recover but instead are killed, even when CDT is removed.

The term "polynucleotide" as used herein refers to a polymer made up of a number of bases or base pairs consisting of ribonucleotides or deoxyribonucleotides. Polynucleotides include single-stranded DNAs and double-stranded DNAs. Polynucleotides herein may include both unmodified, naturally-occurring polynucleotides and modified polynucleotides. Tritylated bases and special bases, such as inosine, are examples of modified bases.

The term "polypeptide" as used herein refers to a polymer made up of a number of amino acids. Therefore, oligopeptides and proteins are also included within the concept of polypeptides. Polypeptides include both unmodified, naturally-occurring polypeptides and modified polypeptides. Examples of polypeptide modifications include acetylation; acylation; ADP-ribosylation; amidation; covalent binding with flavin; covalent binding with heme moieties; covalent binding with nucleotides or nucleotide derivatives; covalent binding with lipids or lipid derivatives; covalent binding with phosphatidylinositols; cross-linkage; cyclization; disulfide bond formation; demethylation; covalent cross linkage formation; cystine formation pyroglutamate formation; formylation; g-carboxylation; glycosylation; GPI-anchor formation; hydroxylation; iodination; methylation; myristoylation; oxidation; proteolytic treatment; phosphorylation; prenylation; racemization; selenoylation; sulfation; transfer RNA-mediated amino acid addition to a protein such as arginylation; ubiquitination; and the like. The term "isolate" as used herein refers to a substance (for example, a polynucleotide or polypeptide) removed from its original environment (for example, the natural environment for a naturally-occurring substance) and "artificially" changed from its natural state. "Isolated" compounds refer to compounds including those present in samples that are substantially abundant with a subject compound, and/or those present in samples wherein the subject compound is partly or substantially purified. Herein, the term "substantially purified" refers to compounds (for example, polynucleotides or polypeptides) that are isolated from the natural environment and in which at least 60%, preferably 75%, and most preferably 90% of the other components associated with the compound in nature are absent.

The term "mutation" as used herein refers to changes to the amino acids of an amino acid sequence, or changes to the bases in a nucleotide sequence (that is, substitution, deletion, addition, or insertion of one or more amino acids or nucleotides). Therefore, the term "mutant" as used herein refers to amino acid sequences wherein one or more amino acids are changed, or nucleotide sequences wherein one or more nucleotides are changed. Nucleotide sequence changes in the mutant may change the amino acid sequence of the polypeptide encoded by the standard polynucleotide, or not. The mutant may be one that exists in nature, such as an allelic mutant, or one not yet identified in nature. The mutant may be conservatively altered, wherein substituted amino acids retain structural or chemical characteristics similar to those of the original amino acid. Rarely, mutants may be substituted non-conservatively. Computer programs known in the art, such as DNA STAR software, can be used to decide which or how many amino acid residues to substitute, insert, or delete without inhibiting biological or immunological activity.

"Deletion" is a change to either an amino acid sequence or nucleotide sequence, wherein one or more amino acid residues or nucleotide residues are missing as compared with the amino acid sequence of a naturally occurring cytolethal distending toxin polypeptide, or a nucleotide sequence encoding the same.

"Insertion" or "addition" is a change to either an amino acid sequence or nucleotide sequence, wherein one or more amino acid residues or nucleotide residues are added as compared with the amino acid sequence of a naturally-occurring cytolethal distending toxin polypeptide, or a nucleotide sequence encoding the same.

"Substitution" is a change to either an amino acid sequence or nucleotide sequence, wherein one or more amino acid residues or nucleotide residues are changed to different amino acid residues or nucleotide residues, as compared to the amino acid sequence of a naturally-occurring cytolethal distending toxin polypeptide, or a nucleotide sequence encoding the same.

The term "hybridize" as used herein refers to a process wherein a nucleic acid chain binds to its complementary chain through the formation of base pairs.

Herein, the term "detection" means both qualitative and quantitative measurements. "Quantitation" also refers to semiquantitative measurement.

<Polynucleotides>

The present invention provides polynucleotides encoding the cytolethal distending toxin of *Campylobacter hyointestinalis*. The present inventors identified the nucleotide sequence of a polynucleotide encoding the cytolethal distending toxin of the *Campylobacter hyointestinalis* strain from American Type Culture Collection (ATCC), and the polynucleotide is included in the present invention designated as SEQ ID NO: 1. The amino acid sequences of the three polypeptides encoded by the polynucleotide are shown in SEQ ID NOs: 2 to 4. The sequences of SEQ ID NOs: 2, 3, and 4 are the amino acid sequences of CdtA, CdtB, and CdtC, respectively.

Furthermore, the present inventors identified the nucleotide sequence of a polynucleotide encoding the cytolethal distending toxin of a clinically isolated *Campylobacter hyointestinalis* stain as shown in SEQ ID NO: 5. The amino acid sequences of the three polypeptides encoded by the polynucleotide are shown in SEQ ID NOs: 6 to 8. The sequences of SEQ ID NOs: 6, 7, and 8 are the amino acid sequences of CdtA, CdtB, and CdtC, respectively.

The polynucleotides of the present invention include polynucleotides encoding polypeptides comprising the amino acid sequences of SEQ ID NOs: 2 to 4; polynucleotides comprising any one of the coding regions of the nucleotide sequence of SEQ ID NO: 1, specifically any one of the nucleotide sequences of positions 962 to 1600, positions 1601 to 2425, and positions 2425 to 3177 in the nucleotide sequence of SEQ ID NO: 1; and polynucleotides that comprise a nucleotide sequence different from the nucleotide sequence of SEQ ID NO: 1 but encode polypeptides comprising the amino acid sequences of SEQ ID NOs: 2 to 4 due to genetic code degeneracy.

The polynucleotides of the present invention also include polynucleotides encoding polypeptides comprising the amino acid sequences of SEQ ID NOs: 6 to 8; polynucleotides comprising any one of the coding regions of the nucleotide sequence of SEQ ID NO: 5, specifically any one of the nucleotide sequences of positions 1059 to 1835, positions 1853 to 2656, and positions 2666 to 3202 in the nucleotide sequence of SEQ ID NO: 5; and polynucleotides that comprise a nucleotide sequence different from the nucleotide sequence of SEQ ID NO: 5 but encode polypeptides comprising the amino acid sequences of SEQ ID NOs: 6 to 8 due to genetic code degeneracy.

The polynucleotides of the present invention further include polynucleotides that encode polypeptides functionally equivalent to polypeptides encoded by the above polynucleotides and have a nucleotide sequence with an identity of at least 40% or higher, preferably 60% or higher, more preferably 80% or higher, even more preferably 90% or higher, still more preferably 95% or higher, yet more preferably 97% or higher (for example, 98 to 99%) to the entire sequence of the polynucleotide. The nucleotide sequence identity can be determined, for example, using the algorithm BLAST by Karlin and Altschul (Proc. Natl. Acad. Sci. USA 87:2264-2268, 1990; Proc. Natl. Acad. Sci. USA 90:5873-5877, 1993). A program called BLASTN has been developed based on this algorithm (Altschul et al. J. Mol. Biol. 215:403-410, 1990). When nucleotide sequences are analyzed by BLASTN, the parameters are set, for example, as follows: score=100; wordlength=12. When BLAST and Gapped BLAST programs are used, default parameters are used for each program. The specific techniques for these analytical methods are known (http://www.ncbi.nlm.nih.gov.). The polynucleotides of the present invention include polynucleotides having nucleotide sequences complementary to the above polynucleotide sequences.

The polynucleotides of the present invention can be obtained through standard cloning and screening methods from natural sources, such as genomic DNA in bacterial cells. Alternatively, the polynucleotides can be obtained from cDNA libraries derived from mRNA in bacterial cells. The polynucleotides can also be synthesized using known techniques that are commercially available.

Polynucleotides having nucleotide sequences with significant homology to the polynucleotide sequences identified by the present inventors (e.g., SEQ ID NOs: 1 and 5) can be prepared, for example, using hybridization techniques (Current Protocols in Molecular Biology edit. Ausubel et al. (1987) Publish. John Wiley & Sons Section 6.3-6.4) and gene amplification techniques (PCR) (Current protocols in Molecular Biology edit. Ausubel et al. (1987) Publish. John Wiley & Sons Section 6.1-6.4). Specifically, based on the polynucleotide sequences identified by the present inventors (e.g., SEQ ID NOs: 1 and 5) or portions thereof, DNA highly homologous to the sequences can be isolated using known hybridization techniques. Alternatively, polynucleotides highly homologous to the polynucleotide sequences can be isolated by gene amplification techniques, using primers designed based on portions of the polynucleotide sequences identified by the present inventors (e.g., SEQ ID NOs: 1 and 5). Thus, the present invention includes polynucleotides that hybridize to the polynucleotide having the nucleotide sequence of SEQ ID NO: 1 or 5 under stringent conditions. Those skilled in the art can select suitable stringent hybridization conditions. For example, hybridization can be carried out by overnight prehybridization at 42° C. in a hybridization solution containing 25% formamide (or 50% formamide for more stringent conditions), 4×SSC, 50 mM Hepes (pH 7.0), 10×Denhardt's solution, and 20 µg/ml denatured salmon sperm DNA; followed by addition of a labeled probe and hybridization by overnight incubation at 42° C. Post-hybridization wash may be carried out under the washing solution and temperature conditions of "1×SSC, 0.1% SDS, 37° C." or such, "0.5×SSC, 0.1% SDS, 42° C." or such for more stringent conditions, or "0.2×SSC, 0.1% SDS, 65° C." for yet more stringent conditions. As the stringency of the hybridization washing condition increases as described above, isolation of DNAs having higher homology to the probe sequence is expected. However, the above combinations of SSC, SDS, and temperature condition are only exemplary. Those skilled in the art can achieve the same stringency described above by appropriately combining the above or other factors that determine the degree of hybridization stringency, for example, probe concentration and length, and reaction time for hybridization.

Polynucleotides including nucleotide sequences with significant homology to the polynucleotide sequences identified by the present inventors can also be prepared by methods for introducing mutations into the nucleotide sequences of SEQ ID NOs: 1 and 5 (for example, site directed mutagenesis (Current Protocols in Molecular Biology edit. Ausubel et al. (1987) Publish. John Wiley & Sons Section 8.1-8.5)). Such polynucleotides may also be generated by naturally-occurring mutations. The present invention includes polynucleotides encoding the polypeptides having an amino acid sequence wherein one or more amino acids is substituted, deleted, inserted and/or added in the amino acid sequences of SEQ ID NOs: 2 to 4 or 6 to 8 due to such nucleotide sequence mutations.

When the polynucleotides of the present invention are used to produce the polypeptides of the present invention, the polynucleotides include coding sequences for the mature polypeptides or fragments thereof alone, or coding sequences for the mature polypeptides or fragments thereof which are located in the same reading frame as other coding sequences (for example, leader or secretory sequence, pre-, pro-, or prepro-protein sequence, or sequences encoding other fusion peptide portions). For example, marker sequences that facilitate purification of fusion polypeptides may be encoded. In this embodiment of the present invention, preferred examples of marker sequences include, for example, hexa-histidine peptide or Myc tag which is provided by pcDNA3.1/Myc-His vector (Invitrogen) and described in Gentz et al., Proc. Natl. Acad. Sci. USA (1989) 86:821-824. The polynucleotide may also include 5' and 3' non-coding sequences, for example, transcribed but untranslated sequences, splicing and polyadenylation signals, ribosome-binding site, and mRNA-stabilizing sequence.

<Polypeptide>

The present invention provides polypeptides of the cytolethal distending toxin of *Campylobacter hyointestinalis* identified by the present inventors. The present invention also provides polypeptides functionally equivalent to the polypeptides identified by the present inventors. Herein, "functionally equivalent" means that a polypeptide of interest has equivalent characteristics of cytolethal distending toxin to those of the polypeptides identified by the present inventors.

Introducing mutations into the amino acid sequence of proteins is one means for preparing polypeptides functionally equivalent to the polypeptides identified by the present inventors. Such methods include, for example, site-directed mutagenesis (Current Protocols in Molecular Biology, edit. Ausubel et al. (1987) Publish. John Wiley & Sons Section 8.1-8.5). Amino acid mutation in polypeptides may also occur in nature. The present invention includes mutant proteins, regardless of whether artificially or naturally produced, that include the amino acid sequence identified by the present inventors (e.g., SEQ ID NOs: 2 to 4 and 6 to 8), wherein one or more amino acid residues are altered by substitution, deletion, insertion, and/or addition, yet which are functionally equivalent to the polypeptides identified by the present inventors.

From the viewpoint of conserving the protein's functions, an amino acid residue used for substitution preferably has properties similar to the substituted amino acid residue (conservative substitution). For example, Ala, Val, Leu, Ile, Pro, Met, Phe, and Trp are all classified as non-polar amino acids, and are considered to have similar properties. Further, examples of uncharged amino acids are Gly, Ser, Thr, Cys, Tyr, Asn, and Gln. Moreover, examples of acidic amino acids are Asp and Glu, and those of basic amino acids are Lys, Arg, and His.

There are no limitations as to the number and site of the amino acid mutations of these polypeptides, as long as the mutated polypeptides retain a function of the original polypeptide. The number of mutations may be typically less than 10%, preferably less than 5%, and more preferably less than 1% of the total amino acid residues.

Other means for preparing polypeptides functionally equivalent to the polypeptides identified by the present inventors include methods that utilize hybridization techniques or gene amplification techniques. More specifically, those skilled in the art can obtain polypeptides functionally equivalent to the polypeptides determined by the present inventors by isolating highly homologous DNAs from DNA samples derived from organisms of the same or different species using hybridization techniques (Current Protocols in Molecular Biology, edit. Ausubel et al. (1987) Publish. John Wiley & Sons Section 6.3-6.4) based on the DNA sequence encoding the polypeptides identified by the present inventors (SEQ ID NO: 1 and 5). Thus, such polypeptides encoded by DNAs hybridizing to the DNAs encoding the polypeptides identified by the present inventors, which are functionally equivalent to the polypeptides identified by the present inventors, are also included in the polypeptides of this invention.

Those skilled in the art can select suitable stringent hybridization conditions for isolation of a DNA encoding a polypeptide functionally equivalent to the polypeptides identified by the present inventors. For example, hybridization can be carried out by overnight prehybridization at 42° C. in a hybridization solution containing 25% formamide (or 50% formamide for more stringent conditions), 4×SSC, 50 mM Hepes (pH 7.0), 10×Denhardt's solution, and 20 μg/ml denatured salmon sperm DNA; followed by addition of a labeled probe and hybridization by overnight incubation at 42° C. Post-hybridization wash may be carried out under the washing solution and temperature conditions of "1×SSC, 0.1% SDS, 37° C." or such, "0.5×SSC, 0.1% SDS, 42° C." or such for more stringent conditions, or "0.2×SSC, 0.1% SDS, 65° C." for yet more stringent conditions. As the stringency of the hybridization washing condition increases as described above, isolation of DNAs having higher homology to the probe sequence is expected. However, the above-mentioned combinations of SSC, SDS, and temperature conditions are only examples, and those skilled in the art can achieve the same stringencies as described above by appropriately combining the above-mentioned factors or other parameters that determine hybridization stringency (for example, probe concentration, probe length, reaction time of hybridization, etc.).

The polypeptides encoded by DNAs isolated using such hybridization techniques normally have amino acid sequences highly homologous to the polypeptides identified by the present inventors. Herein, high homology indicates sequence identity of at least 40% or more, preferably 60% or more, more preferably 80% or more, still more preferably 90% or more, further still more preferably at least 95% or more, and yet more preferably at least 97% or more (for example, 98% to 99%). Homology of amino acid sequences can be determined, for example, using the algorithm BLAST of Karlin and Altschul (Proc. Natl. Acad. Sci. USA 87: 2264-2268 (1990); Proc. Natl. Acad. Sci. USA 90: 5873-5877 (1993)). Based on this algorithm, a program referred to as BLASTX has been developed (Altschul et al., J. Mol. Biol. 215: 403-410 (1990)). When amino acid sequences are analyzed using BLASTX, parameters are set, for example, at score=50 and word length=3. When using BLAST and Gapped BLAST programs, default parameters of each program are used. Specific techniques for these analytical methods are well known in the art.

Gene amplification techniques (PCR) (Current Protocols in Molecular Biology, edit. Ausubel et al. (1987) Publish. John Wiley & Sons Section 6.1-6.4) can be utilized to obtain polypeptides functionally equivalent to the polypeptides isolated by the present inventors, based on DNA fragments isolated as DNAs highly homologous to the DNA sequences encoding the polypeptides isolated by the present inventors. This can be achieved by designing primers based on a part of the DNA sequence encoding the polypeptides identified by the present inventors (SEQ ID NOs: 1 and 5).

<Polypeptide Fragments>

The present invention also provides fragments of the polypeptides of this invention. These fragments are polypeptides having amino acid sequences that are partly, but not entirely, identical to the above polypeptides of this invention. The polypeptide fragments of this invention usually include eight amino acid residues or more, and preferably twelve amino acid residues or more (for example, 15 amino acid residues or more). Examples of preferred fragments include truncated polypeptides, such as amino acid sequences that lack a series of amino acid residues including either the amino terminus or carboxyl terminus, or two series of amino acid residues, one including the amino terminus and the other including the carboxyl terminus. Furthermore, fragments featuring structural or functional characteristics are also preferable, and include those having α-helix and α-helix forming regions, β-sheet and β-sheet forming regions, turn and turn-forming regions, coil and coil-forming regions, hydrophilic regions, hydrophobic regions, α-amphipathic regions, β-amphipathic regions, variable regions, surface forming regions, substrate-binding regions, and high antigenicity index regions. Biologically active fragments are also preferred. Biologically active fragments mediate the activities of the polypeptides of this invention, and include those that have a similar or improved activity, or a reduced undesirable activity. For example, fragments that are antigenic or immunogenic in animals, especially humans, are included. These polypeptide fragments preferably retain a biological activity, such as antigenicity, of the polypeptides of this invention. Mutants of specific sequences or fragments also constitute an aspect of this invention. Preferred mutants are those that differ from the subject polypeptide due to replacement with conservative amino acids, namely, those in which a residue is substituted with another residue of similar properties. Typical substitutions are those between Ala, Val, Leu, and Ile; Ser and Thr; acidic residues Asp and Glu, Asn, and Gln; basic residues Lys and Arg; or aromatic residues Phe and Tyr.

<Production of Polypeptides>

Polypeptides of this invention may be produced by any appropriate method. Such polypeptides include isolated naturally-occurring polypeptides, and polypeptides which are produced by gene recombination, synthesis, or by a combination thereof. Procedures for producing these polypeptides are well known in the art. Recombinant polypeptides may be prepared, for example, by transferring a vector, inserted with a polynucleotide of the present invention, into an appropriate host cell, and purifying the polypeptide expressed within the resulting transformant. On the other hand, naturally occurring polypeptides can be prepared, for example, using affinity columns wherein antibodies against a polypeptide of this invention (described below) are immobilized (Current Protocols in Molecular Biology, edit. Ausubel et al. (1987) Publish. John Wiley & Sons, Section 16.1-16.19). Antibodies for affinity purification may be either polyclonal or monoclonal antibodies. The polypeptides of this invention may be also prepared by in vitro translation methods (for example, see "On the fidelity of mRNA translation in the nuclease-treated rabbit reticulocyte lysate system." Dasso, M. C. and Jackson, R. J. (1989) NAR 17: 3129-3144), and such. The polypeptide fragments of this invention can be produced, for example, by cleaving the polypeptides of the present invention with appropriate peptidases.

<Probes and Primers>

The present invention provides polynucleotides with a chain length of at least 15 nucleotides or 20 nucleotides, for example, polynucleotides with a chain length of 15 to 100 nucleotides, 20 to 100 nucleotides, 15 to 35 nucleotides, or 20 to 35 nucleotides, which are complementary to a polynucleotide identified by the present inventors (e.g., a polynucleotide having the nucleotide sequence of SEQ ID NO: 1 or a complementary strand thereof, and a polynucleotide having the nucleotide sequence of SEQ ID NO: 5 or a complementary strand thereof). Herein, the term "complementary strand" is defined as the other strand of a double-stranded nucleic acid composed of A:T (A:U in case of RNA) and G:C base pairs. In addition, the term "complementary" encompasses not only complete matching within a continuous region of at least 15 sequential nucleotides, but also homology of at least 70%, preferably at least 80%, more preferably 90%, and most preferably 95% or higher within that region. Homology may be determined using an algorithm described herein. Probes and primers for detection or amplification of the polynucleotides of the present invention are included in these polynucleotides. Typical polynucleotides used as primers are 15 to 100 nucleotides long, and preferably 15 to 35 nucleotides long. Alternatively, polynucleotides used as probes are nucleotides at least 15 nucleotides in length, and preferably at least 30 nucleotides. They include at least a portion or an entire sequence of a DNA of the present invention. When using the nucleotides of the present invention as primers, the nucleic acid amplification reaction is not particularly limited, as long as a desired amplification product can be obtained. For example, the reaction may be selected from DNA amplification reactions such as polymerase chain reaction (PCR), ICAN, LAMP, SDA, and LCR, and RNA amplification reactions such as NASBA. A preferred method is PCR.

In one embodiment, such nucleotides are those specific to a DNA encoding a polypeptide of the present invention. The term "specific" refers to hybridizing under normal hybridization conditions, preferably stringent conditions, with DNA encoding a certain polypeptide, but not with DNAs encoding other polypeptides.

Specific examples of primers for amplifying a portion of the polynucleotides identified by the present inventors include the primers of (i) and (ii) below, which are described in the Examples herein.

(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25; and (ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19.

As described above, the nucleic acid amplification reaction applicable to the primers of the present invention is not particularly limited, as long as it yields desired amplification products. For example, the reaction can be selected from DNA amplification reactions such as PCR (polymerase chain reaction), ICAN, LAMP, SDA, and LCR, and RNA amplification reactions such as NASBA. A preferred method is PCR.

Based on the above primers, those skilled in the art can design mutant primers suitable for nucleic acid amplification methods to be performed. Such mutant primers can be synthetically prepared. It can be readily assessed whether mutant primers can amplify the same genomic DNA region as amplified with the original primers, by conducting a nucleic acid amplification reaction using the mutant primers and analyzing the amplification products.

These primers can be preferably used to detect the presence of *Campylobacter hyointestinalis* in test samples.

<Production of Vectors, Host Cells, and Polypeptides>

The present invention also provides methods for producing vectors carrying polynucleotides of the present invention, host cells retaining the polynucleotides or said vectors of the present invention, and polypeptides of the present invention utilizing said host cells.

The vectors of the present invention are not limited, as long as the DNAs inserted in the vectors are stably retained. For example, pBluescript vector (Stratagene) is a preferable cloning vector when using *E. coli* as a host. When using vectors to produce the polypeptides of the present invention, expression vectors are particularly useful. These expression vectors are not specifically limited, as long as they express polypeptides in vitro, in *E. coli*, in cultured cells, or in vivo. However, preferred examples include the pBEST vector (ProMega) for in vitro expression, the pET vector (Invitrogen) for expression in *E. coli*, the pME18S-FL3 vector (GenBank Accession No. AB009864) for expression in cultured cells, and the pME18S vector (Mol. Cell. Biol. 8:466-472 (1988)) for in vitro expression, and such. A DNA of the present invention can be inserted into a vector by conventional methods, for example, by a ligase reaction using restriction enzyme sites (Current Protocols in Molecular Biology, edit. Ausubel, et al., (1987) Publish. John Wiley & Sons, Section 11.4-11.11).

Host cells into which the vectors of the present invention are introduced are not specifically limited, and various host cells can be used according to the objectives of the present invention. For example, bacterial cells (e.g. *Streptococcus, Staphylococcus, E. coli, Streptomyces, Bacillus subtilis*), fungal cells (e.g. yeast, *Aspergillus*), insect cells (e.g. *Drosophila* S2, *Spodoptera* SF9), animal cells (e.g. CHO, COS, HeLa, C127, 3T3, BHK, HEK293, Bowes melanoma cell), and plant cells are examples of cells for expressing polypeptides. The transfection of a vector into a host cell can be carried out by conventional methods, such as calcium phosphate precipitation methods, electroporation methods (Current protocols in Molecular Biology, edit., Ausubel et al., (1987) Publish. John Wiley & Sons, Section 9.1-9.9), Lipofectamine methods (GIBCO-BRL), microinjection methods, and such.

In host cells, appropriate secretion signals can be incorporated into a polypeptide of interest in order to facilitate the secretion of an expressed polypeptide into the lumen of the endoplasmic reticulum, into the cavity around a cell, or into the extracellular environment. These signals may be endogenous signals or signals from a species different from the target polypeptide.

When a polypeptide of the present invention is secreted into culture medium, this culture medium is collected to collect the polypeptide of the present invention. When a polypeptide of the present invention is produced intracellularly, the cells are first lysed, and the polypeptide is then collected.

In order to collect and purify a polypeptide of the present invention from a recombinant cell culture, methods known in the art can be used, including ammonium sulfate or ethanol precipitation, acid extraction, anionic or cationic exchange chromatography, phosphocellulose chromatography, hydrophobic interaction chromatography, affinity chromatography, hydroxylapatite chromatography, and lectin chromatography.

<Antibodies>

The present invention provides antibodies that bind to a polypeptide of the present invention. Herein, the term "antibodies" refers to polyclonal antibodies, monoclonal antibodies, chimeric antibodies, single-stranded antibodies, humanized antibodies, and Fab fragments including Fab or other products of an immunoglobulin expression library.

A polypeptide of the present invention, fragments and derivatives thereof, and cells expressing them can be used as an immunogen for producing antibodies that bind to the polypeptide of the present invention. Such antibodies are preferably immunospecific to the polypeptide of the present invention. "Immunospecific" means that the antibody has substantially higher affinity to the polypeptide of the present invention than to other polypeptides. Furthermore, more preferably, antibodies of the present invention include antibodies having an activity of neutralizing the cytolethal distending toxin of *C. hyointestinalis.*

The antibodies binding to a polypeptide of the present invention can be prepared by methods known to those skilled in the art. For example, a polyclonal antibody can be obtained by administering a polypeptide of the present invention or a GST-fusion protein thereof to small animals such as rabbits to obtain serum. Polyclonal antibodies are prepared by purifying the serum by ammonium sulfate precipitation; a protein A or protein G column; DEAE ion exchange chromatography; an affinity column in which the polypeptide of the present invention is coupled; and such. On the other hand, monoclonal antibodies, for example, can be prepared by administering a polypeptide of the present invention to small animals such as mice, and their spleens are subsequently extirpated and ground down to separate the cells. The cells are then fused with mouse myeloma cells using reagents such as polyethylene glycol, and clones that produce antibodies binding to the polypeptide of the present invention are selected from these fused cells (hybridomas). The obtained hybridomas are then transplanted into mice peritoneal cavities, and ascites are collected from the mice. The monoclonal antibodies can be prepared by purifying the ascites using, for example, ammonium sulfate precipitation; a protein A or protein G column; DEAE ion exchange chromatography; an affinity column in which the polypeptides of the present invention are coupled; and such.

The antibodies of the present invention can also be used to detect and purify the polypeptides of the present invention in test samples.

<Detection of the Presence of *Campylobacter* Bacteria in Test Samples>

The present invention provides methods for detecting *Campylobacter* bacteria in test samples. Detection of the presence of *Campylobacter* bacteria in test samples is useful for various purposes such as diagnosis of *Campylobacter* infection, rapid test of food contaminated with *Campylobacter hyointestinalis*, validation in each step of food processing, and identification of bacteria responsible for food poisoning outbreak.

In one embodiment, the detection method of the present invention is a method for detecting the presence of one or more *Campylobacter* bacteria in a test sample, which comprises the steps of: (a) conducting a nucleic acid amplification reaction on the test sample using a mixture of primer pair(s) specific to a genomic DNA encoding a cytolethal distending toxin of a *Campylobacter* bacterium; and (b) determining the presence of *Campylobacter* bacteria based on the presence or molecular weight of an fragment amplified from the genomic DNA encoding the cytolethal distending toxin of the *Campylobacter* bacterium.

In the present invention, the "primers specific to the genomic DNA" are not limited to primers specific to a genomic DNA region encoding the cytolethal distending toxin of a *Campylobacter* bacterium, but also include primers specific to an mRNA region corresponding to the genomic DNA region.

Oligonucleotide primers that specifically hybridize with the genomic DNA encoding the cytolethal distending toxin of a *Campylobacter* bacterium can be prepared by the methods described above. The primer binding sequence segment is not particularly limited; however, it may be designed to have appropriate restriction sites that allow restriction enzyme cleavage of the primer segment after PCR amplification. There is no particular limitation on the length of the primer binding sequence segment, and the length is about 20 to 50 nucleotides, preferably about 20 to 30 nucleotides. Furthermore, the primers may be labeled at the 5' end with radiolabels, fluorescent labels, or the like, so that the single-stranded DNAs can be isolated by electrophoresis or such after PCR amplification. Alternatively, to prepare RNA molecules, the 5'-end primers may be designed to have an appropriate promoter, for example, a T7 promoter sequence, in order to allow transcription of the DNA molecule into an RNA molecule.

The methods of the present invention may further comprise the step of identifying *Campylobacter* bacterial species by the PCR-restriction fragment length polymorphism (PCR-RFLP) method. In the PCR-RFLP method, PCR-amplified DNAs are digested with various restriction enzymes and then polymorphism is detected based on the length of the resulting fragments. The cdt gene sequences of *Campylobacter* bacteria, which are to be detected in the present invention, vary depending on the bacterial species. Thus, the PCR-RFLP method can be used to identify bacterial species.

In this step, sites that have different sequences depending on the bacterial species (polymorphic sites) are first determined by sequence comparison, and then restriction enzymes that recognize the polymorphic sites in any of the bacterial species are selected. If such restriction enzymes already exist, whether bacterial species that have the polymorphic sites are present in a sample containing multiple *Campylobacter* bacteria species can be determined by carrying out PCR that targets the cdt genes, digesting the resulting PCR products with the restriction enzymes, and comparing the length of the fragments by electrophoresis. Those skilled in the art can identify sites with different sequences by comparing known *Campylobacter* bacterial cdt genes with the *C. hyointestinalis* cdt genes provided by the present invention, and select appropriate restriction enzymes that recognize the sites.

The present invention also provides primers that are preferably used in methods for polymorphism detection based on the length of fragments obtained from digesting DNAs amplified by nucleic acid amplification methods with various restriction enzymes, including PCR-RFLP.

An example of applying the PCR-RFLP method in the present invention is amplifying fragments by the pair of primers comprising the sequences of SEQ ID NOs: 18 and 19 (primers used in the Examples herein: cdtB commonU and cdtB commonR), and digesting the fragments with restriction enzyme EcoRI, XbaI, HindIII, or Sau3AI alone or a combination thereof; and bacterial species can be identified by electrophoresis.

More specifically, the detection methods of the present invention include, for example, methods for simultaneously detecting the presence of one or more *Campylobacter* bacterial species in a test sample, which comprise the step of performing nucleic acid amplification reaction on the test sample using any one or more of the primer pairs below which are specific to genomic DNA encoding a *Campylobacter* cytolethal distending toxin: "(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25", "(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19", "(iii) the primer pair of SEQ ID NOs: 32 and 33 for amplifying the genomic DNA encoding a cytolethal distending toxin of *Campylobacter upsaliensis*, or a primer pair capable of amplifying the same genomic DNA region amplified by the primer pair of SEQ ID NOs: 32 and 33; and "(iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35.

The above-described methods are methods that detect bacteria by amplifying regions specific to the genomic DNA or mRNA of *C. hyointestinalis*, *C. upsaliensis*, and *C. lari* cdtB.

Primers used in the above-described methods include, for example, the "primer pair comprising the sequences of SEQ ID NOs: 24 and 25 (primers used in the Examples herein: ChspBU7 and ChspBR7)" and the "primer pair comprising the sequences of SEQ ID NOs: 18 and 19 (primers used in the Examples herein: cdtB commonU and cdtB commonR)" for *C. hyointestinalis*, without being limited thereto. Any other sequences may be used as long as they are primer pairs comprising two polynucleotides that can specifically bind to the genomic DNA or mRNA of *C. hyointestinalis* cdtB, and amplify the region amplified using the genomic DNA of *C. hyointestinalis* cdtB as template and the "primer pair comprising the sequences of SEQ ID NOs: 24 and 25" or the "primer pair comprising the sequences of SEQ ID NOs: 18 and 19", or the corresponding mRNA region. Herein, "specifically binds" means excluding incidental or non-specific binding from the "binding".

FIG. 17 shows sites in the cdtB gene to which the above-described primers for detecting *C. hyointestinalis* bind.

Alternatively, as for *C. upsaliensis*, the primers representatively include the "primer pair comprising the sequences of SEQ ID NOs: 32 and 33 (primers used in the Examples herein: CupspBU3 and CupspBR4)", but are not limited to these sequences. Any other sequences may be used as long as they are primer pairs that can amplify the region amplified using the genomic DNA of *C. fetus* cdtB as template and the "primer pair comprising the sequences of SEQ ID NOs: 32 and 33", or the corresponding mRNA region.

Furthermore, as for *C. fetus*, the primers representatively include the "primer pair comprising the sequences of SEQ ID NOs: 34 and 35 (primers used in the Examples herein: ClaspBU4 and ClaspBR4)", but are not limited to these sequences. Any other sequences may be used as long as they are primer pairs that can amplify the region amplified using the genomic DNA of *C. fetus* cdtB as template and the "primer pair comprising the sequences of SEQ ID NOs: 34 and 35", or the corresponding mRNA region.

In the methods of the present invention, the primer pairs of (i) to (iv) above may be used separately. Alternatively, multiple primer pairs can be used simultaneously in a single nucleic acid amplification reaction. The PCR method in which multiple PCR primers are used in a single reaction such as in the Examples herein is called "multiplex PCR". Thus, different bacterial species can be identified by electrophoresing the PCR products and determining the band size. The present invention provides methods for detecting *Campylobacter* bacteria by nucleic acid amplification, representatively including the above-described multiplex PCR, using primers and combinations thereof preferably used for amplifying different nucleic acid regions. In the present invention, there is no limitation on the type of nucleic acid amplification method, as long as it yields amplification products of interest. It is possible to select any type of known nucleic acid amplification reaction, for example, the polymerase chain reaction (PCR) method (including RT-PCR method), ICAN method, LAMP method, SDA method, LCR method, and NASBA method. The PCR method is a specific example of nucleic acid amplification method preferably used in the present invention. The methods of the present invention may be implemented as a quantitation method by real-time PCR or such.

In the methods of the present invention, a single nucleic acid amplification reaction can be performed using the primer pairs of (i) to (iv) above in combination with: "(v) the primer pair of SEQ ID NOs: 26 and 27 for amplifying the genomic DNA encoding a cytolethal distending toxin of *Campylobacter jejuni* (primers used in the Examples herein: Cj-CdtBU5 and Cj-CdtBR6), or a primer pair capable of amplifying the same genomic DNA region amplified by the primer pair of SEQ ID NOs: 26 and 27", "(vi) the primer pair of SEQ ID NOs: 28 and 29 for amplifying the genomic DNA encoding a cytolethal distending toxin of *Campylobacter coli* (primers used in the Examples herein: Cc-CdtBU5 and Cc-CdtBR5), or a primer pair capable of amplifying the same genomic DNA region amplified by the primer pair of SEQ ID NOs: 28 and 29, and "(vii) the primer pair of SEQ ID NOs: 30 and 31 for amplifying the genomic DNA encoding a cytolethal distending toxin of *Campylobacter fetus* (primers used in the Examples herein: Cf-CdtBU6 and Cf-CdtBR3), or a primer pair capable of amplifying the same genomic DNA region amplified by the primer pair of SEQ ID NOs: 30 and 31". Specifically, the present invention provides methods that can simultaneously detect the six *Campylobacter* bacterial species, *C. hyointestinalis, C. upsaliensis, C. lari, C. jejuni, C. fetus*, and *C. coli*, in a test sample. The present inventors demonstrated that the above-described six *Campylobacter* bacterial species can be simultaneously detected by nucleic acid amplification reaction that uses the above-described primers in combination. As demonstrated in the Examples herein, the methods of the present invention have very high specificity because they can detect *Campylobacter* bacteria of interest without erroneous detection of other *Campylobacter* bacterial species.

The methods of the present invention comprise, subsequent to the above-described step of nucleic acid amplification reaction using primers specific to the six *Campylobacter* bacterial species, the "step of determining the presence of *Campylobacter* bacteria based on the presence or molecular weight of fragments amplified from the genomic DNA or mRNA of *Campylobacter* bacterial cdt" or the "step of quantifying the amount of fragments amplified from the genomic DNA or mRNA of *Campylobacter* bacterial cdt".

The present invention provides kits to be used in the detection methods of the present invention. The kits comprise manuals in addition to the primer pairs. The kits may further comprise other materials, for example, fluorescent probes, intercalators, agents for preparing polynucleotides, and positive or negative primer pairs.

The first embodiment of the kits of the present invention includes kits comprising at least one of the following primer pairs:

"(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25", "(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19", "(iii) the primer pair of SEQ ID NOs: 32 and 33 for amplifying the genomic DNA encoding a cytolethal distending toxin of *Campylobacter upsaliensis*, or a primer pair capable of amplifying the same genomic DNA region amplified by the primer pair of SEQ ID NOs: 32 and 33; and "(iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35.

Alternatively, the above-described kits may further comprise: "(v) the primer pair of SEQ ID NOs: 26 and 27 for amplifying the genomic DNA encoding a cytolethal distending toxin of *Campylobacter jejuni* (primers used in the Examples herein: Cj-CdtBU5 and Cj-CdtBR6), or a primer pair capable of amplifying the same genomic DNA region amplified by the primer pair of SEQ ID NOs: 26 and 27", "(vi) the primer pair of SEQ ID NOs: 28 and 29 for amplifying the genomic DNA encoding a cytolethal distending toxin of *Campylobacter coli* (primers used in the Examples herein: Cc-CdtBU5 and Cc-CdtBR5), or a primer pair capable of amplifying the same genomic DNA region amplified by the primer pair of SEQ ID NOs: 28 and 29, and "(vii) the primer pair of SEQ ID NOs: 30 and 31 for amplifying the genomic DNA encoding a cytolethal distending toxin of *Campylobacter fetus* (primers used in the Examples herein: Cf-CdtBU6 and Cf-CdtBR3), or a primer pair capable of amplifying the same genomic DNA region amplified by the primer pair of SEQ ID NOs: 30 and 31". Thus, primers that are individually specific to each of the six species, *C. hyointestinalis, C. upsaliensis, C. lari, C. jejuni, C. fetus*, and *C. coli*, are all comprised in the kits of the present invention, allowing simultaneous detection of mixed infection with the above-described *Campylobacter* bacteria by multiplex PCR or the like.

Another embodiment of the detection methods of the present invention includes methods for detecting the presence of *Campylobacter hyointestinalis* in a test sample, which comprise the steps of:
(a) contacting a test sample with an antibody that binds to a polypeptide of the present invention;

(b) measuring the binding between the test sample and the antibody that binds to the polypeptide of the present invention; and (c) determining that *Campylobacter hyointestinalis* is present if the binding is detected in (b).

The detection methods may use antibodies prepared by the above-described methods. Methods for measuring the binding between a test sample and an antibody that binds to a polypeptide of the present invention include the methods of Western blotting, dot blotting, immunoprecipitation, enzyme-linked immunosorbent assay (ELISA), and immunofluorescence. The presence of *Campylobacter hyointestinalis* in a test sample can be tested by detecting the cytolethal distending toxin of *Campylobacter hyointestinalis* in the test sample using these methods.

Furthermore, the above-described antibodies can be combined with other materials into kits to be used in the detection methods of the present invention. Such kits may comprise distilled water, salts, buffers, protein stabilizers, preservatives, and the like, in addition to the above-described antibodies and detection reagents. Alternatively, to prepare ELISA reagents, the antibodies can be combined with chromogenic substrates for detecting enzyme labels and wash solutions for washing the solid phase. Furthermore, manuals describing the assay procedures can be appended to the kits.

All prior art documents cited herein are incorporated into this specification by reference.

EXAMPLES

Hereinbelow, the present invention is specifically described with reference to the Examples; however, it should not be construed as being limited thereto.

Example 1

Sequencing of the cdt Genes of the Thai-Derived *C. hyointestinalis* Ch022 Strain The genomic gene was isolated from the Ch022 strain by a conventional method.

100 ng of the isolated Ch022 genomic gene was subjected to PCR using an Ex Taq PCR kit (TaKaRa) and common primers capable of amplifying the cdtB gene of *C. jejuni, C. coli*, and *C. fetus* (FIG. 1). The concentration of each primer was 0.5 µM. The primers were mixed with 5 µl of 10×Ex Taq buffer, 4 µl of dNTPs, and 1.25 U of Ex Taq. The volume was adjusted to 50 µl with sterile water. The PCR mixture was subjected to PCR with a program consisting of 30 cycles of 94° C. for 30 seconds, 50° C. for 30 seconds, and 72° C. for 30 seconds. The resulting PCR product was electrophoresed on a 2% agarose gel, and it was stained with ethidium bromide. After destaining, the amplification bands were observed under UV light (FIG. 1).

The obtained 720-bp band specifically amplified was purified by a conventional method, and sequenced using the common primers. The sequencing was performed using the Big-Dye terminator kit ver. 1.1 (Applied Biosystems) according to the manual.

Genome walking primers were designed based on the determined sequence. The full-length gene sequence of 4,069 bp covering the cdt gene (SEQ ID NO: 5) was determined by multiple rounds of upstream and downstream genome walking. Furthermore, ORFs of the cdtA, cdtB, and cdtC gene of the *C. hyointestinalis* Ch022 strain were found to be 798 bp (266 aa; SEQ ID NO: 6), 804 bp (268 aa; SEQ ID NO: 7), and 537 bp (178 aa; SEQ ID NO: 8) in length, respectively. These sequences were compared to the nucleotide sequences of the cdtA, cdtB, and cdtC genes of *C. jejuni, C. coli*, and *C. fetus*. The cdtA and cdtC genes of *C. hyointestinalis* exhibited the highest homology to those of *C. jejuni*, while the cdtB gene of *C. hyointestinalis* showed the highest homology to that of *C. coli* (Table 1). Meanwhile, homology comparison of the deduced amino acid sequences of CdtA, CdtB, and CdtC revealed that the three subunits of *C. hyointestinalis* showed the highest homology to the Cdt subunits of *C. coli*. The homology was 35.7%, 60.5%, and 28.9% for CdtA, CdtB, and CdtC, respectively (Table 1).

TABLE 1

|  | Nucleotide (%) | | | Amino acid (%) | | |
| --- | --- | --- | --- | --- | --- | --- |
|  | cdtA | cdtB | cdtC | CdtA | CdtB | CdtC |
| *C. jejuni* | 51.7 | 63.8 | 52.5 | 35.7 | 60.5 | 28.9 |
| *C. coli* | 51.0 | 64.1 | 42.6 | 40.9 | 61.6 | 29.8 |
| *C. fetus* | 46.1 | 59.7 | 43.0 | 30.2 | 56.2 | 26.2 |

The insertion position of the cdt genes of *C. hyointestinalis* was different from that of *C. jejuni, C. coli*, and *C. fetus*. An ORF that has a homology of 53.6% (128 aa/239 aa) to *Helicobacter* glycosyl transferase was found upstream of the cdtA gene. Meanwhile, an ORF that has a homology of 56.0% (155 aa/277 aa) to *T. denitrificans* sugar transferase was found downstream of the cdtC gene. Furthermore, the deduced amino acid sequence of *C. hyointestinalis* CdtB has conserved amino acid residues that are reported to be essential for the DNase activity of CdtB produced by other bacterial species (Yamasaki S, et al., 2006. Toxin Rev, 25, 61-88.) (FIG. 2).

Example 2

Preparation of Recombinant CdtB Protein (Ch-rCdtB) of the Thai-Derived *C. hyointestinalis* Ch022 Strain The cdtB gene of the Thai-derived *C. hyointestinalis* Ch022 strain, in which amino acids 1-17 of CdtB which is predicted to be the CdtB signal sequence was removed, was amplified by PCR and cloned into the pET-28(a) plasmid vector to obtain pWSY-2, a recombinant clone of the cdtB gene of the Thai-derived *C. hyointestinalis* Ch022 strain.

Figure 3:
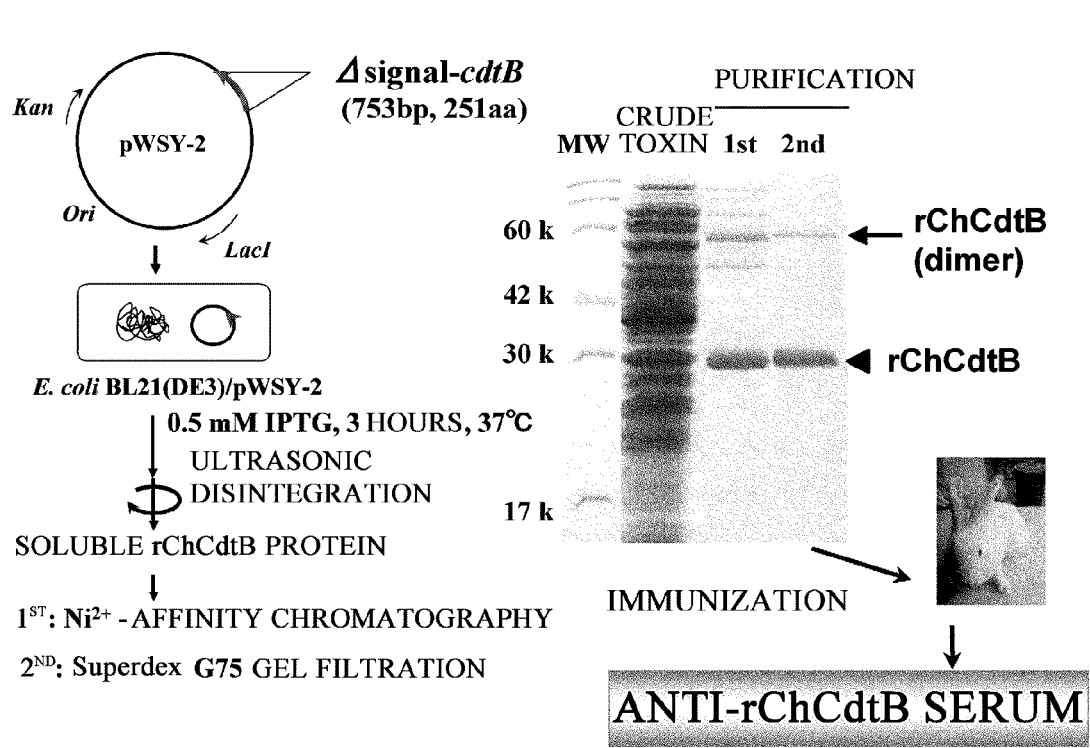
FIG. 3 presents a diagram and a photograph showing preparation of recombinant *C. hyointestinalis* CdtB and an antiserum.

BL-21(DE3) which is an *E. coli* for recombinant protein expression (Novagen) was transformed with pWSY-2. The resulting clone was cultured on a large scale in 600 ml of LB broth containing 20 µg/ml kanamycin, and then expression of the recombinant protein (Ch-rCdtB) was induced with 0.5 mM IPTG at 37° C. for three hours. The Ch-rCdtB-expressing *E. coli* was disintegrated by ultrasonication. The protein was affinity-purified with Ni-Chelating Sepharose (GE Healthcare), and further purified by gel filtration with Superdex 75 (GE Healthcare) (FIG. 3).

Example 3

Figure 4:
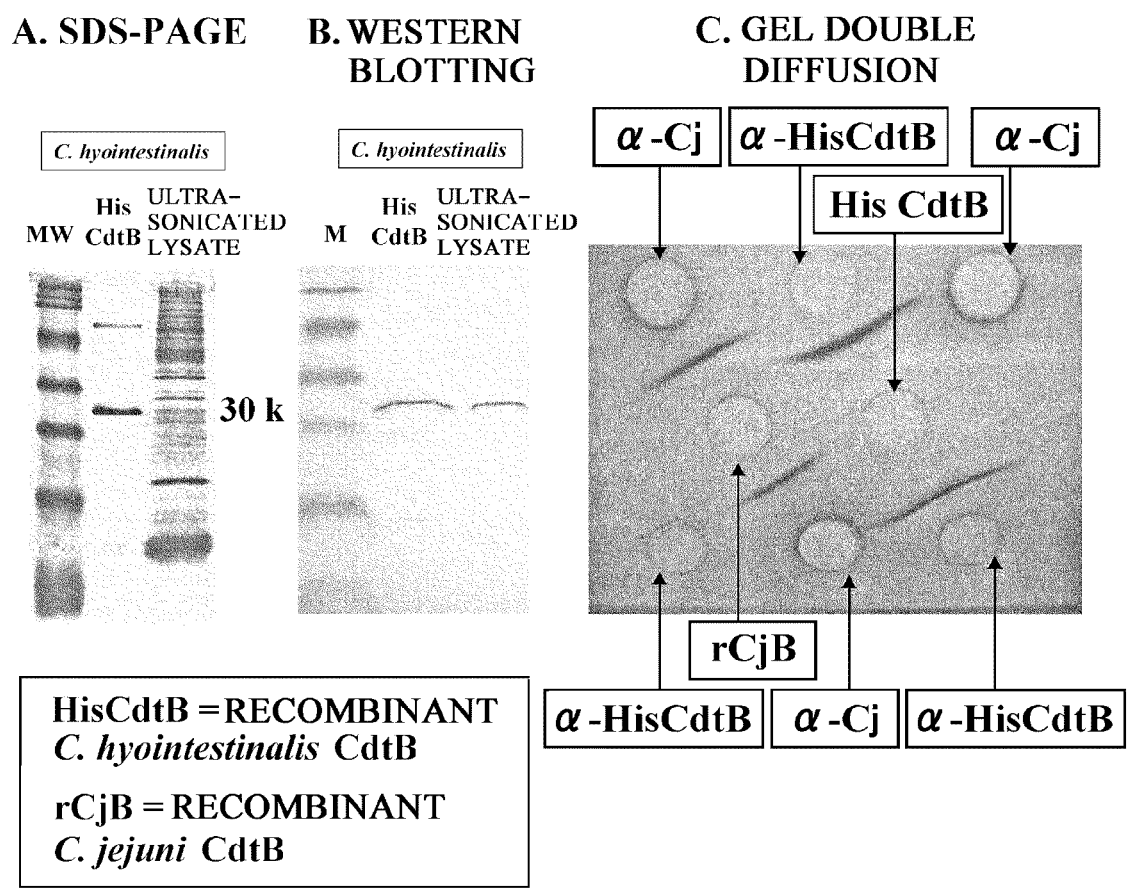
FIG. 4 presents photographs showing the specificity of the anti-His CdtB antiserum.

Preparation of an Antibody Against CdtB of the Thai-Derived *C. Hyointestinalis* Ch022 Strain 250 µg of purified Ch-rCdtB was combined with an equal volume of Freund's complete adjuvant. The resulting emersion was administered subcutaneously and intramuscularly to rabbits (kbs: NZW). Then, starting four weeks after the first administration, the rabbits were immunized five times in total with an emersion containing 250 µg of purified Ch-rCdtB and an equal volume of incomplete Freund's adjuvant at two-week intervals for about eight weeks. An antiserum was thus prepared, and then tested for its titer and specificity by the gel double diffusion method and Western blotting (FIG. 4).

The titer of the anti-Ch-rCdtB antiserum was estimated to be 1:64 by the gel double diffusion method. Meanwhile, there was no precipitate line between the antibody and *C. jejuni* rCdtB. Thus, it was revealed that *C. hyointestinalis* CdtB was immunologically distinct from *C. jejuni* CdtB (FIG. 4C). Western blotting was carried out using purified Ch-rCdtB and a crude toxin solution from the *C. hyointestinalis* Ch022 strain. The antibody reacted specifically with bands corresponding to purified Ch-rCdtB (molecular weight of about 30 kD) and CdtB in the crude toxin solution from the *C. hyointestinalis* Ch022 strain. Thus, it suggests that the specificity of the prepared antibody to Ch-rCdtB was very high (FIG. 4B).

Example 4

Sequencing of the cdt Genes of *C. hyointestinalis* ATCC 35217

The genomic gene was isolated from the *C. hyointestinalis* ATCC 35217 strain by a conventional method.

Figure 5:
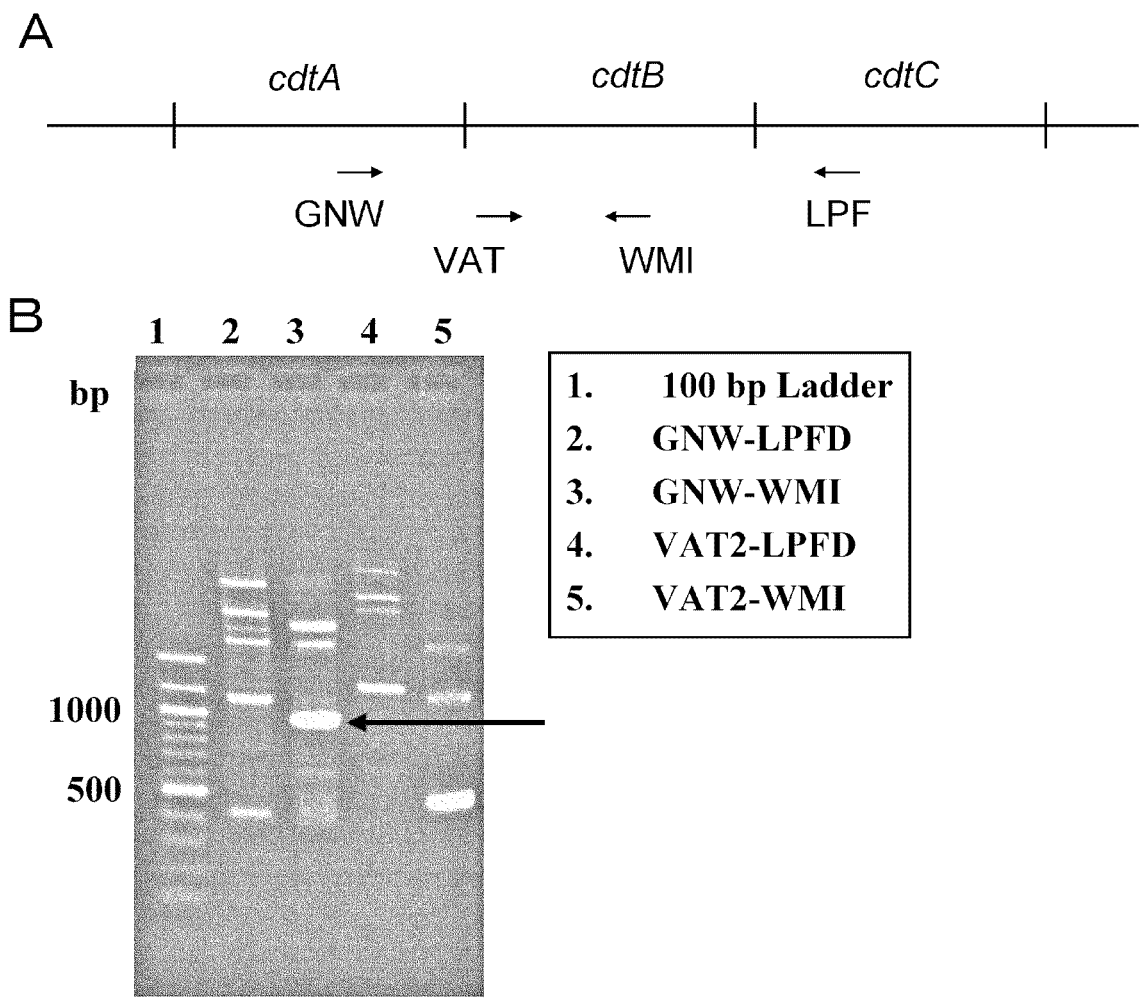
FIG. 5 presents a diagram and a photograph showing amplification of the cdt genes of the *C. hyointestinalis* ATCC strain using degeneration primers.

100 ng of the isolated genomic gene of *C. hyointestinalis* ATCC 35217 was subjected to PCR using the degeneration primers (GNW and WMI) and an Ex Taq PCR kit (TaKaRa) (FIG. 5). The concentration of each primer was 0.5 µM. The primers were mixed with 5 µl of 10×Ex Taq buffer, 4 µl of dNTPs, and 1.25 U of Ex Taq. The volume was adjusted to 50 µl with sterile water. The PCR mixture was subjected to PCR with a program consisting of 30 cycles of 94° C. for 30 seconds, 42° C. for 30 seconds, and 72° C. for 60 seconds. The resulting PCR product was electrophoresed on a 1.5% agarose gel, and it was stained with ethidium bromide. After destaining, the amplification bands were observed under UV light (FIG. 5).

The specifically amplified 960-bp band obtained was purified by a conventional method, and cloned into the pT7Blue plasmid vector (Novagen) to obtain pChATcdtA-B4. The resulting pChATcdtA-B4 plasmid was sequenced using M13 primers, which hybridize with the plasmid. Sequencing was performed using the BigDye terminator kit ver. 1.1 (Applied Biosystems) according to the manual.

The determined sequence was subjected to homology search by BLAST. It was shown that the sequence has homology to portions of the cdtA and cdtB genes.

Genome walking primers were designed based on the determined sequence. The full-length gene sequence of 3,399 bp covering the cdt genes (SEQ ID NO: 1) was determined by multiple rounds of upstream and downstream genome walking. Furthermore, the ORFs of CdtA, CdtB, and CdtC were identified. The amino acid sequences of CdtA, CdtB, and CdtC are shown in SEQ ID NOs: 2, 3, and 4, respectively.

Example 5

CTD Activity Assay Using HeLa Cells

Common to the Thai and ATCC Strains

Figure 6:
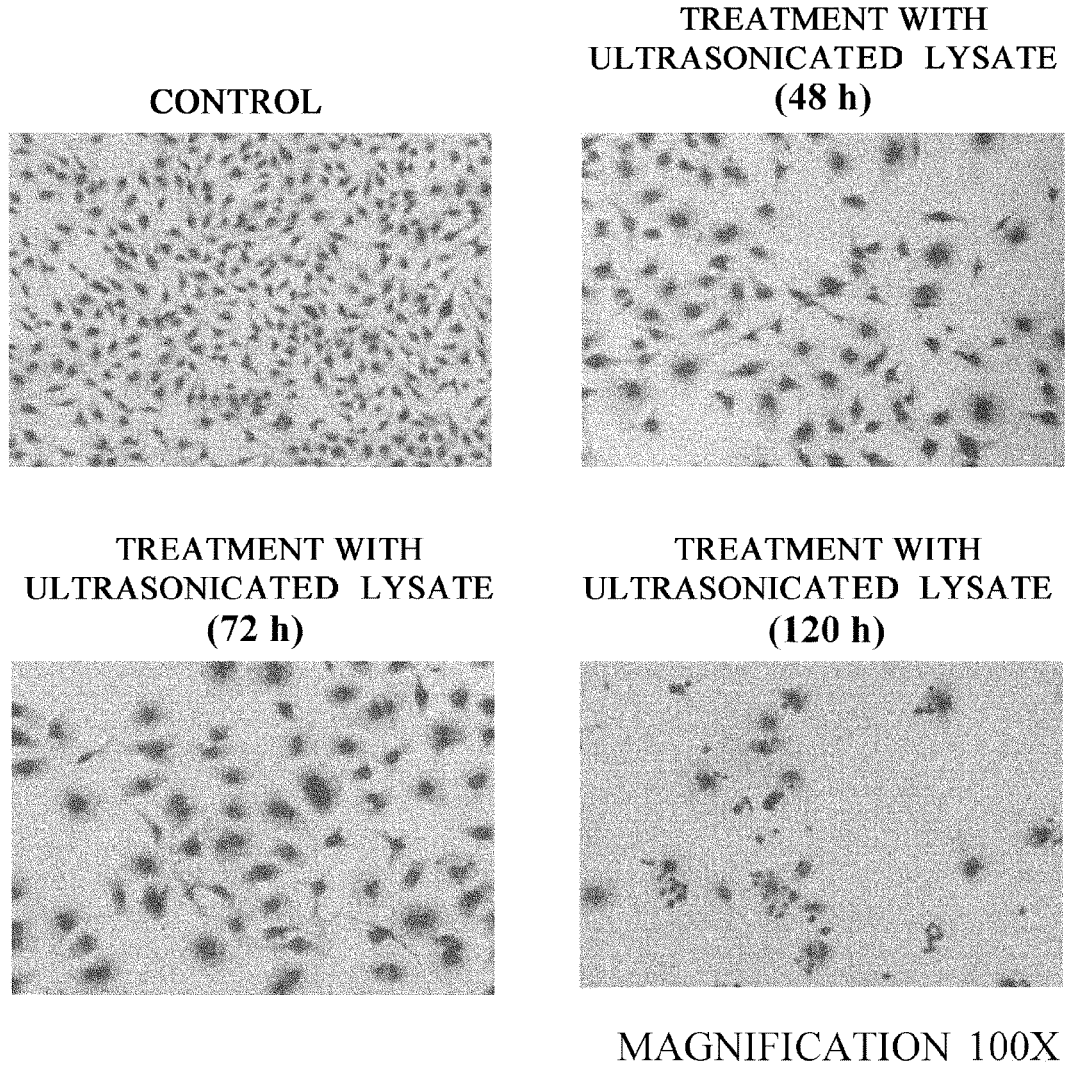
FIG. 6 presents photographs showing the result of assaying the toxic activity of a crude toxin solution from *C. hyointestinalis* towards HeLa cells after 48, 72, and 120 hours.
Figure 7:
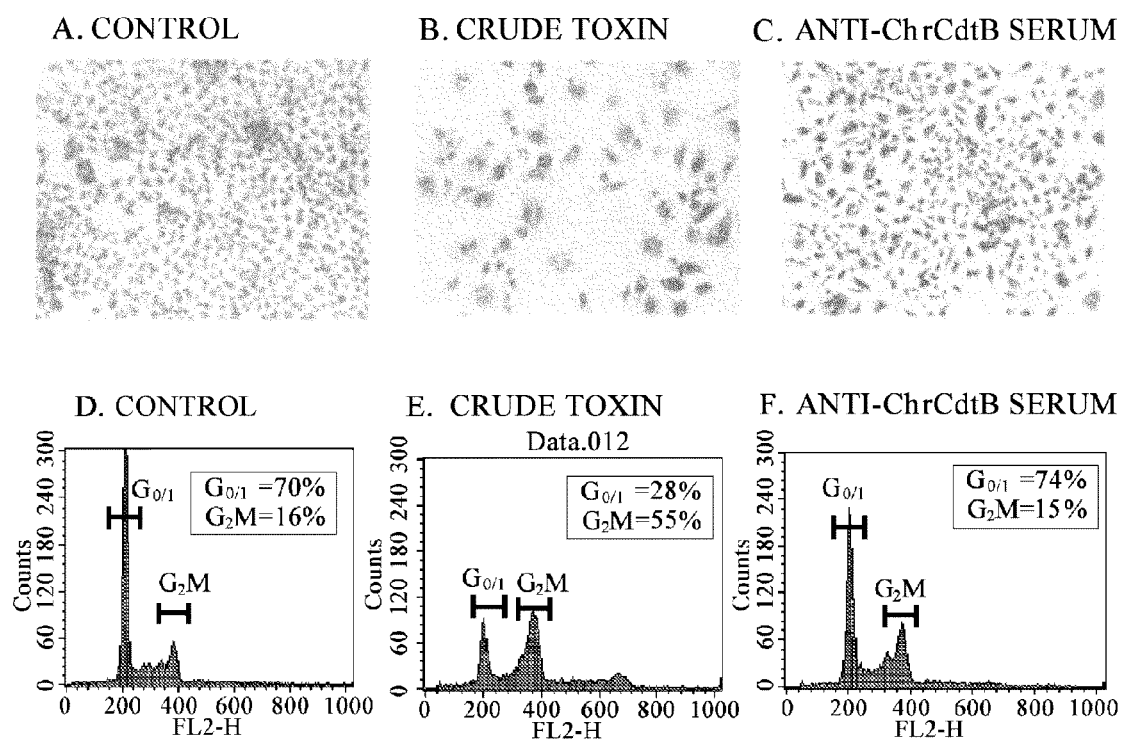
FIG. 7 presents photographs and diagrams showing the result of assaying the toxic activity of a crude toxin solution from *C. hyointestinalis* towards HeLa cells.

The *C. hyointestinalis* Ch022 and ATCC 35217 strains were cultured on horse blood agar media under microaerophilic conditions (5% $CO_2$, 10% $O_2$, and 85% $N_2$) at 37° C. for 48 hours. The resulting bacterial cells were suspended in MEM at an $OD_{600}$ of 1.0, and disintegrated by ultrasonication. After centrifugation, the supernatants were sterilized by filtration using membrane filters (pore size 0.22 µm). The prepared crude toxin solution samples were serially diluted, and added to HeLa cells. Changes in cell morphology were observed after 48 and 120 hours (FIG. 6). For the Thai strain, the specificity of the CDT activity was assessed by simultaneously adding an anti-Ch-rCdtB antiserum to the strain. Furthermore, after 48 hours, the cellular DNA content was quantified using a flow cytometer (FIG. 7). The titer of the toxin was defined as the maximum dilution factor of the crude toxin solution that provides distention of 50% or more cells.

The crude toxin solution from *C. hyointestinalis* was added to HeLa cells, and exhibited cell distending activity after 48 hours and cytolethal activity after 120 hours up to 16× dilution (FIG. 6). These activities were neutralized by the anti-Ch-rCdtB serum. Furthermore, the cellular DNA content was quantified 48 hours after addition of the crude toxin solution using a flow cytometer. The result clearly showed that the cells were arrested in G2/M phase. In the negative control which does not have added crude toxin solution, or when both the crude toxin solution and the anti-Ch-rCdtB serum were added to the cells, a high peak corresponding to G0/G1 but not the G2/M phase arrest was observed (FIG. 7).

The results described above demonstrated that *C. hyointestinalis* produces CDT which has toxin activity. The toxin activity was attributed to the CDT, since it was neutralized by the anti-Ch-rCdtB antiserum.

Example 6

Media, Culture Conditions and Reagents for *Campylobacter* Bacteria

*Campylobacter* bacteria were cultured using horse blood agar media containing CM271 BLOOD AGAR BASE No. 2 (OXOID; Basingstoke, UK) [7.5 g of Protease Peptone, 1.25 g of liver digest, 2.5 g of yeast extract, 2.5 g of sodium chloride, 6.0 g of agar/500 ml of DW, pH 7.4±0.2 at 25° C.] supplemented with 5% sterile defibrinated horse blood (Nippon Bio-Supp. Center, Tokyo). For *Campylobacter concisus* (hereinafter abbreviated as "*C. concisus*"), 0.25 ml of a solution containing 6% sodium formate and 6% fumaric acid was further applied to each plate. *Campylobacter* bacteria were cultured at 37° C. for two to four days under microaerophilic conditions (10% $CO_2$, 5% $O_2$, and 85% $N_2$) using a LOW TEMPERATURE $O_2/CO_2$ INCUBATOR MODEL-9200 (WAKENYAKU, CO., LTD.). *C. concisus* was cultured under the anaerobic conditions of 10% $CO_2$, 10% $H_2$, and 80% $N_2$ for three to seven days.

*E. coli* was cultured at 37° C. for 16 to 20 hours in liquid LB-Lenox medium (5.0 g of Bacto tryptone, 2.5 g of Bacto yeast extract, 2.5 g of NaCl/500 ml of DW; Difco Laboratories, USA) or LB-Lenox agar medium (5.0 g of Bacto tryptone, 2.5 g of Bacto yeast extract, 2.5 g of NaCl, 7.5 g of agar/500 ml of DW; Difco Laboratories).

All other reagents were purchased from Nacalai Tesque, Wako Pure Chemical Industries, or Sigma Chemical Co. (St. Louis, Mo., USA). Restriction enzymes, Takara Ex Taq, and Multiplex PCR assay Kit were purchased from Takara Bio. Seakem GTG agarose, an agarose for electrophoresis, was purchased from Takara Bio. Molecular weight markers were purchased from New England Biolabs (USA).

Example 7

PCR and Preparation of PCR Template DNAs

Colonies were scraped off plates, and added to 200 µA of a TE solution. The suspension was heated for ten minutes. After the heat treatment, the suspension was centrifuged at 12,800×g for ten minutes. The resulting supernatant was collected and used as a template DNA. The *E. coli* C600 strain was used as a negative control.

All PCR experiments were carried out using GeneAmp PCR System 2400 (PerkinElmer) or GeneAmp PCR System 9700 (PerkinElmer). Agarose gel electrophoresis was carried out using a MUPID (ADVANCE) at 100 V in 1×TAE Buffer [40 mM Tris-acetate (pH 8.5), 1 mM EDTA]. After electrophoresis, the gel was stained with 1.0 µg/ml ethidium bromide (Sigma) for 15 minutes. After destaining with DW, the PCR products were analyzed and photographed under ultraviolet light (260 nm) using a gel documentation system, Gel Doc 2000 (Bio-Rad).

Example 8

PCR for the cdtB Gene of the *C. Hyointestinalis* ATCC and Thai-Derived Ch022 Strains Using Common cdtB Gene Primers for *C. Jejuni, C. Coli*, and *C. Fetus*, or cdtB Gene Primers for the ATCC Strain The cdt genes of *C. hyointestinalis* were sequenced and compared to the cdt gene sequences of other *Campylobacter* bacterial species. The result showed that there were several mutations (marked red) in the binding sites of the common primers for the cdtB gene of *C. jejuni, C. coli*, and *C. fetus* (FIG. 8). When the common primers for the cdtB gene of *C. jejuni, C. coli*, and *C. fetus* were used, PCR yielded a weaker amplified band or no band from the *C. hyointestinalis* ATCC strain as compared to other bacterial species. The 3'-end region homology is particularly important for PCR primers. However, several mutations were found in the 3'-end regions of the primer binding sites in the cdtB gene of the *C. hyointestinalis* ATCC strain (FIG. 8). Mutations in the primer binding sites, in particular the 3'-end region, are thought to be responsible for the inconstant PCR amplification of the cdtB gene of the *C. hyointestinalis* ATCC strain. Thus, common cdtB gene primers were designed for the *C. hyointestinalis* ATCC strain, and compared with the conventional common primers by PCR Bacterial Strains:
 *C. hyointestinalis* ATCC35217 strain
 *C. hyointestinalis* Ch022 strain
Common Primers:

```
ComBU: 5'-ACTTGGAATTTGCAAGGC-3'    (SEQ ID NO: 14)

ComBR: 5'-TCTAAAATTTACHGGAAAATG-3' (SEQ ID NO: 15)
```

Primers for the ATCC Strain:

```
ChATcomBU:
5'-ACTTGGAATATGCAAGGA-3'           (SEQ ID NO: 16)

ChATcomBR:
5'-CCAAATGTTATAGGAAAGTG-3'         (SEQ ID NO: 17)
```

PCR:
1 µl of PCR template prepared from each bacterial strain by the boil method was mixed with the primers (final concentration: 1 µM), TaKaRa Ex taq (0.25 U), dNTPs (200 µM each), and 10×Ex Taq Buffer. PCR was carried out at a total volume of 40 µl. The PCR conditions were as follows: 94° C. for three minutes, and 30 cycles of 94° C. for 30 seconds, 50° C. for 30 seconds, and 72° C. for 30 seconds, followed by 72° C. for five minutes.

Figure 9:
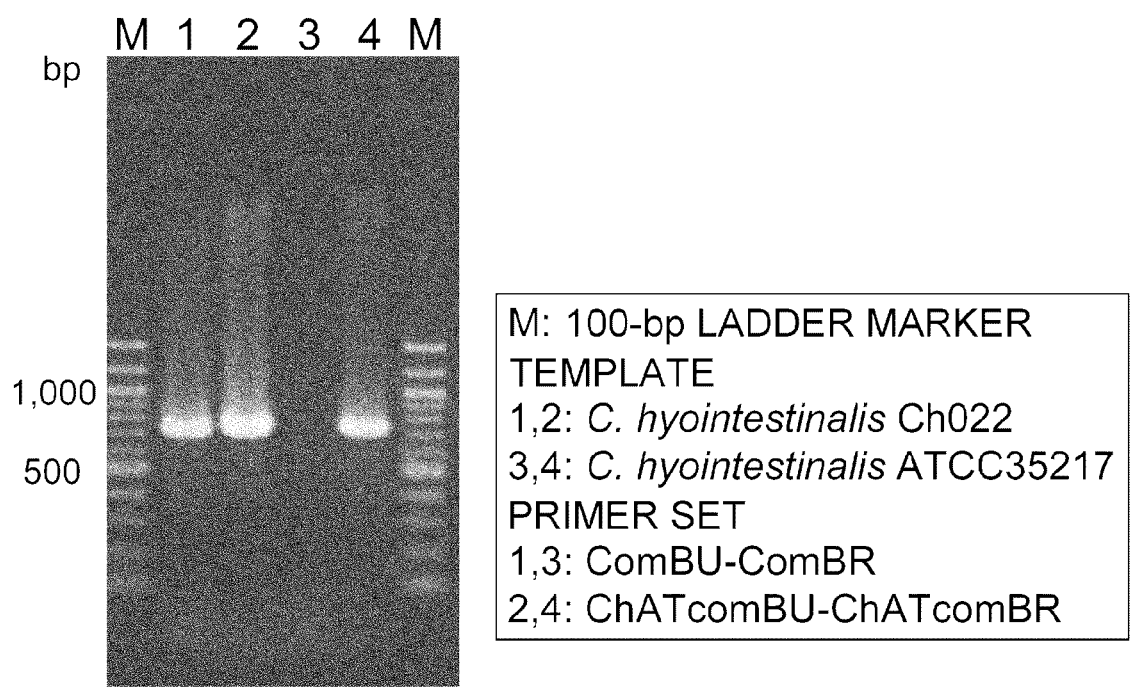
FIG. 9 presents a photograph showing PCR results for the cdtB gene of the *C. hyointestinalis* ATCC and Thai-derived Ch022 strains.

Results:
The common cdtB gene primers for *C. jejuni, C. coli*, and *C. fetus* allowed amplification in the Thai-derived *C. hyointestinalis* Ch022 strain but not the *C. hyointestinalis* ATCC35217 strain. Meanwhile, the primers for the ATCC strain allowed amplification in both the *C. hyointestinalis* Thai-derived Ch022 and ATCC35217 strains (FIG. 9).

Example 9

PCR for Detection of a Broad Range of *Campylobacter* Bacteria Including the *C. hyointestinalis* ATCC and Thai-Derived Ch022 Strains The common cdtB gene primers for *C. jejuni, C. coli*, and *C. fetus* provided only a weakly amplified band in previous experiments, and no detectable band in the experiment described herein for the *C. hyointestinalis* ATCC35217 strain. Thus, PCR was carried out using newly designed common primers for a more stable amplification of the *C. hyointestinalis* cdtB gene.

Primers:

```
cdtB CommonU:
5'-ACTTGGAATWTGCAAGGM-3'    (SEQ ID NO: 18)

cdtB CommonR:
5'-CYAAAWKTTAYHGGAAARTG-3'  (SEQ ID NO: 19)
```

(W: A or T; M: A or C; Y: C or T; K: G or T; H: A, C, or T; R: A or G)

Bacterial Strains:
 *C. jejuni* 81-176 strain
 *C. coli* Col-243 strain
 *C. fetus* Col-187 strain
 *C. lari* ATCC43675 strain
 *C. upsaliensis* ATCC43954 strain
 *C. hyointestinalis* ATCC35217 strain
 *C. hyointestinalis* Ch022 strain
 *C. helveticus* ATCC51209 strain
 *E. coli* C600 strain PCR:
1 µl of PCR template prepared from each bacterial strain by the boil method was mixed with the primers (final concentration: 1 µM), TaKaRa Ex taq (0.25 U), dNTPs (200 µM each), and 10×Ex Taq Buffer. PCR was carried out at a total volume of 40 µl. The PCR conditions were as follows: 94° C. for three minutes, and 30 cycles of 94° C. for 30 seconds, 50° C. for 30 seconds, and 72° C. for 30 seconds, followed by 72° C. for five minutes.

Figure 10:
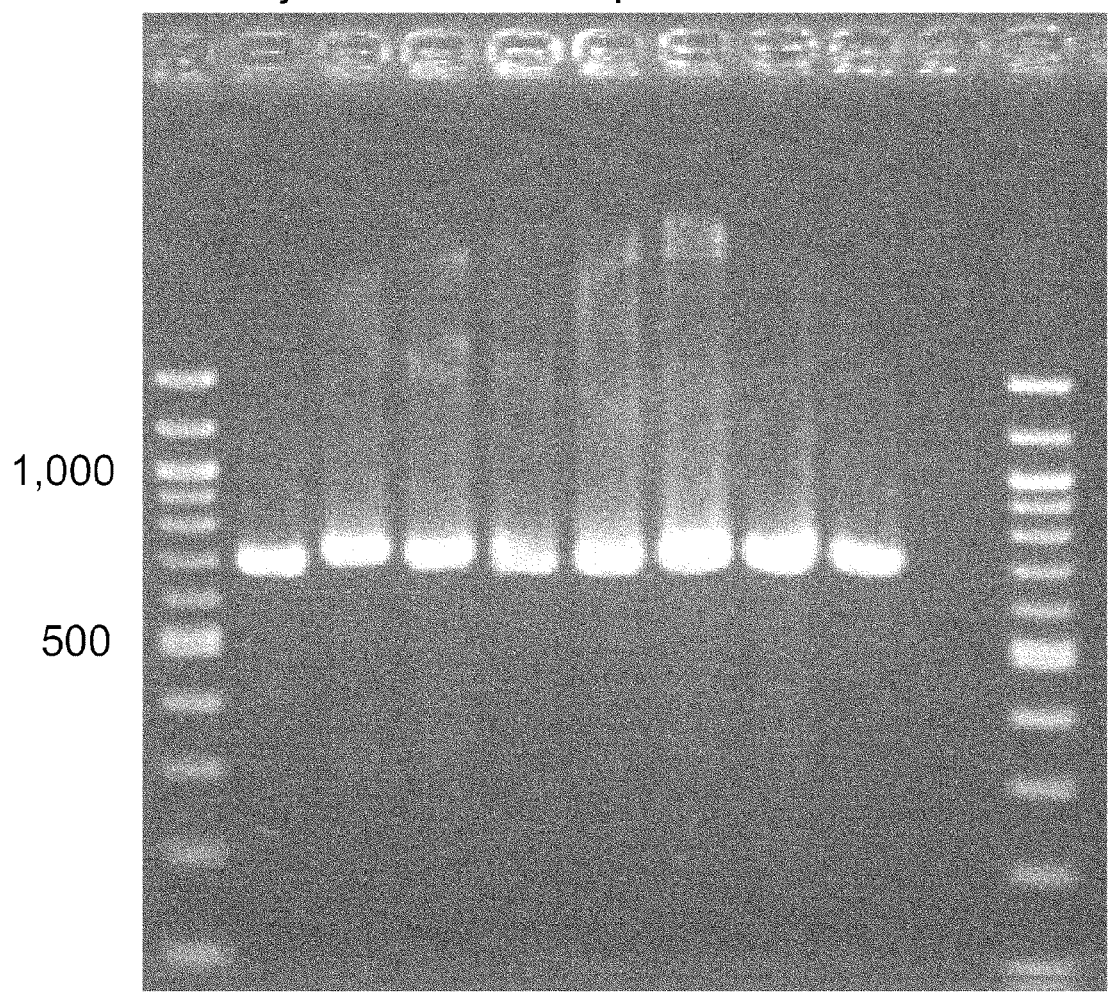
FIG. 10 presents a photograph showing PCR results of using common primers for the cdtB gene.

Results:
Efficient PCR amplification of the bands was observed for all the bacterial strains used (FIG. 10).

Example 10

Estimation of the cdtB Gene Copy Number of the *C. Hyointestinalis* ATCC and Thai-Derived Ch022 Strains by Southern Hybridization Both of the conventional common primers and the newly designed primers for the *C. hyointestinalis* ATCC35217 strain allowed amplification in the *C. hyointestinalis* Ch022 strain. This suggested that the *C. hyointestinalis* Ch022 strain has two copies of the cdtB gene. Thus, the cdtB gene copy number of the *C. hyointestinalis* ATCC and Thai-derived Ch022 strains was assessed by Southern hybridization using probes that are specific to each strain.

Bacterial Strains:
- *C. jejuni* 81-176 strain
- *C. hyointestinalis* ATCC35217 strain
- *C. hyointestinalis* Ch022 strain Primers:

```
cdtB probes for the C. hyointestinalis Ch022
strain
ComBU:
5'-ACTTGGAATTTGCAAGGC-3'        (SEQ ID NO: 14)

ComBR:
5'-TCTAAAATTTACHGGAAAATG-3'     (SEQ ID NO: 15)

cdtB probes for the C. hyointestinalis ATCC strain
ChATcomBU:
5'-ACTTGGAATATGCAAGGA-3'        (SEQ ID NO: 22)

ChATcomBR:
5'-CCAAATGTTATAGGAAAGTG-3'      (SEQ ID NO: 23)
```

Probe Preparation:

PCR templates were prepared from the bacterial strains by the boil method. 1 μl of each template was mixed with the primers for the bacterial strain (final concentration: 0.5 μM), TaKaRa Ex taq (0.25 U), digoxigenin-labeled dNTPs (Roche Diagnositics) (200 μM each), and 10×Ex Taq Buffer. PCR was carried out at a total volume of 40 μl. The PCR conditions were as follows: 94° C. for three minutes, and 30 cycles of 94° C. for 30 seconds, 50° C. for 30 seconds, and 72° C. for 30 seconds, followed by 72° C. for five minutes.

The resulting PCR products were electrophoresed on a 1.5% agarose gel, and it was stained with ethidium bromide. After destaining, the detected bands were excised and purified using a Qiagen PCR purification kit (Qiagen), and this was used as a probe.

Preparation and Restriction Enzyme Digestion of Chromosomal Genomic DNA:

The chromosomal genomic DNA was purified using an ISOPLANT Kit (NIPPON GENE). Bacterial cells were scraped off plates, and about 30 mg of the cells were suspended in 150 μl of extraction buffer, and lysed by adding 300 μl of lysis buffer. After 15 minutes of incubation at 50° C., 150 μl of sodium acetate buffer (pH 5.2) was added, and this was allowed to stand on ice for 15 minutes. The aqueous layer was subjected to ethanol precipitation. The precipitate was dissolved in TE [10 mM Tris-HCl (pH 8.0), 1 mM EDTA], and this was used as a DNA solution.

The DNAs were quantified using a spectrophotometer. 1 μg of each genomic DNA was digested with EcoRV or DraI (20 U) at a final volume of 50 μl at 37° C. for five hours.

Southern Hybridization:

The enzyme-digested bacterial genomes were electrophoresed on a 1.5% agarose gel, and then it was stained with ethidium bromide. After destaining, the genomic DNAs were confirmed to be digested with the restriction enzymes. Next, the gel was treated with 0.25 N HCl for 15 minutes. After washing twice with DW, the gel was treated with 0.5 N NaOH for 30 minutes. The DNAs were transferred from the gel onto a nylon membrane using 10×SSC in a Vacuum Blotter for 90 minutes. 2 ml of prehybridization buffer [50% formamide, 5×SSC, 0.01% SDS, 1 mM EDTA, Denhardt's solution, 0.02% BSA, 100 μg/ml heat-denatured herring sperm DNA] was added to each nylon membrane. The membrane was incubated at 42° C. for one hour. Then, the cdtB probes for the *C. hyointestinalis* Ch022 or ATCC strain were heat-denatured and added at 25 ng/ml to the nylon membrane in a hybridization buffer. The nylon membrane was incubated at 42° C. overnight, and then washed twice with 2×SSC containing 0.1% SDS at room temperature for 15 minutes, and twice with 0.1×SSC containing 0.1% SDS at 65° C. for 30 minutes. Then, the nylon membrane was washed for two minutes with washing buffer [0.1 M Tris-HCl (pH 7.5), 0.15 M NaCl, 0.3% Tween 20], and then equilibrated with blocking buffer (Buffer 1 [0.1 M Tris-HCl (pH 7.5), 0.15 M NaCl], 1× Blocking stock solution) at room temperature for 30 minutes. An anti DIG-Alkaline Phosphatase conjugate (7,500 U/ml) was diluted 10,000-fold in fresh blocking buffer, and added to the nylon membrane. After 30 minutes of shaking at room temperature, the membrane was washed twice with Buffer 1 for 15 minutes, and equilibrated with AP9.5 buffer [0.1 M Tris-HCl (pH 9.5), 0.1 M NaCl, 50 mM $MgCl_2$] for five minutes. Finally, the chromogenic substrate solution NBT/BCIP diluted with AP9.5 buffer (4.5 μl of NBT, 3.5 μl of BCIP/1 ml of AP9.5 buffer) was added, and the membrane was incubated in the dark for color development at room temperature for 30 minutes.

Figure 11:
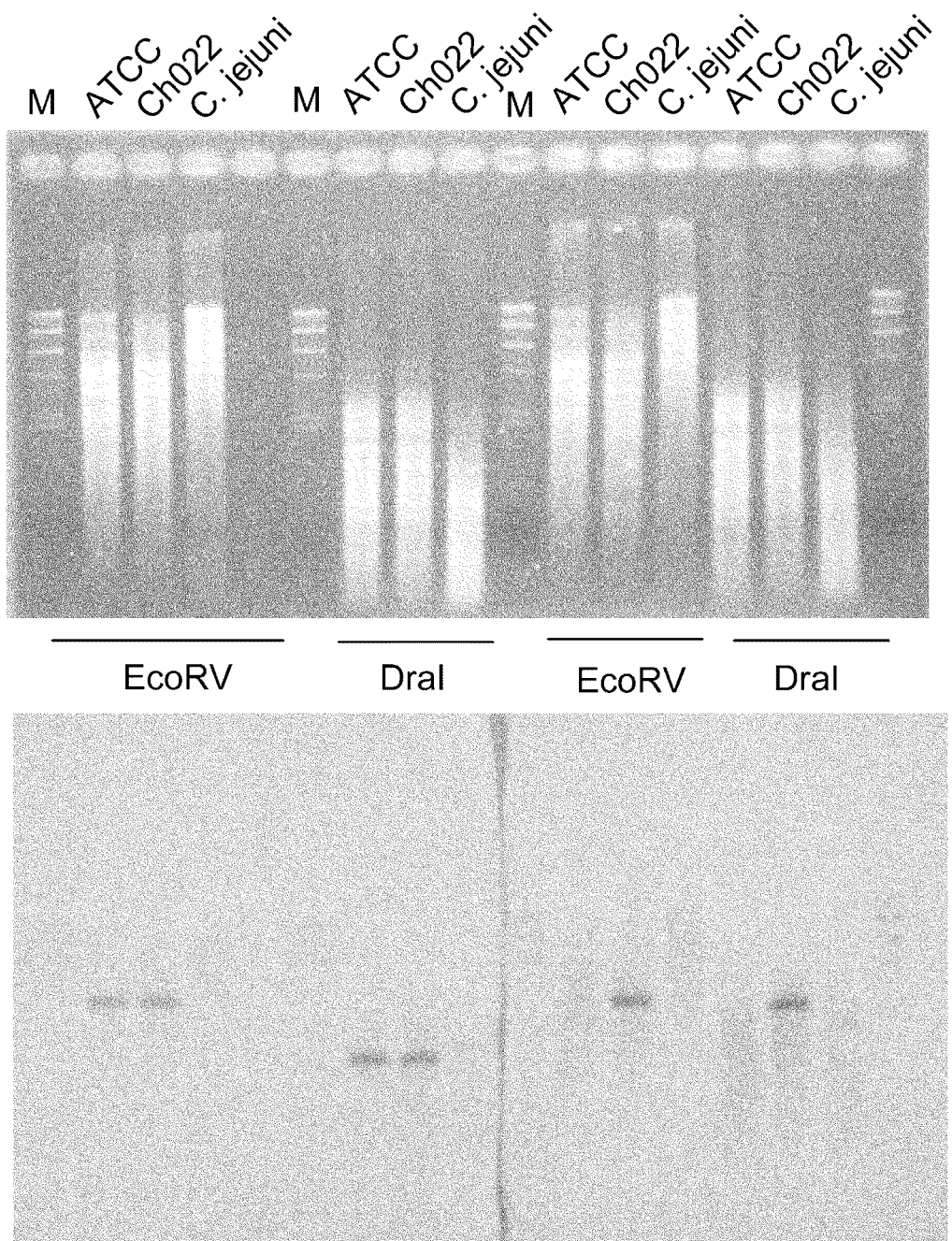
FIG. 11 presents a photograph showing PCR results of using common primers for the cdtB gene.

Results:

The chromosomal genomic DNAs of the *C. hyointestinalis* ATCC and Thai-derived Ch022 strains were digested with EcoRV, and subjected to Southern hybridization using the cdtB probes for the ATCC strain. As a result, the bands at the same position were detected in the two bacterial strains. Furthermore, when the other restriction enzyme (DraI) was used, the bands were also detected at the same position. Thus, it was suggested that the two bacterial strains have an ATCC strain type of cdtB gene homolog (hereinafter, "ATCC type") (FIG. 11). When Southern hybridization was carried out using the cdtB probes for the Thai-derived Ch022 strain, the band was detected only in the Thai-derived *C. hyointestinalis* Ch022 strain. Furthermore, when the DNA was digested with DraI, the position of the band detected with the cdtB probes for the ATCC strain was distinct from that of the band detected with the cdtB probes for the Ch022 strain (FIG. 11). Thus, it was suggested that the Thai-derived *C. hyointestinalis* Ch022 strain has the following two copies of the cdtB gene: an ATCC-type cdtB gene and a cdtB gene homolog of the Thai-derived Ch022 strain (hereinafter referred to as "Thai-type").

Example 11

PCR Using Specific Primers for Detection of the *C. Hyointestinalis* ATCC-Type and Thai-Type cdtB Genes The cdtB gene was compared between the *C. hyointestinalis* ATCC and Thai strains. The regions specific to each strain were identified, and specific primers were designed based on the regions. PCR was carried out for several animal-derived *C. hyointestinalis* strains to assess whether they have the ATCC-type and Thai-type cdtB genes.

Primers specific to the *C. hyointestinalis* Thai-type cdtB gene:

```
Ch022spBU1:
5'-TATCAGGCAATAGCGCAG-3'        (SEQ ID NO: 20)

Ch022spBR1:
5'-GGTTTGCACCTACATCAAC-3'       (SEQ ID NO: 21)
```

Primers specific to the *C. hyointestinalis* ATCC-type cdtB gene:

```
ChATspBU2:
5'-CCTAGTAGCGCTACTTAG-3'    (SEQ ID NO: 22)

ChATspBR2:
5'-TACAAAGCTTGGGCGAAG-3'    (SEQ ID NO: 23)
```

Figure 12:
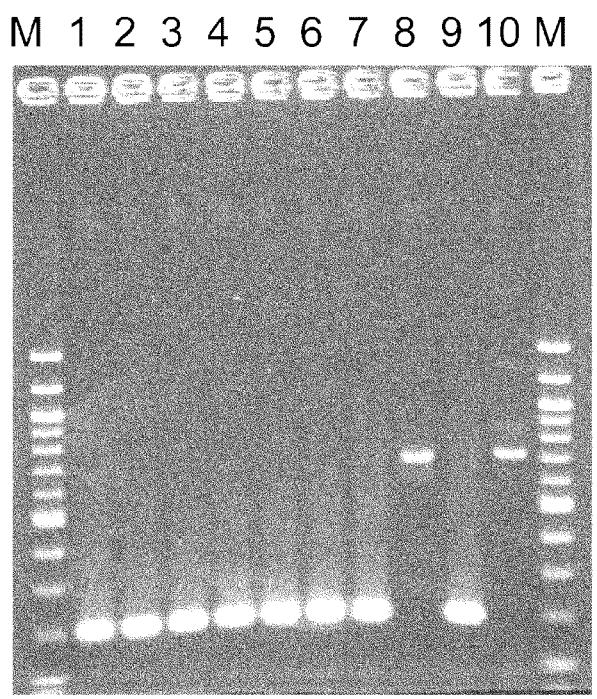
FIG. 12 presents a photograph showing PCR results of using specific primers for detection of the *C. hyointestinalis* Thai-type cdtB gene.
Figure 13:
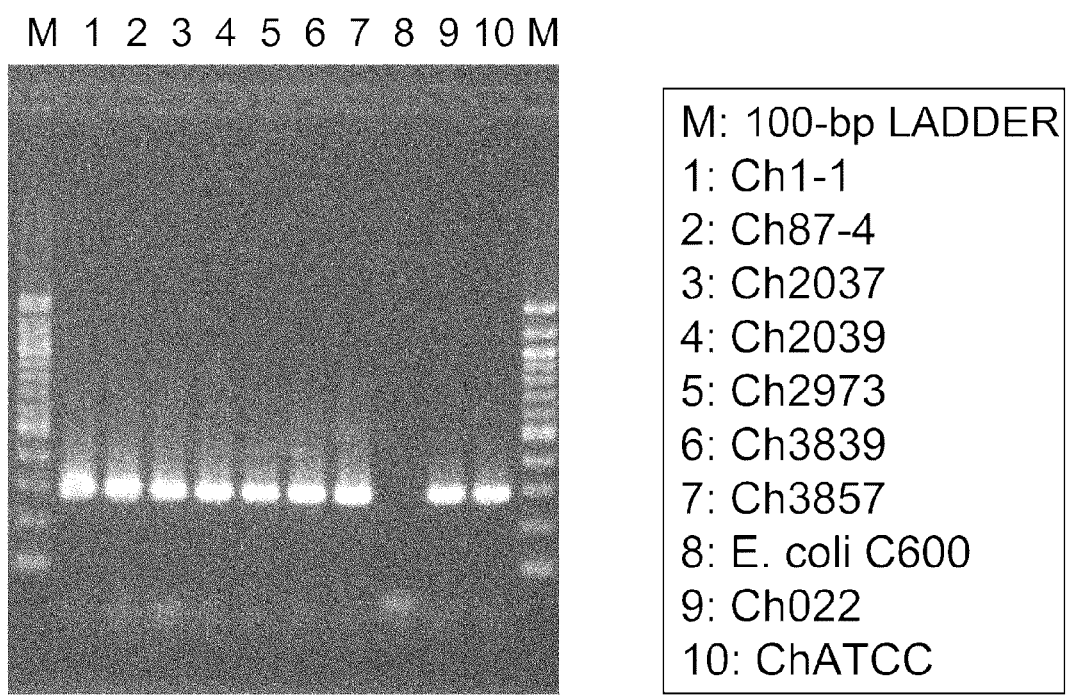
FIG. 13 presents a photograph showing PCR results of using specific primers for detection of the *C. hyointestinalis* ATCC-type cdtB gene.

Bacterial Strains:
*C. hyointestinalis* Ch1-1, Ch87-4, Ch2037, Ch2039, Ch2973, Ch3839, Ch3857, ATCC35217, Ch022
*E. coli* C600
PCR:
1 µl of PCR template prepared from each bacterial strain by the boil method was mixed with the specific primers (final concentration: 0.5 µM), TaKaRa Ex taq (0.25 U), dNTPs (200 µM each), and 10×Ex Taq Buffer. PCR was carried out at a total volume of 40 µl. The PCR conditions were as follows: 94° C. for three minutes, and 30 cycles of 94° C. for 30 seconds, 55° C. for 30 seconds, and 72° C. for 30 seconds, followed by 72° C. for five minutes. The resulting PCR products were electrophoresed on a 2% agarose gel. The gel was stained with ethidium bromide and then destained.
Results:
It was demonstrated that all of the seven *C. hyointestinalis* strains tested have both the Thai-type (FIG. 12) and ATCC-type (FIG. 13) cdtB genes. The ATCC strain alone did not have the Thai-type cdtB gene.

Example 12

PCR for the *C. hyointestinalis* ATCC-Type and Thai-Type cdtB Genes Using Common Primers The *C. hyointestinalis* ATCC-type and Thai-type cdtB genes were compared to each other. Common regions of the genes were identified, and common primers were designed based on these regions. The size of amplified product was designed to be compatible with the previously reported multiplex PCR which can detect *C. jejuni*, *C. coli*, and *C. fetus*. PCR was carried out for several animal-derived *C. hyointestinalis* strains to assess the primers.
Common primers for detection of the *C. hyointestinalis* ATCC-type and Thai-type cdtB genes:

```
ChspBU7:
5'-GTTCAAGAAGCAGGAAGC-3'    (SEQ ID NO: 24)

ChspBR7:
5'-AATACCWAKAATWGGTCTTG-3'  (SEQ ID NO: 25)

(W: A or T; K: G or T)
```

Figure 14:
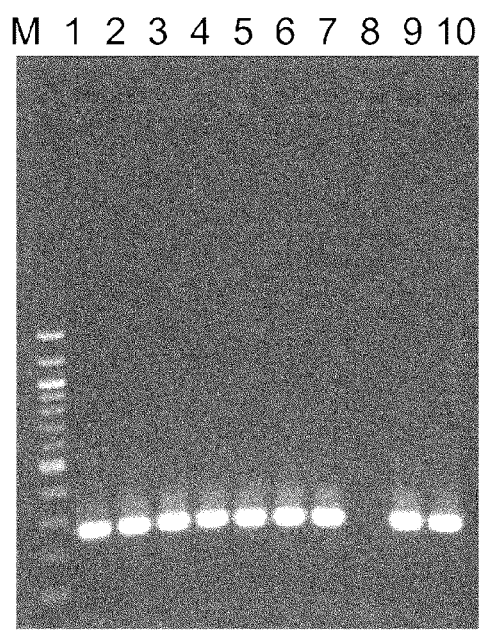
FIG. 14 presents a photograph showing PCR results of using common primers for detection of the *C. hyointestinalis* ATCC-type and Thai-type cdtB genes.

Bacterial Strains:
*C. hyointestinalis* Ch1-1, Ch87-4, Ch2037, Ch2039, Ch2973, Ch3839, Ch3857, ATCC35217, Ch022
*E. coli* C600
PCR:
1 µl of PCR template prepared from each bacterial strain by the boil method was mixed with the specific primers (final concentration: 0.5 µM), TaKaRa taq (0.25 U), dNTPs (200 µM each), and 10×Ex Taq Buffer. PCR was carried out at a total volume of 40 µl. The PCR conditions were as follows: 94° C. for three minutes, and 30 cycles of 94° C. for 30 seconds, 55° C. for 30 seconds, and 72° C. for 30 seconds, followed by 72° C. for five minutes. The resulting PCR products were electrophoresed on a 2% agarose gel. The gel was stained with ethidium bromide and then destained.
Results:
The *C. hyointestinalis* cdtB gene was successfully amplified for all of the seven *C. hyointestinalis* strains tested (FIG. 14).

Example 13

Development of CdtB Gene-Based Multiplex PCR for Detecting *C. jejuni*, *C. coli*, *C. fetus*, and *C. hyointestinalis*

Since primers that can efficiently amplify both the *C. hyointestinalis* ATCC-type and Thai-type cdtB genes were already developed, the primers were integrated into conventional multiplex PCR to develop multiplex PCR that can detect a broader range of *Campylobacter* bacteria.
Bacterial Strains:
*C. jejuni* 81-176 strain
*C. coli* Col-243 strain
*C. fetus* Col-187 strain
*C. lari* ATCC43675 strain
*C. upsaliensis* ATCC43954 strain
*C. hyointestinalis* Ch022 strain
*C. helveticus* ATCC51209 strain
*C. concisus* ATCC33237 strain
*E. coli* C600 strain
Primers:

```
Cj-CdtBU5:
                            (SEQ ID NO: 26)
5'-ATCTTTTAACCTTGCTTTTGC-3' (final concentration:
0.25 µM)

Cj-CdtBR6:
                            (SEQ ID NO: 27)
5'-GCAAGCATTAAAATCGCAGC-3'  (final concentration:
0.25 µM)

Cc-CdtBU5:
                            (SEQ ID NO: 28)
5'-TTTAATGTATTATTTGCCGC-3'  (final concentration:
0.5 µM)

Cc-CdtBR5:
                            (SEQ ID NO: 29)
5'-TCATTGCCTATGCGTATG-3'    (final concentration:
0.5 µM)

Cf-CdtBU6:
                            (SEQ ID NO: 30)
5'-GGCTTTGCAAAACCAGAAG-3'   (final concentration:
0.5 µM)

Cf-CdtBR3:
                            (SEQ ID NO: 31)
5'-CAAGAGTTCCTCTTAAACTC-3'  (final concentration:
0.5 µM)

ChspBU7:
                            (SEQ ID NO: 24)
5'-GTTCAAGAAGCAGGAAGC-3'    (final concentration:
0.5 µM)
```

-continued

ChspBR7:
(SEQ ID NO: 25)
5'-AATACCWAKAATWGGTCTTG-3' (final concentration:
0.5 µM)

(W: A or T; K: G or T)

PCR:

1 µl of PCR template prepared from each bacterial strain by the boil method was mixed with the specific primers, 0.2 µl of Multiplex PCR Mix 1 (Takara Bio), and 20 µl of 2× Multiplex PCR Mix 2 (Takara Bio). PCR was carried out at a total volume of 40 µl. The PCR conditions were as follows: 94° C. for one minute, and 30 cycles of 94° C. for 30 seconds, 56° C. for 90 seconds, and 72° C. for 90 seconds, followed by 72° C. for five minutes. The resulting PCR products were electrophoresed on a 2% agarose gel. The gel was stained with ethidium bromide and then destained.

Figure 15:
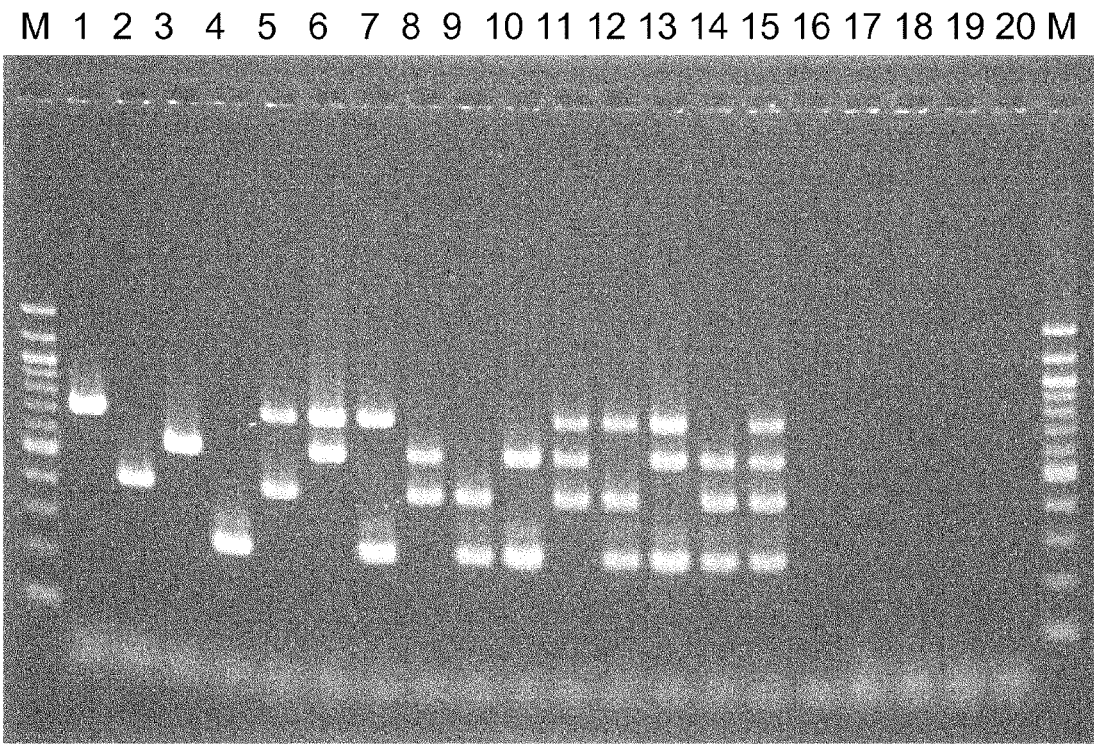
FIG. 15 presents a photograph showing the result of multiplex PCR based on the cdt genes of *C. jejuni, C. coli, C. fetus*, and *C. hyointestinalis*.

Results:

The multiplex PCR that targets the four bacterial species was able to efficiently detect the cdtB gene when any one of *C. jejuni*, *C. coli*, *C. fetus*, and *C. hyointestinalis* was present. Moreover, bacterial species-specific amplification of the gene was observed even in the presence of multiple bacterial species (FIG. 15).

Example 14

Novel Multiplex PCR that Targets Almost all Pathogenic *Campylobacter* Bacteria

Of *Campylobacter* bacteria, *C. jejuni*, *C. coli*, *C. fetus*, and *C. hyointestinalis* have catalase activity and grow at 42° C. These bacterial species are called "thermophilic Campylobacters", and most of the bacterial species that are responsible for food poisoning belong to this group. The present inventors developed multiplex PCR that can simultaneously detect the six *Campylobacter* bacterial species including *C. fetus* which is pathogenic for human and animals such as domestic animals, in addition to the five bacterial species belonging to the thermophilic Campylobacters.

Bacterial Strains:
  *C. jejuni* 81-176 strain
  *C. coli* Col-243 strain
  *C. fetus* Col-187 strain
  *C. lari* ATCC43675 strain
  *C. upsaliensis* ATCC43954 strain
  *C. hyointestinalis* Ch022 strain Primers:

Cj-CdtBU5:
(SEQ ID NO: 26)
5'-ATCTTTTAACCTTGCTTTTGC-3' (final concentration:
0.25 µM)

Cj-CdtBR6:
(SEQ ID NO: 27)
5'-GCAAGCATTAAAATCGCAGC-3' (final concentration:
0.25 µM)

Cc-CdtBU5:
(SEQ ID NO: 28)
5'-TTTAATGTATTATTTGCCGC-3' (final concentration:
0.375 µM)

-continued

Cc-CdtBR5:
(SEQ ID NO: 29)
5'-TCATTGCCTATGCGTATG-3' (final concentration:
0.375 µM)

Cf-CdtBU6:
(SEQ ID NO: 30)
5'-GGCTTTGCAAAACCAGAAG-3' (final concentration:
0.375 µM)

Cf-CdtBR3:
(SEQ ID NO: 31)
5'-CAAGAGTTCCTCTTAAACTC-3' (final concentration:
0.375 µM)

ChspBU7:
(SEQ ID NO: 24)
5'-GTTCAAGAAGCAGGAAGC-3' (final concentration:
0.375 µM)

ChspBR7:
(SEQ ID NO: 25)
5'-AATACCWAKAATWGGTCTTG-3' (final concentration:
0.375 µM)

CupspBU3:
(SEQ ID NO: 32)
5'-CATAGTTAGTCGCGTCCA-3' (final concentration:
0.375 µM)

CupspBR4:
(SEQ ID NO: 33)
5'-CCAGTTAATCTCAGGACG-3' (final concentration:
0.375 µM)

ClaspBU4:
(SEQ ID NO: 34)
5'-GTATCCATGCTTTATCAAGA-3' (final concentration:
0.375 µM)

ClaspBR4:
(SEQ ID NO: 35)
5'-GTAGGCCTATAAGAGAACC-3' (final concentration:
0.375 µM)

(W: A or T; K: G or T)

PCR:

0.5 µl of PCR template prepared from each bacterial strain by the boil method was mixed at the indicated final concentration with 0.2 µl of Multiplex PCR Mix 1 (Takara Bio), and 20 µl of 2× Multiplex PCR Mix 2 (Takara Bio). PCR was carried out at a total volume of 40 µl. The PCR conditions were as follows: 94° C. for one minute, and 30 cycles of 94° C. for 30 seconds, 56° C. for 90 seconds, and 72° C. for 90 seconds, followed by 72° C. for five minutes. The resulting PCR products were electrophoresed on a 2% agarose gel. The gel was stained with ethidium bromide and then destained.

Figure 16:
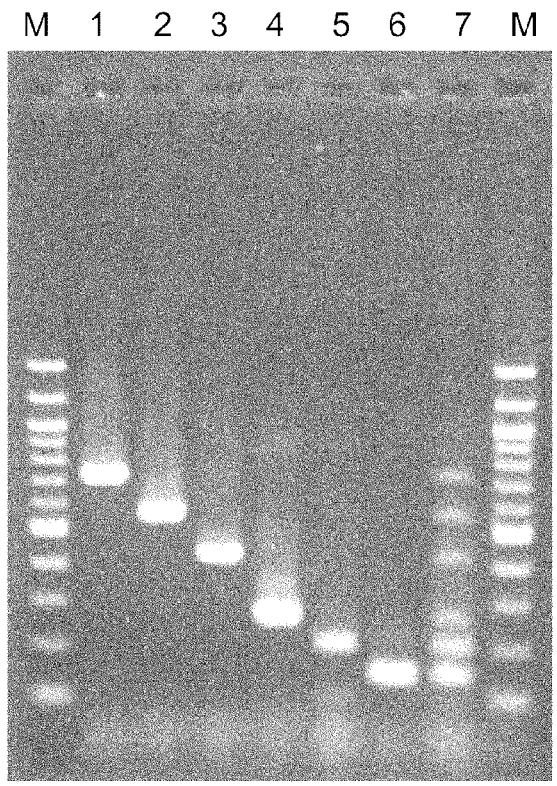
FIG. 16 presents a photograph showing the result of multiplex PCR based on the cdt genes of *C. jejuni, C. coli, C. fetus, C. hyointestinalis, C. lari*, and *C. upsaliensis*.

Results:

The multiplex PCR that targets the six bacterial species was able to efficiently detect the cdtB gene when any one of the *Campylobacter* species was present. Moreover, bacterial species-specific amplification of the gene was observed even in the presence of all six bacterial species (FIG. 16).

INDUSTRIAL APPLICABILITY

The present invention provides cdt genes which are useful for detection of C. hyointestinalis. Toxin production by the cdt genes was demonstrated.

As described above, C. hyointestinalis is an important bacterium from the viewpoint of public hygiene since it causes food poisoning. However, it was difficult to detect C. hyointestinalis, since the conventional culture and test methods target only C. jejuni and C. coli. Furthermore, it was difficult to identify the C. hyointestinalis cdt genes of the present invention by using known gene probes for bacteria belonging to the same genus, since homology of the C. hyointestinalis cdt genes to the C. jejuni, C. coli, and C. fetus cdt genes is not very high (approximately 60%).

The present invention enables rapid and accurate determination of bacteria that cause food poisoning or the like, since specific detection of C. hyointestinalis is possible. The methods of the present invention are very useful not only clinically but also in the process management of food production or such, factory hygiene management, etc.

The present invention also provides methods for detection of the six Campylobacter bacterial species including C. hyointestinalis. The Campylobacter bacteria targeted by the detection methods of the present invention excluding C. fetus are bacterial species that can grow at 42° C. under microaerophilic conditions, and thus are called "thermophilic Campylobacters". Almost all Campylobacter bacteria that are responsible for food poisoning are considered to belong to the thermophilic Campylobacters. The present invention enables simple and rapid identification of food poisoning bacteria.

The invention claimed is:

1. An isolated polynucleotide encoding a cytolethal distending toxin, which is any one of (a) to (h) below:
   (a) a polynucleotide encoding a polypeptide comprising the amino acid sequence of SEQ ID NOs: 2 or 4;
   (b) a polynucleotide comprising the nucleotide sequences of positions 962 to 1600 or 2425 to 3177 in the nucleotide sequence of SEQ ID NO: 1;
   (c) a polynucleotide encoding a polypeptide comprising an amino acid sequence having 90% or more sequence identity to the amino acid sequences of SEQ ID NOs: 2 or 4;
   (d) a polynucleotide that hybridizes under stringent conditions of 65° C. in a washing solution containing 0.2× SSC and 0.1% SDS to a DNA comprising the complementary sequence of the nucleotide sequences of positions 962 to 1600 or 2425 to 3177 in the nucleotide sequence of SEQ ID NO: 1;
   (e) a polynucleotide encoding a polypeptide comprising the amino acid sequence of any one of SEQ ID NOs: 6 to 8;
   (f) a polynucleotide comprising any one of the nucleotide sequences of positions 1059 to 1835, 1853 to 2656, and 2666 to 3202 in the nucleotide sequence of SEQ ID NO: 5; and
   (g) a polynucleotide encoding a polypeptide comprising an amino acid sequence having 90% or more sequence identity to the amino acid sequence of any one of SEQ ID NOs: 6 to 8; and
   (h) a polynucleotide that hybridizes under stringent conditions of 65° C. in a washing solution containing 0.2× SSC and 0.1% SDS to a DNA comprising any one of the complementary sequence of the nucleotide sequences of positions 1059 to 1835, 1853 to 2656, and 2666 to 3202 in the nucleotide sequence of SEQ ID NO: 5.

2. A vector comprising the polynucleotide of claim 1.

3. A host cell introduced with the isolated polynucleotide of claim 1 or the vector of claim 2.

4. A method for producing a polypeptide encoded by the polynucleotide of claim 1 comprising:
   culturing a host cell introduced with the polynucleotide or a vector comprising the polynucleotide, and
   collecting the produced polypeptide from the host cell or the culture supernatant.

5. A vector comprising a polynucleotide encoding a cytolethal distending toxin, which is any one of (a) to (h) below:
   (a) a polynucleotide encoding a polypeptide comprising the amino acid sequence of SEQ ID NOs: 2 or 4;
   (b) a polynucleotide comprising the nucleotide sequences of positions 962 to 1600 or 2425 to 3177 in the nucleotide sequence of SEQ ID NO: 1;
   (c) a polynucleotide encoding a polypeptide comprising an amino acid sequence having 90% or more sequence identity to the amino acid sequences of SEQ ID NOs: 2 or 4;
   (d) a polynucleotide that hybridizes under stringent conditions of 65° C. in a washing solution containing 0.2× SSC and 0.1% SDS to a DNA comprising the complementary sequence of the nucleotide sequences of positions 962 to 1600 or 2425 to 3177 in the nucleotide sequence of SEQ ID NO: 1;
   (e) a polynucleotide encoding a polypeptide comprising the amino acid sequence of any one of SEQ ID NOs: 6 to 8;

(f) a polynucleotide comprising any one of the nucleotide sequences of positions 1059 to 1835, 1853 to 2656, and 2666 to 3202 in the nucleotide sequence of SEQ ID NO: 5; and (g) a polynucleotide encoding a polypeptide comprising an amino acid sequence having 90% or more sequence identity to the amino acid sequence of any one of SEQ ID NOs: 6 to 8; and (h) a polynucleotide that hybridizes under stringent conditions of 65° C. in a washing solution containing 0.2× SSC and 0.1% SDS to a DNA comprising any one of the complementary sequence of the nucleotide sequences of positions 1059 to 1835, 1853 to 2656, and 2666 to 3202 in the nucleotide sequence of SEQ ID NO: 5.

6. A host cell transfected with a polypeptide encoding a cytolethal distending toxin, which is any one of (a) to (h) below:

(a) a polynucleotide encoding a polypeptide comprising the amino acid sequence of SEQ ID NOs: 2 or 4;

(b) a polynucleotide comprising the nucleotide sequences of positions 962 to 1600 or 2425 to 3177 in the nucleotide sequence of SEQ ID NO: 1;

(c) a polynucleotide encoding a polypeptide comprising an amino acid sequence having 90% or more sequence identity to the amino acid sequences of SEQ ID NOs: 2 or 4;

(d) a polynucleotide that hybridizes under stringent conditions of 65° C. in a washing solution containing 0.2× SSC and 0.1% SDS to a DNA comprising the complementary sequence of the nucleotide sequences of positions 962 to 1600 or 2425 to 3177 in the nucleotide sequence of SEQ ID NO: 1;

(e) a polynucleotide encoding a polypeptide comprising the amino acid sequence of any one of SEQ ID NOs: 6 to 8;

(f) a polynucleotide comprising any one of the nucleotide sequences of positions 1059 to 1835, 1853 to 2656, and 2666 to 3202 in the nucleotide sequence of SEQ ID NO: 5; and (g) a polynucleotide encoding a polypeptide comprising an amino acid sequence having 90% or more sequence identity to the amino acid sequence of any one of SEQ ID NOs: 6 to 8; and (h) a polynucleotide that hybridizes under stringent conditions of 65° C. in a washing solution containing 0.2× SSC and 0.1% SDS to a DNA comprising any one of the complementary sequence of the nucleotide sequences of positions 1059 to 1835, 1853 to 2656, and 2666 to 3202 in the nucleotide sequence of SEQ ID NO: 5.

7. A method for producing a polypeptide, comprising:
culturing the host cell of claim 6; and
collecting polypeptide expressed by the host cell.

8. An isolated polypeptide encoded by the polynucleotide of claim 1.

9. An isolated and purified polypeptide encoded by a cytolethal distending toxin, which is any one of (a) to (h) below:

(a) a polynucleotide encoding a polypeptide comprising the amino acid sequence of SEQ ID NOs: 2 or 4;

(b) a polynucleotide comprising the nucleotide sequences of positions 962 to 1600 or 2425 to 3177 in the nucleotide sequence of SEQ ID NO: 1;

(c) a polynucleotide encoding a polypeptide comprising an amino acid sequence having 90% or more sequence identity to the amino acid sequences of SEQ ID NOs: 2 or 4;

(d) a polynucleotide that hybridizes under stringent conditions of 65° C. in a washing solution containing 0.2× SSC and 0.1% SDS to a DNA comprising the complementary sequence of the nucleotide sequences of positions 962 to 1600 or 2425 to 3177 in the nucleotide sequence of SEQ ID NO: 1;

(e) a polynucleotide encoding a polypeptide comprising the amino acid sequence of any one of SEQ ID NOs: 6 to 8;

(f) a polynucleotide comprising any one of the nucleotide sequences of positions 1059 to 1835, 1853 to 2656, and 2666 to 3202 in the nucleotide sequence of SEQ ID NO: 5; and (g) a polynucleotide encoding a polypeptide comprising an amino acid sequence having 90% or more sequence identity to the amino acid sequence of any one of SEQ ID NOs: 6 to 8; and (h) a polynucleotide that hybridizes under stringent conditions of 65° C. in a washing solution containing 0.2× SSC and 0.1% SDS to a DNA comprising any one of the complementary sequence of the nucleotide sequences of positions 1059 to 1835, 1853 to 2656, and 2666 to 3202 in the nucleotide sequence of SEQ ID NO: 5.

* * * * *

UNITED STATES PATENT AND TRADEMARK OFFICE
CERTIFICATE OF CORRECTION

| | | |
|---|---|---|
| PATENT NO. | : 8,586,327 B2 | Page 1 of 1 |
| APPLICATION NO. | : 12/675726 | |
| DATED | : November 19, 2013 | |
| INVENTOR(S) | : Yamasaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this
Twenty-fifth Day of August, 2015

Michelle K. Lee
*Director of the United States Patent and Trademark Office*